US012584200B2

(12) United States Patent
Roth

(10) Patent No.: US 12,584,200 B2
(45) Date of Patent: Mar. 24, 2026

(54) COATING FOR METAL ALLOY

(71) Applicant: MiRus LLC, Marietta, GA (US)

(72) Inventor: Noah Roth, Marietta, GA (US)

(73) Assignee: MiRus LLC, Marietta, GA (US)

( * ) Notice: Subject to any disclaimer, the term of this patent is extended or adjusted under 35 U.S.C. 154(b) by 0 days.

(21) Appl. No.: 18/435,683

(22) Filed: Feb. 7, 2024

(65) Prior Publication Data

US 2024/0175110 A1    May 30, 2024

Related U.S. Application Data

(63) Continuation-in-part of application No. 18/204,180, filed on May 31, 2023, which is a continuation-in-part of application No. 18/116,677, filed on Mar. 2, 2023, and a continuation-in-part of application No. 17/586,270, filed on Jan. 27, 2022, application No. 18/435,683 is a continuation-in-part of application No. 17/586,270, filed on Jan. 27, 2022.

(60) Provisional application No. 63/389,281, filed on Jul. 14, 2022, provisional application No. 63/347,337, filed on May 31, 2022, provisional application No. 63/316,077, filed on Mar. 3, 2022, provisional application No. 63/226,270, filed on Jul. 28, 2021.

(51) Int. Cl.
| | |
|---|---|
| C22C 27/00 | (2006.01) |
| A61L 27/04 | (2006.01) |
| A61L 27/30 | (2006.01) |
| B22F 3/16 | (2006.01) |
| B22F 3/24 | (2006.01) |
| C22C 1/04 | (2023.01) |
| C22C 14/00 | (2006.01) |
| C22C 19/07 | (2006.01) |
| C22C 27/02 | (2006.01) |
| C22C 27/04 | (2006.01) |
| C22C 33/02 | (2006.01) |
| C22C 38/00 | (2006.01) |
| C22C 38/18 | (2006.01) |

(52) U.S. Cl.
CPC ............ *C22C 27/00* (2013.01); *A61L 27/047* (2013.01); *A61L 27/306* (2013.01); *B22F 3/16* (2013.01); *B22F 3/24* (2013.01); *C22C 1/0433* (2013.01); *C22C 1/045* (2013.01); *C22C 1/0458* (2013.01); *C22C 14/00* (2013.01); *C22C 19/07* (2013.01); *C22C 27/02* (2013.01); *C22C 27/04* (2013.01); *C22C 33/0278* (2013.01); *C22C 38/002* (2013.01); *C22C 38/18* (2013.01); *A61L 2430/20* (2013.01); *B22F 2003/242* (2013.01); *B22F 2301/20* (2013.01); *B22F 2998/10* (2013.01); *B22F 2999/00* (2013.01)

(58) Field of Classification Search
CPC ...... A61L 27/04; A61L 27/045; A61L 27/047; A61L 27/06; A61L 27/306; A61L 27/50; A61L 27/54; A61L 27/56; A61L 31/022; A61L 31/14; A61L 31/146; A61L 31/16; A61L 2430/20; A61L 2430/22; B22F 1/16; B22F 3/16; B22F 3/24; B22F 10/25; B22F 2003/242; B22F 2301/20; B22F 2998/10; B22F 2999/00; B33Y 70/10; B33Y 80/10; C22C 1/0433; C22C 1/045; C22C 1/0458; C22C 14/00; C22C 19/07; C22C 27/00; C22C 27/02; C22C 27/04; C22C 33/0257; C22C 33/0278; C22C 38/002; C22C 38/18; C23C 4/02; C23C 4/08; C23C 4/129; C23C 4/134; C23C 4/18; C23C 16/00; C23C 28/02; C23C 28/021; C23C 28/023; C23C 30/00
USPC .......................................................... 428/661
See application file for complete search history.

(56) References Cited

U.S. PATENT DOCUMENTS

| | | | |
|---|---|---|---|
| 11,266,767 B2 | 3/2022 | Roth et al. | |
| 2003/0072974 A1 | 4/2003 | Lau et al. | |
| 2003/0159920 A1 | 8/2003 | Roth | |
| 2005/0079200 A1* | 4/2005 | Rathenow | ............... A61L 31/10 427/2.24 |

(Continued)

FOREIGN PATENT DOCUMENTS

WO        2017132729        8/2017

OTHER PUBLICATIONS

Pedowitz et al., "Molybdenum Rhenium (MoRe) as a Biologically Superior Alloy for Foot and Ankle Implants", Foot & Ankle Orthopaedics, vol. 3, p. 1 (Sep. 19, 2018).

(Continued)

*Primary Examiner* — Katherine A Christy
(74) *Attorney, Agent, or Firm* — UB Greensfelder LLP; Brian E. Turung

(57) ABSTRACT

A metal alloy and that includes an enhancement coating material. The metal alloy includes rhenium and one or more additives. The enhancement coating is at least partially applied to the metal alloy by a physical vapor deposition (PVD) process, a chemical vapor deposition (CVD) process, an atomic layer deposition (ALD) process, a plasma-enhanced chemical vapor deposition (PE-CVD) process, ion implantation, direct energy deposition (DED), and/or thermal spray techniques like plasma arc spraying, flame spraying, high velocity oxy fuel spraying (HVOF). The enhancement coating is formed of a) 35-95 wt. % zirconium and wherein said enhancement coating includes ZrN, ZrNC, ZrOC or a combination of ZrN and ZrO2, b) 20-85 wt. % titanium and one or more of carbon, nitrogen, oxygen, rhenium, and silicon, c) 40-85 wt. % chromium and one or more of carbon, nitrogen, oxygen, rhenium, and silicon, or d) at least 60 wt. % carbon.

27 Claims, No Drawings

(56) References Cited

U.S. PATENT DOCUMENTS

| | | | |
|---|---|---|---|
| 2005/0191408 A1 | 9/2005 | Aharonov | |
| 2006/0136051 A1 | 6/2006 | Furst et al. | |
| 2006/0184251 A1* | 8/2006 | Zhang | A61F 2/30767 |
| | | | 623/23.56 |
| 2006/0200224 A1 | 9/2006 | Furst et al. | |
| 2008/0068924 A1 | 3/2008 | Midas et al. | |
| 2008/0183280 A1 | 7/2008 | Agnew | |
| 2009/0068249 A1 | 3/2009 | Furst et al. | |
| 2010/0023115 A1 | 1/2010 | Robaina et al. | |
| 2013/0084322 A1 | 4/2013 | Wu | |
| 2013/0216421 A1 | 8/2013 | Buckman, Jr. et al. | |
| 2014/0099279 A1 | 4/2014 | Furst et al. | |
| 2015/0157455 A1 | 6/2015 | Hoang | |
| 2015/0282929 A1 | 10/2015 | Rodriguez | |
| 2016/0237541 A1* | 8/2016 | Patel | B21C 23/002 |
| 2017/0216494 A1* | 8/2017 | Roth | B21C 1/00 |
| 2017/0273785 A1 | 9/2017 | Seguin et al. | |
| 2018/0305528 A1 | 10/2018 | James et al. | |
| 2018/0361017 A1 | 12/2018 | Roth | |
| 2019/0008995 A1* | 1/2019 | Roth | A61L 27/50 |
| 2019/0046684 A1 | 2/2019 | Roth et al. | |
| 2020/0306067 A1 | 10/2020 | Nia | |
| 2021/0154373 A1 | 5/2021 | Park | |
| 2021/0236688 A1 | 8/2021 | Wagner | |
| 2021/0251766 A1 | 8/2021 | Quintana-Ponce et al. | |

OTHER PUBLICATIONS

Alotaibi et al., "Antibacterial Properties of Cu—ZrO2 Thin Film Prepared via Aerosol Assisted Chemical Vapour Deposition", Journal of Materials Chemistry B, pp. 3-4, 8-10 (2015).

Singh et al., "Synthesis of New Zirzonium (IV) Complexes with Amino Acid Schiff Bases; Spectral, Molecular Modeling, and Flourescence Studies", International Journal of Organic Chemistry, pp. 5-6 (Jan. 2023).

Kumari et al., "Zirconia-based nanomaterials; recent developments in syntheses and application", pp. 4225 (Aug. 2022).

* cited by examiner

COATING FOR METAL ALLOY

The present disclosure is a continuation in part of U.S. patent application Ser. No. 17/586,270 filed Jan. 27, 2022, which in turn claims priority on U.S. Provisional Application Ser. No. 63/226,270 filed Jul. 28, 2021, which are both incorporated herein by reference.

The present disclosure is a continuation-in-part of U.S. patent application Ser. No. 18/204,180 filed May 31, 2023, which in turn claims priority on U.S. Provisional Application Ser. No. 63/389,281 filed Jul. 14, 2022, which is incorporated herein by reference.

The present disclosure is a continuation-in-part of U.S. patent application Ser. No. 18/204,180 filed May 31, 2023, which in turn claims priority on U.S. Provisional Application Ser. No. 63/347,337 filed May 31, 2022, which is incorporated herein by reference.

The present disclosure is a continuation in part of U.S. patent application Ser. No. 18/116,677 filed Mar. 2, 2023, which in turn claims priority on U.S. Provisional Application Ser. No. 63/316,077 filed Mar. 3, 2022, which is incorporated herein by reference.

The present disclosure is directed to a protective coating for metal alloy such as, but not limited to, refractory metal alloys that include rhenium and a protective coating, and even more particularly to a medical device that is at least partially formed of a refractory metal alloy wherein the refractory metal alloy includes a protective coating.

BACKGROUND OF DISCLOSURE

Stainless steel, cobalt-chromium alloys, and TiAlV alloys are some of the more common metal alloys used for medical devices. Although these alloys have been successful in forming a variety of medical devices, these alloys have several deficiencies.

The present disclosure is directed to a refractory metal alloy, and in particular to a refractory metal alloy that include rhenium, and wherein in the refractory metal alloy is partially or fully coated with material that improves one or more properties of the refractory metal alloy.

SUMMARY OF THE DISCLOSURE

The present disclosure is directed to a protective coating for metal alloy such as, but not limited to, refractory metal alloys that include rhenium and a protective coating, and even more particularly to a medical device that is at least partially formed of a refractory metal alloy wherein the refractory metal alloy includes a protective coating. As defined herein, a refractory metal alloy is a metal alloy that includes at least 20 wt. % of one or more of Mo, Re, Nb, Ta or W. Non-limiting refractory metal alloys include MoRe alloy, ReW alloy, MoReCr alloy, MoReTa alloy, MoReTi alloy, WCu alloy, ReCr alloy, Mo alloy, Re alloy, W alloy, Ta alloy, Nb alloy, etc. In one non-limiting embodiment, the refractory metal alloy includes at least 20 wt. % of rhenium. Non-limiting refractory metal alloys that include rhenium include, but are not limited to, MoRe alloy, ReW alloy, MoReCr alloy, MoReTa alloy, MoReTi alloy, ReCr alloy, etc.

In accordance with one non-limiting aspect of the present disclosure, the medical device can include, but is not limited to, a PFO (patent foramen ovale) device; stent (e.g., stent for used in aortic, iliac, subclavian, carotid, femoral artery, tibial, intracranial arteries, etc.); aneurysm exclusion devices (e.g., devices for aneurysm for use in aorta, iliac, intracranial arteries, etc.); valve (e.g., heart valve, TAVR valve, aortic, mitral valve replacement, tricuspid valve replacement, pulmonary valve replacement, etc.); anchoring devices for valves (e.g., anchoring devices for heart valve, TAVR valve, aortic valve, mitral valve, tricuspid valve, pulmonary valve, etc.); valve frames; occluders (e.g., occluders for patent foramen ovale, ventricular septal defect, left atrial appendage, etc.); guide wire; vascular implant; graft; guide wire; sheath, expandable sheath; catheter; needle; stent catheter; electrophysiology catheter; hypotube; staple; cutting device; pacemaker; dental implant; dental crown; dental braces; wire used in medical procedures; spinal implant; spinal discs; frame and other structure for use with a spinal implant; bone implant; artificial disk; artificial spinal disk; spinal interbody; expandable spinal interbody; interbody fusion device; expandable interbody fusion device; prosthetic implant or device to repair, replace and/or support a bone (e.g., acromion, atlas, axis, calcaneus, carpus, clavicle, coccyx, epicondyle, epitrochlea, femur, fibula, frontal bone, greater trochanter, humerus, ilium, ischium, mandible, maxilla, metacarpus, metatarsus, occipital bone, olecranon, parietal bone, patella, phalanx, radius, ribs, sacrum, scapula, sternum, talus, tarsus, temporal bone, tibia, ulna, zygomatic bone, etc.) and/or cartilage; sutures; surgical staples; bone plate; knee replacement; hip replacement; shoulder replacement; ankle replacement; nail; rod; screw; post; cage; expandable cage; expandable orthopedic insert; plate (e.g., bone plate, cervical plate, spinal plate, etc.); bone plate nail; spinal rod; bone screw; post; spinal cage; pedicle screw; cap; hinge; joint system; screw extension; tulip extension; tether; graft; anchor; spacer; shaft; disk; ball; tension band; locking connector or other structural assembly that is used in a body to support a structure, mount a structure, and/or repair a structure in a body such as, but not limited to, a human body, animal body, etc.

In accordance with another and/or alternative non-limiting aspect of the present disclosure, there is provided a medical device partially or fully formed of a metal alloy. In one non-limiting embodiment, 50-100% (and all values and ranges therebetween) of the medical device is formed of the metal alloy. In another non-limiting embodiment, at least 30 wt. % (e.g., 30-100 wt. % and all values and ranges therebetween) of the medical device is formed of a refractory metal alloy that includes rhenium (e.g., MoRe alloy, ReW alloy, MoReCr alloy, MoReTa alloy, MoReTi alloy, or ReCr alloy, etc.).

In accordance with another and/or alternative non-limiting aspect of the present disclosure, the metal alloy that is used to form at least a portion of the medical device has one or more improved properties (e.g., strength, durability, hardness, biostability, bendability, coefficient of friction, radial strength, flexibility, tensile strength, tensile elongation, longitudinal lengthening, stress-strain properties, reduced recoil, radiopacity, heat sensitivity, biocompatibility, improved fatigue life, crack resistance, crack propagation resistance, reduced magnetic susceptibility, etc.), improved conformity when bent, less recoil, increase yield strength, improved fatigue ductility, improved durability, improved fatigue life, reduced adverse tissue reactions, reduced metal ion release, reduced corrosion, reduced allergic reaction, improved hydrophilicity, reduced toxicity, reduced thickness of metal component, improved bone fusion, and/or lower ion release into tissue. These one or more improved physical properties of the metal alloy can be achieved in the medical device without having to increase the bulk, volume, and/or weight of the medical device, and in some instances these improved physical properties can be obtained even when the volume, bulk, and/or weight of the medical device is reduced as compared to medical devices that are at least partially formed from traditional stainless steel, titanium alloy, or cobalt and chromium alloy materials.

In accordance with another and/or alternative non-limiting aspect of the present disclosure, the metal alloy used to at least partially form the medical device can thus 1) increase the radiopacity of the medical device, 2) increase the radial strength of the medical device, 3) increase the yield strength and/or ultimate tensile strength of the medical device, 4) improve the stress-strain properties of the medical device, 5) improve the crimping and/or expansion properties of the medical device, 6) improve the bendability and/or flexibility of the medical device, 7) improve the strength and/or durability of the medical device, 8) increase the hardness of the medical device, 9) improve the recoil properties of the medical device, 10) improve the biostability and/or biocompatibility properties of the medical device, 11) increase fatigue resistance of the medical device, 12) resist cracking in the medical device and resist propagation of cracks, 13) enable smaller, thinner, and/or lighter weight medical device to be made, 14) reduce the outer diameter of a crimped medical device, 15) improve the conformity of the medical device to the shape of the treatment area when the medical device is used and/or expanded in the treatment area, 16) reduce the amount of recoil of the medical device to the shape of the treatment area when the medical device is expanded in the treatment area, 17) increase yield strength of the medical device, 18) improve fatigue ductility of the medical device, 18) improve durability of the medical device, 19) improve fatigue life of the medical device, 20) reduce adverse tissue reactions after implant of the medical device, 21) reduce metal ion release after implant of the medical device, 22) reduce corrosion of the medical device after implant of the medical device, 23) reduce allergic reaction after implant of the medical device, 24) improve hydrophilicity of the medical device, 25) reduce thickness of meta component of medical device, 26) improve bone fusion with medical device, and/or 27) lower ion release from medical device into tissue, 28) reduce magnetic susceptibility of the medical device when implanted in a patient, and/or 29) reduce toxicity of the medical device after implant of the medical device.

Another and/or alternative non-limiting object of the present disclosure is the provision of a medical device that is partially or fully formed of a metal alloy that has one or more of the following properties: i) at least 70-100% of the orthopedic medical device is formed of a metal alloy that has a yield strength of at least 110 ksi, ii) at least 70-100% of the orthopedic medical device is formed of a metal alloy that has a modulus of elasticity of at least 35000 ksi, iii) at least 70-100% of the orthopedic medical device is formed of a metal alloy that is formed of a rhenium containing metal alloy that includes at least 0.1 wt. % rhenium and one or more metals selected from the group consisting of Mo, Cr, Co, Ni, Ti, Ta, Nb, Zr, and W.

In accordance with another and/or alternative non-limiting aspect of the present disclosure, the medical device is optionally subjected to one or more manufacturing processes. These manufacturing processes can include, but are not limited to, expansion, laser cutting, etching, crimping, annealing, drawing, pilgering, electroplating, electro-polishing, machining, plasma coating, 3D printing, 3D printed coatings, chemical vapor deposition, chemical polishing, cleaning, pickling, ion beam deposition or implantation, sputter coating, vacuum deposition, etc. In one non-limiting embodiment, a portion or all of the medical device is formed by a 3D printing process.

In accordance with another and/or alternative non-limiting aspect of the present disclosure, the refractory metal alloy that is used to at least partially form the medical device optionally has a generally uniform density throughout the refractory metal alloy, and also results in the desired yield and ultimate tensile strengths of the refractory metal alloy. The density of the refractory metal alloy is generally at least about 5 gm/cc (e.g., 5 gm/cc-21 gm/cc and all values and ranges therebetween; 10-20 gm/cc; etc.), and typically at least about 11-19 gm/cc. This substantially uniform high density of the refractory metal alloy can optionally improve the radiopacity of the refractory metal alloy.

In accordance with another and/or alternative non-limiting aspect of the present disclosure, the refractory metal alloy optionally includes a certain amount of carbon and oxygen; however, this is not required. These two elements have been found to affect the forming properties and brittleness of the refractory metal alloy. The controlled atomic ratio of carbon and oxygen of the refractory metal alloy also can be used to minimize the tendency of the refractory metal alloy to form micro-cracks during the forming of the refractory metal alloy at least partially into a medical device, and/or during the use and/or expansion of the medical device in a body passageway. The control of the atomic ratio of carbon to oxygen in the refractory metal alloy allows for the redistribution of oxygen in the refractory metal alloy to minimize the tendency of micro-cracking in the refractory metal alloy during the forming of the refractory metal alloy at least partially into a medical device, and/or during the use and/or expansion of the medical device in a body passageway. The atomic ratio of carbon to oxygen in the refractory metal alloy is believed to facilitate in minimizing the tendency of micro-cracking in the refractory metal alloy and improve the degree of elongation of the refractory metal alloy, both of which can affect one or more physical properties of the refractory metal alloy that are useful or desired in forming and/or using the medical device. The carbon to oxygen atomic ratio can be as low as about 0.2:1 (e.g., 0.2:1 to 50:1 and all values and ranges therebetween). In one non-limiting formulation of the refractory metal alloy, the carbon to oxygen atomic ratio in the refractory metal alloy is generally at least about 0.3:1. Typically, the carbon content of the refractory metal alloy is less than about 0.2 wt. % (e.g., 0 wt. % to 0.1999999 wt. % and all values and ranges therebetween). Carbon contents that are too large can adversely affect the physical properties of the refractory metal alloy. Generally, the oxygen content is to be maintained at very low level. In one non-limiting formulation of the refractory metal alloy, the oxygen content is less than about 0.1 wt. % of the refractory metal alloy (e.g., 0 wt. to 0.0999999 wt. % and all values and ranges therebetween). It is believed that the refractory metal alloy will have a very low tendency to form micro-cracks during the formation of the medical device and after the medical device has been inserted into a patient by closely controlling the carbon to oxygen ration when the oxygen content exceeds a certain amount in the refractory metal alloy. In one non-limiting arrangement, the carbon to oxygen atomic ratio in the refractory metal alloy is at least about 2.5:1 when the oxygen content is greater than about 100 ppm in the refractory metal alloy.

In accordance with another and/or alternative non-limiting aspect of the present disclosure, the refractory metal alloy optionally includes a controlled amount of nitrogen;

however, this is not required. Large amounts of nitrogen in the refractory metal alloy can adversely affect the ductility of the refractory metal alloy. This can in turn adversely affect the elongation properties of the refractory metal alloy. A too high nitrogen content in the refractory metal alloy can begin to cause the ductility of the refractory metal alloy to unacceptably decrease, thus adversely affect one or more physical properties of the refractory metal alloy that are useful or desired in forming and/or using the medical device. In one non-limiting formulation, the refractory metal alloy includes less than about 0.001 wt. % nitrogen (e.g., 0 wt. % to −0.0009999 wt. % and all values and ranges therebetween). It is believed that the nitrogen content should be less than the content of carbon or oxygen in the refractory metal alloy. In one non-limiting formulation of the refractory metal alloy, the atomic ratio of carbon to nitrogen is at least about 1.5:1 (e.g., 1.5:1 to 400:1 and all values and ranges therebetween). In another non-limiting formulation of the refractory metal alloy, the atomic ratio of oxygen to nitrogen is at least about 1.2:1 (e.g., 1.2:1 to 150:1 and all value and ranges therebetween).

In another and/or alternative non-limiting aspect of the present disclosure, the medical device is generally designed to include at least about 5 wt. % of the refractory metal alloy (e.g., 5-100 wt. % and all values and ranges therebetween). In one non-limiting embodiment of the disclosure, the medical device includes at least about 50 wt. % of the refractory metal alloy. In another non-limiting embodiment of the disclosure, the medical device includes at least about 95 wt. % of the refractory metal alloy. In one specific configuration, when the medical device includes an expandable frame, the expandable frame is formed of 50-100 wt. % (and all values and ranges therebetween) of the refractory metal alloy, and typically 75-100 wt. % of the refractory metal alloy.

In another and/or alternative non-limiting aspect of the present disclosure, the metal alloy used to form all or part of the medical device 1) is optionally not clad, metal sprayed, plated, and/or formed (e.g., cold worked, hot worked, etc.) onto another metal, or 2) optionally does not have another metal or metal alloy metal sprayed, plated, clad, and/or formed onto the metal alloy.

In accordance with another and/or alternative non-limiting aspect of the present disclosure, the metal alloy that is used to form all or part of the medical device 1) is clad, metal sprayed, plated and/or formed (e.g., cold worked, hot worked, etc.) onto another metal, or 2) has another metal or metal alloy metal sprayed, plated, clad and/or formed onto the metal alloy.

In accordance with another and/or alternative non-limiting aspect of the present disclosure, the medical device can optionally be at least partially or fully formed from a tube or rod of metal alloy, or be formed into shape that is at least 80% of the final net shape of the medical device.

In accordance with another and/or alternative non-limiting aspect of the present disclosure, the medical device can be at least partially or fully formed from by 3D printing.

In accordance with another and/or alternative non-limiting aspect of the present disclosure, the metal alloy has several physical properties that positively affect the medical device when the medical device is at least partially formed of the metal alloy of the present disclosure. In one non-limiting embodiment of the disclosure, the average Vickers hardness of metal alloy of the present disclosure used to at least partially form the medical device is optionally at least about 150 Vickers (e.g., 150-300 Vickers and all values and ranges therebetween); and typically 160-240 Vickers; however, this is not required. The metal alloy of the present disclosure generally has an average hardness that is greater than stainless steel (e.g., Grade 304, Grade 316). In another and/or alternative non-limiting embodiment of the disclosure, the average ultimate tensile strength of the metal alloy of the present disclosure is optionally at least about 100 ksi (e.g., 100-350 ksi and all values and ranges therebetween); however, this is not required. In still another and/or alternative non-limiting embodiment of the disclosure, the average yield strength of the metal alloy of the present disclosure is optionally at least about 80 ksi (e.g., 80-300 ksi and all values and ranges therebetween); however, this is not required. In yet another and/or alternative non-limiting embodiment of the disclosure, the average grain size of the metal alloy of the present disclosure used to at least partially form the medical device is optionally no greater than about 4 ASTM (e.g., 4 ASTM to 20 ASTM using ASTM E112 and all values and ranges therebetween, e.g., 0.35 micron to 90 micron, and all values and ranges therebetween). The small grain size of the metal alloy of the present disclosure enables the medical device to have the desired elongation and ductility properties that are useful in enabling the medical device to be formed, crimped, and/or expanded.

In another and/or alternative non-limiting embodiment of the disclosure, the average tensile elongation of the metal alloy of the present disclosure used to at least partially form the medical device is optionally at least about 25% (e.g., 25%-50% average tensile elongation and all values and ranges therebetween). An average tensile elongation of at least 25% for the metal alloy is useful to facilitate in the medical device being properly expanded when positioned in the treatment area of a body passageway. A medical device that does not have an average tensile elongation of at least about 25% may be more prone to the formation of microcracks and/or break during the forming, crimping, and/or expansion of the medical device.

In accordance with another and/or alternative non-limiting aspect of the present disclosure, the unique combination of the metals in the metal alloy of the present disclosure in combination with achieving the desired purity and composition of the metal alloy and the desired grain size of the metal alloy results in 1) a medical device having the desired high ductility at about room temperature, 2) a medical device having the desired amount of tensile elongation, 3) a homogeneous or solid solution of a metal alloy having high radiopacity, 4) a reduction or prevention of micro-crack formation and/or breaking of the metal alloy of the present disclosure tube when the tube is sized and/or cut to form the medical device, 5) a reduction or prevention of micro-crack formation and/or breaking of the medical device when the medical device is crimped, 6) a reduction or prevention of micro-crack formation and/or breaking of the medical device when the medical device is bent and/or expanded in a body passageway, 7) a medical device having the desired ultimate tensile strength and yield strength, 8) a medical device having very thin wall thicknesses and still having the desired radial forces needed to retain the medical device on an open state when expanded, 9) a medical device exhibiting less recoil when the medical device is crimped onto a delivery system and/or expanded in a body passageway, 10) a medical device exhibiting improved conformity to the shape of the treatment area in the body passageway when the medical device is expanded in a body passageway, 11) a medical device exhibiting improved fatigue ductility, and/or 12) a medical device that exhibits improved durability.

In accordance with another and/or alternative non-limiting aspect of the present disclosure, at least 30 wt. % (e.g., 30-100 wt. % and all values and ranges therebetween) of the refractory metal alloy includes one or more of molybdenum, niobium, rhenium, tantalum, or tungsten. In another non-limiting embodiment, at least 40 wt. % of the refractory metal alloy includes one or more of molybdenum, niobium, rhenium, tantalum, or tungsten. In another non-limiting embodiment, at least 50 wt. % of the refractory metal alloy includes one or more of molybdenum, niobium, rhenium, tantalum, or tungsten.

In accordance with another and/or alternative non-limiting aspect of the present disclosure, there is provided a refractory metal alloy wherein at least 20 wt. % (e.g., 20-99 wt. % and all values and ranges therebetween) of the refractory metal alloy includes rhenium. In one non-limiting embodiment, the refractory metal alloy includes at least 20 wt. % (e.g., 20-99.9 wt. % and all values and ranges therebetween) rhenium, and 0.1-80 wt. % (and all values and ranges therebetween) of one or more of aluminum, bismuth, calcium, carbon, chromium, cobalt, copper, gold, hafnium, iridium, iron, lanthanum, magnesium, manganese, molybdenum, nickel, niobium, osmium, platinum, rare earth metals, rhodium, ruthenium, silver, tantalum, technetium, titanium, tungsten, vanadium, yttrium, zinc, zirconium, and/or alloys of one or more of such components.

In another non-limiting aspect of the present disclosure, the metals used to form the refractory metal alloy includes rhenium and tungsten and optionally one or more alloying agents such as, but not limited to, aluminum, bismuth, calcium, carbon, chromium, cobalt, copper, gold, hafnium, iron, magnesium, molybdenum, nickel, niobium, osmium, platinum, rare earth metals, rhenium, silver, tantalum, technetium, titanium, vanadium, yttrium, zinc, zirconium, and/or alloys of one or more of such components (e.g., WRe, WReMo, etc.). Although the refractory metal alloy is described as including one or more metals, it can be appreciated that some of the metals in the refractory metal alloy can be substituted for one or more materials selected from the group of ceramics, plastics, thermoplastics, thermosets, rubbers, laminates, non-wovens, etc. In one non-limiting formulation, the refractory metal alloy includes 1-40 wt. % rhenium (and all values and ranges therebetween) and 60-99 wt. % tungsten (and all values and ranges therebetween). In one non-limiting embodiment, the total weight percent of the tungsten and rhenium in the tungsten-rhenium alloy is at least about 95 wt. %, typically at least about 99 wt. %, more typically at least about 99.5 wt. %, yet more typically at least about 99.9 wt. %, and still more typically at least about 99.99 wt. %. In another non-limiting formulation, the refractory metal alloy includes 1-47.5 wt. % rhenium (and all values and ranges therebetween) and 20-80 wt. % tungsten (and all values and ranges therebetween) and 1-47.5 wt. % molybdenum (and all values and ranges therebetween). The total weight percent of the tungsten, rhenium, and molybdenum in the tungsten-rhenium-molybdenum alloy is at least about 95 wt. %, typically at least about 99 wt. %, more typically at least about 99.5 wt. %, yet more typically at least about 99.9 wt. %, and still more typically at least about 99.99 wt. %. In one non-limiting specific tungsten-rhenium-molybdenum alloy, the weight percent of the tungsten is greater than a weight percent of rhenium and also greater than the weight percent of molybdenum. In another non-limiting specific tungsten-rhenium-molybdenum alloy, the weight percent of the tungsten is greater than 50 wt. % of the tungsten-rhenium-molybdenum alloy. In another non-limiting specific tungsten-rhenium-molybdenum alloy, the weight percent of the tungsten is greater than a weight percent of rhenium, but less than a weigh percent of molybdenum. In another non-limiting specific tungsten-rhenium-molybdenum alloy, the weight percent of the tungsten is greater than a weight percent of molybdenum, but less than a weigh percent of rhenium. In another non-limiting specific tungsten-rhenium-molybdenum alloy, the weight percent of the tungsten is less than a weight percent of rhenium and also less than the weight percent of molybdenum.

In another non-limiting aspect of the present disclosure, the metals used to form the refractory metal alloy include rhenium, molybdenum, and one or more additives selected from the group consisting of aluminum, bismuth, calcium, carbon, chromium, cobalt, copper, gold, hafnium, iridium, iron, lanthanum, magnesium, manganese, molybdenum, nickel, niobium, osmium, platinum, rare earth metals, rhodium, ruthenium, silver, tantalum, technetium, titanium, tungsten, vanadium, yttrium, zinc, and/or zirconium. In one non-limiting embodiment, a combined weight percentage of rhenium and alloy metals in the refractory metal alloy is greater than or equal to the weight percent of molybdenum in the refractory metal alloy. In another non-limiting embodiment, a combined weight percentage of rhenium and alloy metals in the refractory metal alloy is greater than the weight percent of molybdenum in the refractory metal alloy. In another non-limiting embodiment, a weight percent of molybdenum in the refractory metal alloy is at least 10 wt. % and less than 60 wt. % (and all values and ranges therebetween). In another non-limiting embodiment, a weight percent of rhenium in the refractory metal alloy is 35-60 wt. % (and all values and ranges therebetween). In another non-limiting embodiment, a combined weight percent of the alloying metals is 5-45 wt. % (and all values and ranges therebetween) of the refractory metal alloy. In another non-limiting embodiment, a weight percent of the rhenium in the refractory metal alloy is greater than a combined weight percent of the alloying metals. In another non-limiting embodiment, a combined weight percent of the rhenium, molybdenum, and the one or more alloying metals in the refractory metal alloy is at least 99.9 wt. %. In another non-limiting embodiment, alloy metal includes chromium. In another non-limiting embodiment, the alloying metal includes chromium and one or more metals selected from the group consisting of bismuth, zirconium, iridium, niobium, tantalum, titanium, and yttrium. In another non-limiting embodiment, the alloying metal includes chromium and one or more metals selected from the group consisting of bismuth, zirconium, iridium, niobium, tantalum, titanium, and yttrium; and wherein an atomic ratio of chromium to an atomic ratio of each or all of the metals selected from the group consisting of bismuth, chromium, iridium, niobium, tantalum, titanium, and yttrium is 0.4:1 to 2.5:1 (and all values and ranges therebetween). In another non-limiting embodiment, the alloying metal includes chromium and one or more metals selected from the group consisting of zirconium, niobium, and tantalum. In another non-limiting embodiment, the alloying metal includes a first metal selected from the group consisting of bismuth, chromium, iridium, niobium, tantalum, titanium, yttrium and zirconium, and a second metal selected from the group consisting of bismuth, chromium, iridium, niobium, tantalum, titanium, yttrium and zirconium; and wherein the first and second metals are different; and wherein an atomic ratio of the first metal to the second metal is 0.4:1 to 2.5:1 (and all values and ranges therebetween). In another non-limiting embodiment, the alloying metal a first metal selected from the group consisting of chromium, niobium, tantalum, and zirconium, and a second metal selected from the group consisting of chromium, niobium, tantalum, and zirconium; and wherein the first and second metals are different; and wherein an atomic ratio of the first metal to the second metal is 0.4:1 to 2.5:1 (and all values and ranges therebetween).

In accordance with another and/or alternative non-limiting aspect of the present disclosure, the weight percent of rhenium plus the weigh percent of the combined weight percentage of bismuth, niobium, tantalum, tungsten, titanium, vanadium, chromium, manganese, yttrium, zirconium, technetium, ruthenium, rhodium, hafnium, osmium, copper, and iridium is greater than the weight percent of molybdenum in the refractory metal alloy. In one specific non-limiting formulation, the weight percent of rhenium plus the weigh percent of the combined weight percentage of bismuth, chromium, iridium, niobium, tantalum, titanium, yttrium, and zirconium is greater than the weight percent of molybdenum in the refractory metal alloy. In another specific non-limiting formulation, the weight percent of rhenium plus the weigh percent of the combined weight percentage of chromium, niobium, tantalum, and zirconium is greater than the weight percent of molybdenum in the refractory metal alloy.

In accordance with another and/or alternative non-limiting aspect of the present disclosure, the atomic weight percent of rhenium to the atomic weight percent of the combination of bismuth, niobium, tantalum, tungsten, titanium, vanadium, chromium, manganese, yttrium, zirconium, technetium, ruthenium, rhodium, hafnium, osmium, copper, and iridium in the refractory metal alloy is 0.7:1 to 1.5:1 (and all values and ranges therebetween), typically 0.8:1 to 1.4:1, more typically 0.8:1 to 1.25:1, and still more typically about 0.9:1 to 1.1:1 (e.g., 1:1). In one specific non-limiting formulation, the atomic weight percent of rhenium to the atomic weight percent of the combination of bismuth, chromium, iridium, niobium, tantalum, titanium, yttrium, and zirconium is 0.7:1 to 5.1:1 (and all values and ranges therebetween), typically 0.8:1 to 1.5:1, more typically 0.8:1 to 1.25:1, and still more typically about 0.9:1 to 1.1:1 (e.g., 1:1). In one specific non-limiting formulation, the atomic weight percent of rhenium to the atomic weight percent of the combination of chromium, niobium, tantalum, and zirconium is 0.7:1 to 5.1:1 (and all values and ranges therebetween), typically 0.8:1 to 1.5:1, more typically 0.8:1 to 1.25:1, and still more typically about 0.9:1 to 1.1:1 (e.g., 1:1).

In accordance with another and/or alternative non-limiting aspect of the present disclosure, when the refractory metal alloy includes two of bismuth, niobium, tantalum, tungsten, titanium, vanadium, chromium, manganese, yttrium, zirconium, technetium, ruthenium, rhodium, hafnium, osmium, copper, and iridium, the atomic ratio of the two metals is 0.4:1 to 2.5:1 (and all values and ranges therebetween), and typically 0.5:1 to 2:1. In one specific non-limiting formulation, when the refractory metal alloy includes two of bismuth, chromium, iridium, niobium, tantalum, titanium, yttrium, and zirconium, the atomic ratio of the two metals is 0.4:1 to 2.5:1 (and all values and ranges therebetween), and typically 0.5:1 to 2:1. In another specific non-limiting formulation, when the refractory metal alloy includes two of chromium, niobium, tantalum, and zirconium, the atomic ratio of the two metals is 0.4:1 to 2.5:1 (and all values and ranges therebetween), and typically 0.5:1 to 2:1.

In accordance with another and/or alternative non-limiting aspect of the present disclosure, at least 35 wt. % (e.g., 35-75 wt. % and all values and ranges therebetween) of the refractory metal alloy includes rhenium, and the refractory metal alloy also includes chromium. In one non-limiting embodiment, at least 25 wt. % (e.g., 25-49.9 wt. % and all values and ranges therebetween) of the refractory metal alloy includes chromium. In another non-limiting embodiment, at least 30 wt. % of the refractory metal alloy includes chromium. In another non-limiting embodiment, at least 33 wt. % of the refractory metal alloy includes chromium. In another non-limiting embodiment, at least 50 wt. % (e.g., 50-74.9 wt. % and all values and ranges therebetween) of the refractory metal alloy includes rhenium, at least 25 wt. % (e.g., 25-49.9 wt. % and all values and ranges therebetween) of the refractory metal alloy includes chromium, and 0.1-25 wt. % (and all values and ranges therebetween) of the refractory metal alloy includes one or more of molybdenum, bismuth, niobium, tantalum, titanium, vanadium, tungsten, manganese, zirconium, technetium, ruthenium, rhodium, hafnium, osmium, copper, yttrium, zirconium, and/or iridium. In another non-limiting embodiment, at least 55 wt. % (e.g., 55-69.9 wt. % and all values and ranges therebetween) of the refractory metal alloy includes rhenium, at least 30 wt. % (e.g., 30-44.9 wt. % and all values and ranges therebetween) of the refractory metal alloy includes chromium, and 0.1-15 wt. % (and all values and ranges therebetween) of the refractory metal alloy includes one or more of molybdenum, bismuth, niobium, tantalum, titanium, vanadium, tungsten, manganese, zirconium, technetium, ruthenium, rhodium, hafnium, osmium, copper, yttrium, zirconium, and/or iridium. In another non-limiting embodiment, at least 60 wt. % (e.g., 60-69.9 wt. % and all values and ranges therebetween) of the refractory metal alloy includes rhenium, at least 30 wt. % (e.g., 30-39.9 wt. % and all values and ranges therebetween) of the refractory metal alloy includes chromium, and 0.1-10 wt. % (and all values and ranges therebetween) of the refractory metal alloy includes one or more of molybdenum, bismuth, niobium, tantalum, titanium, vanadium, tungsten, manganese, zirconium, technetium, ruthenium, rhodium, hafnium, osmium, copper, yttrium, zirconium, and/or iridium. In another non-limiting embodiment, at least 62 wt. % (e.g., 62-67.9 wt. % and all values and ranges therebetween) of the refractory metal alloy includes rhenium, at least 32 wt. % (e.g., 32-32.9 wt. % and all values and ranges therebetween) of the refractory metal alloy includes chromium, and 0.1-6 wt. % (and all values and ranges therebetween) of the refractory metal alloy includes one or more of molybdenum, bismuth, niobium, tantalum, titanium, vanadium, tungsten, manganese, zirconium, technetium, ruthenium, rhodium, hafnium, osmium, copper, yttrium, zirconium, and/or iridium.

In accordance with another and/or alternative non-limiting aspect of the present disclosure, the average grain size of the refractory metal alloy can be about 4-20 ASTM, the tensile elongation of the refractory metal alloy can be about 25-50%, the average density of the refractory metal alloy can be at least about 5 gm/cc, the average yield strength of the refractory metal alloy can be about 70-250 (ksi), the average ultimate tensile strength of the refractory metal alloy can be about 80-550 UTS (ksi), and an average Vickers hardness can be 234 DPH to 700 DPH or a Rockwell C hardness of 19-60 at 77° F.; however, this is not required.

In accordance with another and/or alternative non-limiting aspect of the present disclosure, the medical device is partially (e.g. 1-99.999 wt. % and all values and ranges therebetween) or fully formed of a metal material that includes a) stainless steel, b) CoCr alloy, c) TiAlV alloy, d) aluminum alloy, e) nickel alloy, f) titanium alloy, g) tungsten alloy, h) molybdenum alloy, i) copper alloy, j) beryllium-copper alloy, k) titanium-nickel alloy, l) refractory metal alloy, or m) metal alloy (e.g., stainless steel, CoCr alloy, TiAlV alloy, aluminum alloy, nickel alloy, titanium alloy, tungsten alloy, molybdenum alloy, copper alloy, beryllium-copper alloy, titanium-nickel alloy, refractory metal alloy, etc.) that includes at least 5 atomic weight percent (awt. %) or atomic percent (awt. %) rhenium (e.g., 5-99 awt. % rhenium and all values and ranges therebetween). As used herein, atomic weight percent (awt. %) or atomic percent (awt. %) or atomic percentage (awt. %) are used interchangeably. As defined herein, the weight percentage (wt. %) of an element is the weight of that element measured in the sample divided by the weight of all elements in the sample multiplied by 100. The atomic weight percent (awt. %) or atomic percent (awt. %) or atomic percentage (awt. %) is the number of atoms of that element, at that weight percentage, divided by the total number of atoms in the sample multiplied by 100. The use of the terms weight percentage (wt. %) and atomic weight percent (awt. %) or atomic percent (awt. %) or atomic percentage (awt. %) are two ways of referring to metallic alloy and its constituents. As defined herein, a stainless-steel alloy (SS alloy) includes at least 50 wt. % (weight percent) iron, 10-28 wt. % chromium, 0-35 wt. % nickel, and optionally one or more of 0-4 wt. % molybdenum, 0-2 wt. % manganese, 0-0.75 wt. % silicon, 0-0.3 wt. % carbon, 0-5 wt. % titanium, 0-10 wt. % niobium, 0-5 wt. % copper, 0-4 wt. % aluminum, 0-10 wt. % tantalum, 0-1 wt. % Se, 0-2 wt. % vanadium, and 0-2 wt. % tungsten. A 316L alloy that falls within a stainless-steel alloy includes 17-19 wt. % chromium, 13-15 wt. % nickel, 2-4 wt. % molybdenum, 2 wt. % max manganese, 0.75 wt. % max silicon, 0.03 wt. % max carbon, balance iron. As defined herein, a cobalt-chromium alloy (CoCr alloy) includes 30-68 wt. % cobalt, 15-32 wt. % chromium, and optionally one or more of 1-38 wt. % nickel, 2-18 wt. % molybdenum, 0-18 wt. % iron, 0-1 wt. % titanium, 0-0.15 wt. % manganese, 0-0.15 wt. % silver, 0-0.25 wt. % carbon, 0-16 wt. % tungsten, 0-2 wt. % silicon, 0-2 wt. % aluminum, 0-1 wt. % iron, 0-0.1 wt. % boron, 0-0.15 wt. % silver, and 0-2 wt. % titanium. As a MP35N alloy that falls within a CoCr alloy includes 18-22 wt. % chromium, 32-38 wt. % nickel, 8-12 wt. % molybdenum, 0-2 wt. % iron, 0-0.5 wt. % silicon, 0-0.5 wt. % manganese, 0-0.2 wt. % carbon, 0-2 wt. % titanium, 0-0.1 wt. %, 0-0.1 wt. % boron, 0-0.15 wt. % silver, and balance cobalt. As defined herein, a Phynox and Elgiloy alloy that falls within a CoCr alloy includes 38-42 wt. % cobalt, 18-22 wt. % chromium, 14-18 wt. % iron, 13-17 wt. % nickel, 6-8 wt. % molybdenum. As defined herein, a L605 alloy that falls within a CoCr alloy includes 18-22 wt. % chromium, 14-16 wt. % tungsten, 9-11 wt. % nickel, balance cobalt. As defined herein, a titanium-aluminum-vanadium alloy (TiAlV alloy) includes 4-8 wt. % aluminum, 3-6 wt. % vanadium, 80-93 wt. % titanium, and optionally one or more of 0-0.4 wt. % iron, 0-0.2 wt. % carbon, 0-0.5 wt. yttrium. A Ti-6Al-4V alloy that falls with a TiAlV alloy includes incudes 3.5-4.5 wt. % vanadium, 5.5-6.75 wt. % aluminum, 0.3 wt. % max iron, 0.08 wt. % max carbon, 0.05 wt. % max yttrium, balance titanium. As defined herein, an aluminum alloy includes 80-99 wt. % aluminum, and optionally one or more 0-12 wt. % silicon, 0-5 wt. % magnesium, 0-1 wt. % manganese, 0-0.5 wt. % scandium, 0-0.5 wt. % beryllium, 0-0.5 wt. % yttrium, 0-0.5 wt. % cerium, 0-0.5 wt. % chromium, 0-3 wt. % iron, 0-0.5, 0-9 wt. % zinc, 0-0.5 wt. % titanium, 0-3 wt. % lithium, 0-0.5 wt. % silver, 0-0.5 wt. % calcium, 0-0.5 wt. % zirconium, 0-1 wt. % lead, 0-0.5 wt. % cadmium, 0-0.05 wt. % bismuth, 0-1 wt. % nickel, 0-0.2 wt. % vanadium, 0-0.1 wt. % gallium, and 0-7 wt. % copper. As defined herein, a nickel alloy includes 30-98 wt. % nickel, and optionally one or more 5-25 wt. % chromium, 0-65 wt. % iron, 0-30 wt. % molybdenum, 0-32 wt. % copper, 0-32 wt. % cobalt, 2-2 wt. % aluminum, 0-6 wt. % tantalum, 0-15 wt. % tungsten, 0-5 wt. % titanium, 0-6 wt. % niobium, 0-3 wt. % silicon. As defined herein, a titanium alloy includes 80-99 wt. % titanium, and optionally one of more of 0-6 wt. % aluminum, 0-3 wt. % tin, 0-1 wt. % palladium, 0-8 wt. % vanadium, 0-15 wt. % molybdenum, 0-1 wt. % nickel, 0-0.3 wt. % ruthenium, 0-6 wt. % chromium, 0-4 wt. % zirconium, 0-4 wt. % niobium, 0-1 wt. % silicon, 0.0.5 wt. % cobalt, 0-2 wt. % iron. As defined herein, a tungsten alloy includes 85-98 wt. % tungsten, and optionally one or more of 0-8 wt. % nickel, 0-5 wt. % copper, 0-5 wt. % molybdenum, 0-4 wt. % iron. As defined herein, a molybdenum alloy includes 90-99.5 wt. % molybdenum, and optionally one or more of 0-1 wt. % nickel, 0-1 wt. % titanium, 0-1 wt. % zirconium, 0-30 wt. % tungsten, 0-2 wt. % hafnium, 0-2 wt. % lanthanum. As defined herein, a copper alloy includes 55-95 wt. % copper, and optionally one or more of 0-40 wt. % zinc, 0-10 wt. % tin, 0-10 wt. % lead, 0-1 wt. % iron, 0-5 wt. % silicon, 0-12 wt. % manganese, 0-12 wt. % aluminum, 0-3 wt. % beryllium, 0-1 wt. % cobalt, 0-20 wt. % nickel. As defined herein, a beryllium-copper alloy includes 95-98.5 wt. % copper, 1-4 wt. % beryllium, and optionally one or more of 0-1 wt. % cobalt, and 0-0.5 wt. % silicon. As defined herein, a titanium-nickel alloy (e.g., Nitinol alloy) includes 42-58 wt. % nickel and 42-58 wt. % titanium. As defined herein, a refractory metal alloy is a metal alloy that includes at least 20 wt. % of one or more of molybdenum, rhenium, niobium, tantalum or tungsten. Non-limiting refractory metal alloys include MoRe alloy, ReW alloy, MoReCr alloy, MoReTa alloy, MoReTi alloy, WCu alloy, ReCr, molybdenum alloy, rhenium alloy, tungsten alloy, tantalum alloy, niobium alloy, etc.

In accordance with another and/or alternative non-limiting aspect of the present disclosure, the medical device is partially or fully formed of a metal material that includes a metal alloy that contains at least 15 awt. % rhenium. It has been found that for several metal alloys the inclusion of at least 15 awt % rhenium results in the ductility and/or tensile strength of the metal alloy to improve as compared to a metal alloy is that absent rhenium. Such improvement in ductility and/or tensile strength due to the inclusion of at least 15 awt. % rhenium in the metal alloy is referred to as the "rhenium effect." As defined herein, a "rhenium effect" is a) an increase of at least 10% in ductility of the metal alloy caused by the addition of rhenium to the metal alloy, and/or b) an increase of at least 10% in tensile strength of the metal alloy caused by the addition of rhenium to the metal alloy. It has been found for some metal alloys (e.g., stainless steel, CoCr alloys, TiAlV alloys, aluminum alloys, nickel alloys, titanium alloys, tungsten alloys, molybdenum alloys, copper alloys, MP35N alloys, beryllium-copper alloys, etc.), the inclusion of at least 15 awt. % rhenium results in improved ductility and/or tensile strength. It has been found that the addition of rhenium to a metal alloy can result in the formation of a twining alloy in the metal alloy that results in the overall ductility of the metal alloy to increase as the yield and tensile strength increases as a result of reduction and/or work hardening of the metal alloy that includes the rhenium addition. The rhenium effect has been found to occur when the atomic weight of rhenium in the metal alloy is at least 15% (e.g., 15-99 awt. % rhenium in the metal alloy and all values and ranges therebetween). For example, for stainless-steel alloys, the rhenium effect can begin to be present when the stainless-steel alloy is modified to include a rhenium amount of at least 5-10 wt. % (and all values and ranges therebetween) of the stainless-steel alloy. For CoCr alloys, the rhenium effect can begin to be present when the CoCr alloy is modified to include a rhenium amount of at least 4.8-9.5 wt. % (and all values and ranges therebetween) of the CoCr alloy. For TiAlV alloys, the rhenium effect can begin to be present when the TiAlV alloy is modified to include a rhenium amount of at least 4.5-9 wt. % (and all values and ranges therebetween) of the TiAlV alloy. It can be appreciated, the rhenium content in the above non-limiting examples can be greater than the minimum amount to create the rhenium effect in the metal alloy.

In accordance with another and/or alternative aspect of the present disclosure, the metal alloy includes at least 5 awt. % (e.g., 5-99 awt. % and all values and ranges therebetween) rhenium, and at least 0.1 wt. % (e.g., 0.1 wt. % to 96 wt. % and all values and ranges therebetween) of one or more of aluminum, boron, beryllium, bismuth, cadmium, calcium, cerium, chromium, cobalt, copper, gallium, gold, hafnium, iridium, iron, lanthanum, lithium, magnesium, manganese, molybdenum, nickel, niobium, osmium, palladium, platinum, rare earth metals, rhodium, ruthenium, scandium, silver, silicon, tantalum, technetium, tin, titanium, tungsten, vanadium, yttrium, zinc, and/or zirconium, and the metal alloy optionally includes 0-2 wt. % (and all values and ranges therebetween) of a combination of other metals, carbon, oxygen, phosphorous, sulfur, hydrogen and/or nitrogen, and which metal alloy exhibits a rhenium effect. In another non-limiting embodiment, the metal alloy that is used to partially or fully form the medical device is a refractory metal alloy. In one non-limiting embodiment, the metal alloy that is used to partially or fully form the medical device is a stainless-steel alloy that has been modified to include at least 15 awt. % rhenium. In one non-limiting embodiment, the metal alloy that is used to partially or fully form the medical device is a cobalt chromium alloy that has been modified to include at least 15 awt. % rhenium. In one non-limiting embodiment, the metal alloy that is used to partially or fully form the medical device is a TiAlV alloy that has been modified to include at least 15 awt. % rhenium. In one non-limiting embodiment, the metal alloy that is used to partially or fully form the medical device is an aluminum alloy that has been modified to include at least 15 awt. % rhenium. In one non-limiting embodiment, the metal alloy that is used to partially or fully form the medical device is a nickel alloy that has been modified to include at least 15 awt. % rhenium. In one non-limiting embodiment, the metal alloy that is used to partially or fully form the medical device is a titanium alloy that has been modified to include at least 15 awt. % rhenium. In one non-limiting embodiment, the metal alloy that is used to partially or fully form the medical device is a tungsten alloy that has been modified to include at least 15 awt. % rhenium. In one non-limiting embodiment, the metal alloy that is used to partially or fully form the medical device is a molybdenum alloy that has been modified to include at least 15 awt. % rhenium. In one non-limiting embodiment, the metal alloy that is used to partially or fully form the medical device is a copper alloy that has been modified to include at least 15 awt. % rhenium. In one non-limiting embodiment, the metal alloy that is used to partially or fully form the medical device is a beryllium-copper alloy that has been modified to include at least 15 awt. % rhenium.

In accordance with another and/or alternative aspect of the present disclosure, the metal alloy that is used to partially or fully form the medical device includes rhenium and molybdenum, and the weight percent of rhenium in the metal alloy is greater that the weight percent of molybdenum in the metal alloy. In one non-limiting embodiment, the metal alloy includes rhenium and molybdenum, and the weight percent of rhenium in the metal alloy is greater that the weight percent of molybdenum in the metal alloy, and the weight percent of one or more of bismuth, niobium, tantalum, tungsten, titanium, vanadium, chromium, manganese, yttrium, zirconium, technetium, ruthenium, rhodium, hafnium, osmium, copper, and iridium in the metal alloy is greater that the weight percent of molybdenum in the metal alloy, and the metal alloy optionally includes 0-2 wt. % of a combination of other metals, carbon, oxygen, phosphorous, sulfur, hydrogen and/or nitrogen.

In accordance with another and/or alternative aspect of the present disclosure, the metal alloy that is used to partially or fully form the medical device includes rhenium and molybdenum, and the atomic weight percent of rhenium to the atomic weight percent of the combination of one or more of bismuth, niobium, tantalum, tungsten, titanium, vanadium, chromium, manganese, yttrium, zirconium, technetium, ruthenium, rhodium, hafnium, osmium, copper, and iridium is 0.4:1 to 2.5:1 (and all values and ranges therebetween).

In accordance with another and/or alternative aspect of the present disclosure, the metal alloy that is used to partially or fully form the medical device includes at least 5 awt. % (e.g., 5-99 awt. % and all values and ranges therebetween) rhenium plus at least two metals selected from the group of molybdenum, bismuth, chromium, iridium, niobium, tantalum, titanium, yttrium, and zirconium, and the content of the metal alloy that includes other elements and compounds is 0-0.1 wt. %. In another non-limiting embodiment, the metal alloy includes rhenium, molybdenum, and chromium. In another non-limiting embodiment, the metal alloy includes at least 35 wt. % (e.g., 35-75 wt. % and all values and ranges therebetween) rhenium, and the metal alloy also includes chromium. In one non-limiting embodiment, the metal alloy includes at least 35 wt. % rhenium and at least 25 wt. % (e.g., 25-49.9 wt. % and all values and ranges therebetween) of the metal alloy includes chromium, and optionally 0.1-40 wt. % (and all values and ranges therebetween) of the metal alloy includes one or more of aluminum, bismuth, calcium, carbon, cobalt, copper, gold, hafnium, iridium, iron, lanthanum, magnesium, manganese, molybdenum, nickel, niobium, osmium, platinum, rare earth metals, rhodium, ruthenium, silver, tantalum, technetium, titanium, tungsten, vanadium, yttrium, zinc, and/or zirconium, and optionally 0-2 wt. % of a combination of other metals, carbon, oxygen, phosphorous, sulfur, hydrogen and/or nitrogen. In another non-limiting embodiment, the metal alloy includes 15-50 awt. % rhenium (and all values and ranges therebetween) and 0.5-70 awt. % chromium (and all values and ranges therebetween). In another non-limiting embodiment, the metal alloy includes 15-50 awt. % rhenium (and all values and ranges therebetween) and 0.5-70 awt. % tantalum (and all values and ranges therebetween). In another non-limiting embodiment, the metal alloy includes 15-50 awt. % rhenium (and all values and ranges therebetween) and 0.5-70 awt. % niobium (and all values and ranges therebetween). In another non-limiting embodiment, the metal alloy includes 15-50 awt. % rhenium (and all values and ranges therebetween) and 0.5-70 awt. % titanium (and all values and ranges therebetween). In another non-limiting embodiment, the metal alloy includes 15-50 awt. % rhenium (and all values and ranges therebetween) and 0.5-70 awt. % zirconium (and all values and ranges therebetween). In another non-limiting embodiment, the metal alloy includes 15-50 awt. % rhenium (and all values and ranges therebetween) and 0.5-70 awt. % molybdenum (and all values and ranges therebetween). In another non-limiting embodiment, the metal alloy includes at least 15 awt. % rhenium, greater than 50 wt. % titanium (e.g., 51-80 wt. % and all values and ranges therebetween), 15-45 wt. % (and all values and ranges therebetween) niobium, 0-10 wt. % (and all values and ranges therebetween) zirconium, 0-15 wt. % (and all values and ranges therebetween) tantalum, and 0-8 wt. % molybdenum (and all values and ranges therebetween).

In accordance with another and/or alternative aspect of the present disclosure, the metal alloy that is used to partially or fully form the medical device includes at least 0.1 wt. % (e.g., 0.1-70 wt. % and all values and ranges therebetween) rhenium and one or more metals selected from the group of molybdenum, chromium, cobalt, nickel, titanium, tantalum, niobium, zirconium, and/or tungsten. In one non-limiting embodiment, the metal alloy that is used to partially or fully form the medical device includes at least 5 wt. % (e.g., 5-70 wt. % and all values and ranges therebetween) rhenium and one or more metals selected from the group of molybdenum, chromium, cobalt, nickel, titanium, tantalum, niobium, zirconium, and/or tungsten.

In accordance with another and/or alternative aspect of the present disclosure, the metal alloy that is used to partially or fully form the medical device is partially for fully formed of a refractory metal alloy, and wherein the refractory metal alloy includes at least 20 wt. % of one or more of niobium, tantalum or tungsten, and wherein the refractory metal alloy includes 0-30 wt. % molybdenum (and all values and ranges therebetween), and wherein the refractory metal alloy includes at least 5 awt. % rhenium (e.g., 5-80 awt. % rhenium and all values and ranges therebetween).

In accordance with another and/or alternative aspect of the present disclosure, the metal alloy that is used to partially or fully form the medical device is partially for fully formed of a metal alloy includes at least 5 awt. % rhenium (e.g., 5-99 awt. % rhenium and all values and ranges therebetween), and at least 0.1 wt. % of one or more additive metals selected from aluminum, bismuth, chromium, cobalt, copper, hafnium, iridium, iron, magnesium, manganese, nickel, niobium, osmium, rhodium, ruthenium, silicon, silver, tantalum, technetium, titanium, tungsten, vanadium, yttrium, and zirconium, and wherein the metal alloy includes 0-30 wt. % molybdenum (and all values and ranges therebetween), and wherein a combined weight percent of rhenium and the additive metals is 70-100 wt. % (and all values and ranges therebetween).

In accordance with another and/or alternative aspect of the present disclosure, the metal alloy that is used to partially or fully form the medical device is partially for fully formed of a metal alloy of stainless steel that has been modified with at least 5 awt. % rhenium (e.g., 5-50 awt. % rhenium and all values and ranges therebetween), and wherein a combined weight percent of iron, chromium, nickel, tantalum, niobium, copper, manganese, aluminum, titanium, selenium, vanadium, tungsten and rhenium is 70-100 wt. % (and all values and ranges therebetween).

In accordance with another and/or alternative aspect of the present disclosure, the metal alloy that is used to partially or fully form the medical device is partially for fully formed of a metal alloy of cobalt-chromium alloy that has been modified with at least 5 awt. % rhenium (e.g., 5-50 awt. % rhenium and all values and ranges therebetween), and wherein a combined weight percent of cobalt, chromium, nickel, iron, titanium, manganese, silver, tungsten, silicon, aluminum, iron, boron, silver, titanium, and rhenium is 70-100 wt. % (and all values and ranges therebetween).

In accordance with another and/or alternative aspect of the present disclosure, the metal alloy that is used to partially or fully form the medical device is partially for fully formed of a metal alloy of titanium-aluminum-vanadium alloy that has been modified with at least 5 awt. % rhenium (e.g., 5-50 awt. % rhenium and all values and ranges therebetween), and wherein a combined weight percent of aluminum, vanadium, titanium, iron, yttrium and rhenium is 70-100 wt. % (and all values and ranges therebetween).

In accordance with another and/or alternative aspect of the present disclosure, the metal alloy that is used to partially or fully form the medical device is partially for fully formed of a metal alloy of aluminum alloy that has been modified with at least 5 awt. % rhenium (e.g., 5-50 awt. % rhenium and all values and ranges therebetween), and wherein a combined weight percent of aluminum, silicon, magnesium, manganese, scandium, beryllium, yttrium, cerium, chromium, iron, zinc, titanium, lithium, silver, calcium, zirconium, cadmium, bismuth, nickel, vanadium, gallium, copper, and rhenium is 70-100 wt. % (and all values and ranges therebetween).

In accordance with another and/or alternative aspect of the present disclosure, the metal alloy that is used to partially or fully form the medical device is partially for fully formed of a metal alloy of nickel alloy that has been modified with at least 5 awt. % rhenium (e.g., 5-50 awt. % rhenium and all values and ranges therebetween), and wherein a combined weight percent of nickel, chromium, iron, copper, cobalt, aluminum, tantalum, tungsten, titanium, niobium, silicon, and rhenium is 70-100 wt. % (and all values and ranges therebetween).

In accordance with another and/or alternative aspect of the present disclosure, the metal alloy that is used to partially or fully form the medical device is partially for fully formed of a metal alloy of titanium alloy that has been modified with at least 5 awt. % rhenium (e.g., 5-50 awt. % rhenium and all values and ranges therebetween), and wherein a combined weight percent of titanium, aluminum, tin, palladium, vanadium, nickel, ruthenium, chromium, zirconium, niobium, silicon, cobalt, iron, and rhenium is 70-100 wt. % (and all values and ranges therebetween).

In accordance with another and/or alternative aspect of the present disclosure, the metal alloy that is used to partially or fully form the medical device is partially for fully formed of a metal alloy of tungsten alloy that has been modified with at least 5 awt. % rhenium (e.g., 5-50 awt. % rhenium and all values and ranges therebetween), and wherein a combined weight percent of tungsten, nickel, copper, iron, and rhenium is 70-100 wt. % (and all values and ranges therebetween).

In accordance with another and/or alternative aspect of the present disclosure, the metal alloy that is used to partially or fully form the medical device is partially for fully formed of a metal alloy of copper alloy that has been modified with at least 5 awt. % rhenium (e.g., 5-50 awt. % rhenium and all values and ranges therebetween), and wherein a combined weight percent of copper, zinc, tin, iron, silicon, manganese, aluminum, beryllium, cobalt, nickel, and rhenium is 70-100 wt. % (and all values and ranges therebetween).

In accordance with another and/or alternative aspect of the present disclosure, the metal alloy that is used to partially or fully form the medical device is partially for fully formed of a metal alloy of beryllium-copper alloy that has been modified with at least 5 awt. % rhenium (e.g., 5-50 awt. % rhenium and all values and ranges therebetween), and wherein a combined weight percent of copper, beryllium, cobalt, silicon, and rhenium is 70-100 wt. % (and all values and ranges therebetween).

In accordance with another and/or alternative aspect of the present disclosure, the metal alloy that is used to partially or fully form the medical device is partially for fully formed of a metal alloy of titanium-nickel alloy that has been modified with at least 5 awt. % rhenium (e.g., 5-50 awt. % rhenium and all values and ranges therebetween), and wherein a combined weight percent of nickel, titanium, and rhenium is 70-100 wt. % (and all values and ranges therebetween).

Several non-limiting examples of metal alloys that can be used to partially or fully form the medical device are set forth below in weight percent:

| Component/Wt. % | Ex. 1 | Ex. 2 | Ex. 3 | Ex. 4 |
|---|---|---|---|---|
| Al | 0-35% | 0-30% | 0-25% | 0-10% |
| Bi | 0-20% | 0-20% | 0-20% | 0-20% |
| Cr | 0-60% | 0-35% | 0-30% | 0-25% |
| Co | 0-60% | 0-50% | 0-40% | 0-20% |
| Mo | 0-95% | 0-80% | 0-55% | 0-30% |
| Nb | 0-80% | 0-80% | 0-50% | 0-20% |
| Ni | 0-60% | 0-55% | 0-40% | 0-20% |
| Re | 0.1-70% | 4.5-70% | 5-70% | 5-70% |
| Ta | 0-80% | 0-50% | 0-40% | 0-25% |
| Ti | 0-60% | 0-55% | 0-40% | 0-20% |
| V | 0-20% | 0-15% | 0-10% | 0-10% |
| W | 0-80% | 0-70% | 0-50% | 0-20% |
| Y | 0-20% | 0-15% | 0-10% | 0-10% |
| Zr | 0-20% | 0-15% | 0-10% | 0-10% |

| Component/Wt. % | Ex. 5 | Ex. 6 | Ex. 7 | Ex. 8 |
|---|---|---|---|---|
| Ag | 0-20% | 0-20% | 0-20% | 0-20% |
| Al | 0-35% | 0-30% | 5-30% | 0-25% |
| Bi | 0-20% | 0-20% | 0-20% | 0-20% |
| Cr | 10-40% | 0-40% | 0-40% | 0-40% |
| Cu | 0-20% | 0-20% | 0-20% | 0-20% |
| Co | 10-60% | 0-60% | 0-60% | 0-60% |
| Fe | 0-80% | 30-80% | 0-80% | 0-70% |
| Hf | 0-20% | 0-20% | 0-20% | 0-20% |
| Ir | 0-20% | 0-20% | 0-20% | 0-20% |
| Mg | 0-20% | 0-20% | 0-20% | 0-20% |
| Mn | 0-20% | 0-40% | 0-20% | 0-20% |
| Mo | 0-60% | 0-60% | 0-80% | 0-70% |
| Nb | 0-60% | 0-60% | 0-65% | 20-60% |
| Ni | 0-60% | 5-55% | 0-52% | 0-50% |
| Os | 0-20% | 0-20% | 0-20% | 0-20% |
| Pt | 0-20% | 0-20% | 0-20% | 0-20% |
| Re | 4.5-98% | 4.5-90% | 4.5-80% | 4.5-70% |
| Rh | 0-20% | 0-20% | 0-20% | 0-20% |
| Si | 0-20% | 0-20% | 0-20% | 0-20% |
| Sn | 0-20% | 0-20% | 0-20% | 0-20% |
| Ta | 0-60% | 0-60% | 5-65% | 0-60% |
| Tc | 0-20% | 0-20% | 0-20% | 0-20% |
| Ti | 0-60% | 0-55% | 0-53% | 0-50% |
| V | 0-20% | 0-20% | 2-20% | 0-20% |
| W | 0-60% | 0-60% | 0-80% | 0-70% |
| Y | 0-20% | 0-20% | 0-20% | 0-20% |
| Zr | 0-20% | 0-20% | 0-20% | 5-20% |

| Component/Wt. % | Ex. 9 | Ex. 10 | Ex. 11 | Ex. 12 |
|---|---|---|---|---|
| Ag | 0-5% | 0-5% | 0-5% | 0-5% |
| Al | 0-5% | 0-5% | 1-15% | 0-20% |
| Bi | 0-5% | 0-5% | 0-5% | 0-5% |
| Cr | 1-28% | 1-30% | 0-5% | 0-30% |
| Cu | 0-20% | 0-5% | 0-5% | 0-25% |
| Co | 0-5% | 1-60% | 0-5% | 0-60% |
| Fe | 10-80% | 0-25% | 0-5% | 0-80% |
| Hf | 0-5% | 0-5% | 0-5% | 0-5% |
| Ir | 0-5% | 0-5% | 0-5% | 0-5% |
| Mg | 0-5% | 0-5% | 0-5% | 0-5% |
| Mn | 0-5% | 0-5% | 0-5% | 0-5% |
| Mo | 0-8% | 0-25% | 0-5% | 0-98% |
| Nb | 0-5% | 0-5% | 0-5% | 0-95% |
| Ni | 1-20% | 1-45% | 0-5% | 0-50% |
| Os | 0-5% | 0-5% | 0-5% | 0-5% |
| Pt | 0-5% | 0-5% | 0-5% | 0-5% |
| Re | 5-20% | 4.8-20% | 4.5-20% | 4.5-20% |
| Rh | 0-5% | 0-5% | 0-5% | 0-5% |
| Si | 0-5% | 0-5% | 0-5% | 0-5% |
| Sn | 0-5% | 0-5% | 0-5% | 0-5% |
| Ta | 0-5% | 0-5% | 0-5% | 0-98% |
| Tc | 0-5% | 0-5% | 0-5% | 0-5% |
| Ti | 0-5% | 0-5% | 40-93% | 0-93% |
| V | 0-5% | 0-5% | 1-10% | 0-20% |

-continued

| | | | | |
|---|---|---|---|---|
| W | 0-5% | 0-20% | 0-5% | 0-98% |
| Y | 0-5% | 0-5% | 0-5% | 0-5% |
| Zr | 0-5% | 0-5% | 0-5% | 0-5% |

| Component/Wt. % | Ex. 13 | Ex. 14 | Ex. 15 | Ex. 16 |
|---|---|---|---|---|
| Mo | 40-80% | 40-80% | 40-80% | 40-80% |
| Co | ≤0.002% | ≤0.002% | ≤0.002% | ≤0.002% |
| Fe | ≤0.02% | ≤0.02% | ≤0.02% | ≤0.02% |
| Hf | 0.1-2.5% | 0-2.5% | 0-2.5% | 0-2.5% |
| Os | ≤1% | ≤1% | ≤1% | ≤1% |
| Nb | ≤0.01% | ≤0.01% | ≤0.01% | ≤0.01% |
| Pt | ≤1% | ≤1% | ≤1% | ≤1% |
| Re | 7-49% | 7.5-49% | 7.5-49% | 7.5-49% |
| Sn | ≤0.002% | ≤0.002% | ≤0.002% | ≤0.002% |
| Ta | 0-50% | 0-50% | 0-50% | 0-50% |
| Tc | ≤1% | ≤1% | ≤1% | ≤1% |
| Ti | ≤1% | ≤1% | ≤1% | ≤1% |
| V | ≤1% | ≤1% | ≤1% | ≤1% |
| W | 0-50% | 0-50% | 0-50% | 0.5-50% |
| Zr | ≤1% | ≤1% | ≤1% | ≤1% |

| Component/Wt. % | Ex. 17 | Ex. 18 | Ex. 19 |
|---|---|---|---|
| Mo | 40-80% | 40-80% | 40-80% |
| Co | ≤0.002% | ≤0.002% | ≤0.002% |
| Hf | 0-2.5% | 0-2.5% | 0-2.5% |
| Os | ≤1% | ≤1% | ≤1% |
| Nb | ≤0.01% | ≤0.01% | ≤0.01% |
| Pt | ≤1% | ≤1% | ≤1% |
| Re | 7-49% | 7.5-49% | 7.5-49% |
| Sn | ≤0.002% | ≤0.002% | ≤0.002% |
| Ta | 0-50% | 0.5-50% | 0-50% |
| Tc | ≤1% | ≤1% | ≤1% |
| Ti | ≤1% | ≤1% | ≤1% |
| V | ≤1% | ≤1% | ≤1% |
| W | 0-50% | 0-50% | 0-50% |

| Component/Wt. % | Ex. 20 | Ex. 21 | Ex. 22 |
|---|---|---|---|
| Mo | 45-78% | 45-75% | 45-70% |
| Co | ≤0.002% | ≤0.002% | ≤0.002% |
| Hf | 0-2.5% | 0-2.5% | 0-2.5% |
| Os | ≤1% | ≤1% | ≤1% |
| Nb | ≤0.01% | ≤0.01% | ≤0.01% |
| Pt | ≤1% | ≤1% | ≤1% |
| Re | 7-49% | 7.5-49% | 7.5-49% |
| Sn | ≤0.002% | ≤0.002% | ≤0.002% |
| Ta | 0-50% | 0.5-50% | 0-50% |
| Tc | ≤1% | ≤1% | ≤1% |
| Ti | ≤1% | ≤1% | ≤1% |
| V | ≤1% | ≤1% | ≤1% |
| W | 0-50% | 0-50% | 0-50% |

| Component/Wt. % | Ex. 23 | Ex. 24 | Ex. 25 | Ex. 26 |
|---|---|---|---|---|
| Mo | 35-80% | 35-80% | 35-70% | 35-65% |
| C | 0.05-0.15% | 0-0.15% | 0-0.15% | 0-0.15% |
| Hf | 0.8-1.4% | 0-2% | 0-2.5% | 0-2.5% |
| Re | 7-49% | 7-49% | 7.5-49% | 7.5-49% |
| Ta | 0-2% | 0-2% | 0-50% | 0-50% |
| W | 0-2% | 0-2% | 0-50% | 20-50% |

| Component/Wt. % | Ex. 27 | Ex. 28 | Ex. 29 |
|---|---|---|---|
| Mo | 40-60% | 35-60% | 30-60% |
| Hf | 0-2.5% | 0-2.5% | 0-2.5% |
| Re | 7-60% | 7.5-65% | 7.5-70% |
| Ta | 0-3% | 10-50% | 0-40% |
| W | 0-3% | 0-50% | 0-40% |

| Component/Wt. % | Ex. 30 | Ex. 31 | Ex. 32 |
|---|---|---|---|
| W | 20-80% | 60-80% | 20-78% |
| Re | 7.5-47.5% | 10-40% | 8-47.5% |
| Mo | 0-47.5% | <0.5% | 1-47.5% |
| Cu | <0.5% | <0.5% | <0.5% |
| Co | ≤0.002% | ≤0.002% | ≤0.002% |
| Fe | ≤0.02% | ≤0.02% | ≤0.02% |

-continued

| | | | |
|---|---|---|---|
| Hf | <0.5% | <0.5% | <0.5% |
| Os | <0.5% | <0.5% | <0.5% |
| Nb | ≤0.01% | ≤0.01% | ≤0.01% |
| Pt | <0.5% | <0.5% | <0.5% |
| Sn | ≤0.002% | ≤0.002% | ≤0.002% |
| Ta | <0.5% | <0.5% | <0.5% |
| Tc | <0.5% | <0.5% | <0.5% |
| Ti | <0.5% | <0.5% | <0.5% |
| V | <0.5% | <0.5% | <0.5% |
| Zr | <0.5% | <0.5% | <0.5% |

| Component/Wt. % | Ex. 33 | Ex. 34 | Ex. 35 |
|---|---|---|---|
| W | 20-80% | 60-80% | 20-75% |
| Re | 7.5-47.5% | 10-40% | 7.5-47.5% |
| Mo | 0-47.5% | <0.5% | 1-47.5% |

| Component/Wt. % | Ex. 36 | Ex. 37 | Ex. 38 |
|---|---|---|---|
| W | 50.1-80% | 65-80% | 50.1-79% |
| Re | 10-40% | 10-35% | 10-40% |
| Mo | 0-40% | <0.5% | 1-30% |

| Component/Wt. % | Ex. 39 | Ex. 40 | Ex. 41 |
|---|---|---|---|
| W | 20-49% | 20-49% | 20-49% |
| Re | 7.5-60% | 7.5-60% | 7.5-60% |
| Mo | 0-40% | 0-40% | 0-39% |

| Component/Wt. % | Ex. 42 | Ex. 43 | Ex. 44 |
|---|---|---|---|
| Re | 5-98% | 60-95% | 80-90% |
| Mo | 0-80% | 0-40% | 0-20% |
| W | 0-80% | 0-40% | 0-20% |

| Component/Wt. % | Ex. 45 | Ex. 46 | Ex. 47 |
|---|---|---|---|
| W | 20-49% | 20-49% | 20-49% |
| Re | 6-40% | 6-40% | 6-39% |
| Mo | 20-60% | 30-60% | 40-60% |

| Component/Wt. % | Ex. 48 | Ex. 49 | Ex. 50 |
|---|---|---|---|
| W | 20-40% | 20-35% | 20-30% |
| Re | 6-40% | 6-40% | 6-40% |
| Mo | 0-40% | 10-40% | 31-40% |

| Component/Wt. % | Ex. 51 | Ex. 52 | Ex. 53 | Ex. 54 |
|---|---|---|---|---|
| Re | 5-60% | 5-60% | 5-60% | 5-60% |
| Mo | 0-55% | 10-55% | 10-55% | 10-55% |
| Bi | 1-42 | 0-32 | 0-32 | 0-32 |
| Cr | 0-32 | 1-42 | 0-32 | 0-32 |
| Ir | 0-32 | 0-32 | 1-42 | 0-32 |
| Nb | 0-32 | 0-32 | 0-32 | 1-42 |
| Ta | 0-32 | 0-32 | 0-32 | 0-32 |
| Ti | 0-32 | 0-32 | 0-32 | 0-32 |
| Y | 0-32 | 0-32 | 0-32 | 0-32 |
| Zr | 0-32 | 0-32 | 0-32 | 0-32 |

| Component/Wt. % | Ex. 55 | Ex. 56 | Ex. 57 | Ex. 58 |
|---|---|---|---|---|
| Re | 5-60% | 5-60% | 5-60% | 5-60% |
| Mo | 15-55% | 15-55% | 15-55% | 15-55% |
| Bi | 0-32 | 0-32 | 0-32 | 0-32 |
| Cr | 0-32 | 0-32 | 0-32 | 0-32 |
| Ir | 0-32 | 0-32 | 0-32 | 0-32 |
| Nb | 0-32 | 0-32 | 0-32 | 0-32 |
| Ta | 1-42 | 0-32 | 0-32 | 0-32 |
| Ti | 0-32 | 1-42 | 0-32 | 0-32 |
| Y | 0-32 | 0-32 | 1-42 | 0-32 |
| Zr | 0-32 | 0-32 | 0-32 | 1-42 |

| Component/Wt. % | Ex. 59 | Ex. 60 | Ex. 61 | Ex. 62 |
|---|---|---|---|---|
| Re | 41-59% | 41-59% | 41-59% | 41-59% |
| Mo | 18-45% | 18-45% | 18-45% | 18-45% |
| Bi | 1-42 | 0-32 | 0-32 | 0-32 |
| Cr | 0-32 | 1-42 | 0-32 | 0-32 |

-continued

| | | | | |
|---|---|---|---|---|
| Ir | 0-32 | 0-32 | 1-42 | 0-32 |
| Nb | 0-32 | 0-32 | 0-32 | 1-42 |
| Ta | 0-32 | 0-32 | 0-32 | 0-32 |
| Ti | 0-32 | 0-32 | 0-32 | 0-32 |
| Y | 0-32 | 0-32 | 0-32 | 0-32 |
| Zr | 0-32 | 0-32 | 0-32 | 0-32 |

| Component/Wt. % | Ex. 63 | Ex. 64 | Ex. 65 | Ex. 66 |
|---|---|---|---|---|
| Re | 41-59% | 41-59% | 41-59% | 41-59% |
| Mo | 18-45% | 18-45% | 18-45% | 18-45% |
| Bi | 0-32 | 0-32 | 0-32 | 0-32 |
| Cr | 0-32 | 0-32 | 0-32 | 0-32 |
| Ir | 0-32 | 0-32 | 0-32 | 0-32 |
| Nb | 0-32 | 0-32 | 0-32 | 0-32 |
| Ta | 1-42 | 0-32 | 0-32 | 0-32 |
| Ti | 0-32 | 1-42 | 0-32 | 0-32 |
| Y | 0-32 | 0-32 | 1-42 | 0-32 |
| Zr | 0-32 | 0-32 | 0-32 | 1-42 |

| Component/Wt. % | Ex. 67 | Ex. 68 | Ex. 69 | Ex. 70 |
|---|---|---|---|---|
| Re | 41-59% | 41-59% | 41-59% | 41-59% |
| Mo | 18-45% | 18-45% | 18-45% | 18-45% |
| Bi | 0-15 | 0-15 | 1-36 | 0-15 |
| Cr | 1-20 | 1-20 | 1-20 | 1-20 |
| Ir | 0-15 | 0-15 | 0-15 | 0-15 |
| Nb | 1-36 | 0-15 | 0-15 | 0-15 |
| Ta | 0-15 | 1-36 | 0-15 | 0-15 |
| Ti | 0-15 | 0-15 | 0-15 | 0-15 |
| Y | 0-15 | 0-15 | 0-15 | 0-15 |
| Zr | 0-15 | 0-15 | 0-15 | 1-36 |

| Component/Wt. % | Ex. 71 | Ex. 72 | Ex. 73 | Ex. 74 |
|---|---|---|---|---|
| Re | 41-59% | 41-59% | 41-59% | 41-59% |
| Mo | 18-45% | 18-45% | 18-45% | 18-45% |
| Bi | 1-36 | 0-15 | 0-15 | 0-15 |
| Cr | 1-20 | 1-20 | 1-20 | 1-20 |
| Ir | 0-15 | 1-36 | 0-15 | 0-15 |
| Nb | 0-15 | 0-15 | 0-15 | 0-15 |
| Ta | 0-15 | 0-15 | 0-15 | 0-15 |
| Ti | 0-15 | 0-15 | 1-36 | 0-15 |
| Y | 0-15 | 0-15 | 0-15 | 1-36 |
| Zr | 0-15 | 0-15 | 0-15 | 0-15 |

| Component/Wt. % | Ex. 75 | Ex. 76 | Ex. 77 | Ex. 78 |
|---|---|---|---|---|
| Re | 41-59% | 41-59% | 41-59% | 41-59% |
| Mo | 18-45% | 18-45% | 18-45% | 18-45% |
| Bi | 1-34 | 0-15 | 0-15 | 0-15 |
| Cr | 0-15 | 0-15 | 0-15 | 0-15 |
| Ir | 0-15 | 0-15 | 0-15 | 1-34 |
| Nb | 3-27 | 3-27 | 3-27 | 3-27 |
| Ta | 0-42 | 1-34 | 0-15 | 0-15 |
| Ti | 0-15 | 0-15 | 0-15 | 0-15 |
| Y | 0-15 | 0-15 | 0-15 | 0-15 |
| Zr | 0-15 | 0-15 | 3-27 | 0-15 |

| Component/Wt. % | Ex. 79 | Ex. 80 | Ex. 81 | Ex. 82 |
|---|---|---|---|---|
| Re | 41-59% | 41-59% | 41-59% | 41-59% |
| Mo | 18-45% | 18-45% | 18-45% | 18-45% |
| Bi | 0-15 | 0-15 | 0-15 | 0-15 |
| Cr | 0-15 | 0-15 | 0-15 | 0-15 |
| Ir | 0-15 | 1-34 | 0-15 | 0-15 |
| Nb | 0-15 | 0-15 | 0-15 | 0-15 |
| Ta | 1-34 | 0-15 | 3-27 | 0-15 |
| Ti | 0-15 | 0-15 | 0-15 | 0-15 |
| Y | 0-15 | 0-15 | 0-15 | 3-27 |
| Zr | 3-27 | 3-27 | 3-27 | 3-27 |

| Component/Wt. % | Ex. 83 | Ex. 84 | Ex. 85 | Ex. 86 |
|---|---|---|---|---|
| Re | 41-59% | 41-59% | 41-59% | 41-59% |
| Mo | 18-45% | 18-45% | 18-45% | 18-45% |
| Bi | 0-15 | 0-15 | 0-15 | 0-15 |
| Cr | 0-15 | 0-15 | 0-15 | 1-10 |
| Ir | 1-34 | 0-25 | 3-27 | 0-15 |

-continued

| | | | | |
|---|---|---|---|---|
| Nb | 0-15 | 3-27 | 0-15 | 0-15 |
| Ta | 0-15 | 0-15 | 1-34 | 0-15 |
| Ti | 0-15 | 0-15 | 0-15 | 0-15 |
| Y | 3-27 | 3-27 | 0-15 | 0-15 |
| Zr | 0-15 | 0-15 | 3-27 | 1-12 |

| Component/Wt. % | Ex. 87 | Ex. 88 | Ex. 89 | Ex. 90 |
|---|---|---|---|---|
| Re | 50-75% | 55-75% | 60-75% | 65-75% |
| Cr | 25-50% | 25-45% | 25-40% | 25-35% |
| Mo | 0-25% | 0-25% | 0-25% | 0-25% |
| Bi | 0-25% | 0-25% | 0-25% | 0-25% |
| Ir | 0-25% | 0-25% | 0-25% | 0-25% |
| Nb | 0-25% | 0-25% | 0-25% | 0-25% |
| Ta | 0-25% | 0-25% | 0-25% | 0-25% |
| V | 0-25% | 0-25% | 0-25% | 0-25% |
| W | 0-25% | 0-25% | 0-25% | 0-25% |
| Mn | 0-25% | 0-25% | 0-25% | 0-25% |
| Tc | 0-25% | 0-25% | 0-25% | 0-25% |
| Ru | 0-25% | 0-25% | 0-25% | 0-25% |
| Rh | 0-25% | 0-25% | 0-25% | 0-25% |
| Hf | 0-25% | 0-25% | 0-25% | 0-25% |
| Os | 0-25% | 0-25% | 0-25% | 0-25% |
| Cu | 0-25% | 0-25% | 0-25% | 0-25% |
| Ir | 0-25% | 0-25% | 0-25% | 0-25% |
| Ti | 0-25% | 0-25% | 0-25% | 0-25% |
| Y | 0-25% | 0-25% | 0-25% | 0-25% |
| Zr | 0-25% | 0-25% | 0-25% | 0-25% |
| Ag | 0-25% | 0-25% | 0-25% | 0-25% |
| Al | 0-25% | 0-25% | 0-25% | 0-22% |
| Co | 0-25% | 0-25% | 0-25% | 0-25% |
| Fe | 0-25% | 0-25% | 0-25% | 0-25% |
| Mg | 0-25% | 0-25% | 0-25% | 0-25% |
| Ni | 0-25% | 0-25% | 0-25% | 0-25% |
| Pt | 0-25% | 0-25% | 0-25% | 0-25% |
| Si | 0-25% | 0-25% | 0-25% | 0-25% |
| Sn | 0-25% | 0-25% | 0-25% | 0-25% |

| Component/Wt. % | Ex. 91 | Ex. 92 | Ex. 93 | Ex. 94 |
|---|---|---|---|---|
| Re | 50-72% | 55-72% | 60-72% | 65-72% |
| Cr | 28-50% | 28-45% | 28-40% | 28-35% |
| Mo | 0-25% | 0-25% | 0-25% | 0-25% |
| Bi | 0-10% | 0-10% | 0-10% | 0-10% |
| Ir | 0-10% | 0-10% | 0-10% | 0-10% |
| Nb | 0-10% | 0-10% | 0-10% | 0-10% |
| Ta | 0-10% | 0-10% | 0-10% | 0-10% |
| V | 0-10% | 0-10% | 0-10% | 0-10% |
| W | 0-10% | 0-10% | 0-10% | 0-10% |
| Mn | 0-10% | 0-10% | 0-10% | 0-10% |
| Tc | 0-10% | 0-10% | 0-10% | 0-10% |
| Ru | 0-10% | 0-10% | 0-10% | 0-10% |
| Rh | 0-10% | 0-10% | 0-10% | 0-10% |
| Hf | 0-10% | 0-10% | 0-10% | 0-10% |
| Os | 0-10% | 0-10% | 0-10% | 0-10% |
| Cu | 0-10% | 0-10% | 0-10% | 0-10% |
| Ir | 0-10% | 0-10% | 0-10% | 0-10% |
| Ti | 0-10% | 0-10% | 0-10% | 0-10% |
| Y | 0-10% | 0-10% | 0-10% | 0-10% |
| Zr | 0-10% | 0-10% | 0-10% | 0-10% |
| Ag | 0-10% | 0-10% | 0-10% | 0-10% |
| Al | 0-10% | 0-10% | 0-10% | 0-10% |
| Co | 0-10% | 0-10% | 0-10% | 0-10% |
| Fe | 0-10% | 0-10% | 0-10% | 0-10% |
| Mg | 0-10% | 0-10% | 0-10% | 0-10% |
| Ni | 0-10% | 0-10% | 0-10% | 0-10% |
| Pt | 0-10% | 0-10% | 0-10% | 0-10% |
| Si | 0-10% | 0-10% | 0-10% | 0-10% |
| Sn | 0-10% | 0-10% | 0-10% | 0-10% |

| Component/Wt. % | Ex. 95 | Ex. 96 | Ex. 97 | Ex. 98 |
|---|---|---|---|---|
| Re | 50-70% | 55-70% | 60-70% | 65-70% |
| Cr | 30-50% | 30-45% | 30-40% | 30-35% |
| Mo | 0-10% | 0-10% | 0-10% | 0-10% |
| Bi | 0-10% | 0-10% | 0-10% | 0-10% |
| Ir | 0-10% | 0-10% | 0-10% | 0-10% |
| Nb | 0-10% | 0-10% | 0-10% | 0-10% |
| Ta | 0-10% | 0-10% | 0-10% | 0-10% |

-continued

| | | | | |
|---|---|---|---|---|
| V | 0-10% | 0-10% | 0-10% | 0-10% |
| W | 0-10% | 0-10% | 0-10% | 0-10% |
| Mn | 0-10% | 0-10% | 0-10% | 0-10% |
| Tc | 0-10% | 0-10% | 0-10% | 0-10% |
| Ru | 0-10% | 0-10% | 0-10% | 0-10% |
| Rh | 0-10% | 0-10% | 0-10% | 0-10% |
| Hf | 0-10% | 0-10% | 0-10% | 0-10% |
| Os | 0-10% | 0-10% | 0-10% | 0-10% |
| Cu | 0-10% | 0-10% | 0-10% | 0-10% |
| Ir | 0-10% | 0-10% | 0-10% | 0-10% |
| Ti | 0-10% | 0-10% | 0-10% | 0-10% |
| Y | 0-10% | 0-10% | 0-10% | 0-10% |
| Zr | 0-10% | 0-10% | 0-10% | 0-10% |
| Ag | 0-10% | 0-10% | 0-10% | 0-10% |
| Al | 0-10% | 0-10% | 0-10% | 0-10% |
| Co | 0-10% | 0-10% | 0-10% | 0-10% |
| Fe | 0-10% | 0-10% | 0-10% | 0-10% |
| Mg | 0-10% | 0-10% | 0-10% | 0-10% |
| Ni | 0-10% | 0-10% | 0-10% | 0-10% |
| Pt | 0-10% | 0-10% | 0-10% | 0-10% |
| Si | 0-10% | 0-10% | 0-10% | 0-10% |
| Sn | 0-10% | 0-10% | 0-10% | 0-10% |

| Component/Wt. % | Ex. 99 | Ex. 100 | Ex. 101 | Ex. 102 |
|---|---|---|---|---|
| Re | 50-67.5% | 55-67.5% | 60-67.5% | 65-67.5% |
| Cr | 32.5-50% | 32.5-45% | 32.5-40% | 32.5-35% |
| Mo | 0-10% | 0-10% | 0-10% | 0-10% |
| Bi | 0-10% | 0-10% | 0-10% | 0-10% |
| Ir | 0-10% | 0-10% | 0-10% | 0-10% |
| Nb | 0-10% | 0-10% | 0-10% | 0-10% |
| Ta | 0-10% | 0-10% | 0-10% | 0-10% |
| V | 0-10% | 0-10% | 0-10% | 0-10% |
| W | 0-10% | 0-10% | 0-10% | 0-10% |
| Mn | 0-10% | 0-10% | 0-10% | 0-10% |
| Tc | 0-10% | 0-10% | 0-10% | 0-10% |
| Ru | 0-10% | 0-10% | 0-10% | 0-10% |
| Rh | 0-10% | 0-10% | 0-10% | 0-10% |
| Hf | 0-10% | 0-10% | 0-10% | 0-10% |
| Os | 0-10% | 0-10% | 0-10% | 0-10% |
| Cu | 0-10% | 0-10% | 0-10% | 0-10% |
| Ir | 0-10% | 0-10% | 0-10% | 0-10% |
| Ti | 0-10% | 0-10% | 0-10% | 0-10% |
| Y | 0-10% | 0-10% | 0-10% | 0-10% |
| Zr | 0-10% | 0-10% | 0-10% | 0-10% |
| Ag | 0-10% | 0-10% | 0-10% | 0-10% |
| Al | 0-10% | 0-10% | 0-10% | 0-10% |
| Co | 0-10% | 0-10% | 0-10% | 0-10% |
| Fe | 0-10% | 0-10% | 0-10% | 0-10% |
| Mg | 0-10% | 0-10% | 0-10% | 0-10% |
| Ni | 0-10% | 0-10% | 0-10% | 0-10% |
| Pt | 0-10% | 0-10% | 0-10% | 0-10% |
| Si | 0-10% | 0-10% | 0-10% | 0-10% |
| Sn | 0-10% | 0-10% | 0-10% | 0-10% |

| Component/Wt. % | Ex. 103 | Ex. 104 | Ex. 105 | Ex. 106 |
|---|---|---|---|---|
| Re | 50-67.5% | 55-67.5% | 60-67.5% | 65-67.5% |
| Cr | 32.5-50% | 32.5-45% | 32.5-40% | 32.5-35% |
| Mo | 0-5% | 0-5% | 0-5% | 0-5% |
| Bi | 0-5% | 0-5% | 0-5% | 0-5% |
| Ir | 0-5% | 0-5% | 0-5% | 0-5% |
| Nb | 0-5% | 0-5% | 0-5% | 0-5% |
| Ta | 0-5% | 0-5% | 0-5% | 0-5% |
| V | 0-5% | 0-5% | 0-5% | 0-5% |
| W | 0-5% | 0-5% | 0-5% | 0-5% |
| Mn | 0-5% | 0-5% | 0-5% | 0-5% |
| Tc | 0-5% | 0-5% | 0-5% | 0-5% |
| Ru | 0-5% | 0-5% | 0-5% | 0-5% |
| Rh | 0-5% | 0-5% | 0-5% | 0-5% |
| Hf | 0-5% | 0-5% | 0-5% | 0-5% |
| Os | 0-5% | 0-5% | 0-5% | 0-5% |
| Cu | 0-5% | 0-5% | 0-5% | 0-5% |
| Ir | 0-5% | 0-5% | 0-5% | 0-5% |
| Ti | 0-5% | 0-5% | 0-5% | 0-5% |
| Y | 0-5% | 0-5% | 0-5% | 0-5% |
| Zr | 0-5% | 0-5% | 0-5% | 0-5% |
| Ag | 0-5% | 0-5% | 0-5% | 0-5% |
| Al | 0-5% | 0-5% | 0-5% | 0-5% |

-continued

| | | | | |
|---|---|---|---|---|
| Co | 0-5% | 0-5% | 0-5% | 0-5% |
| Fe | 0-5% | 0-5% | 0-5% | 0-5% |
| Mg | 0-5% | 0-5% | 0-5% | 0-5% |
| Ni | 0-5% | 0-5% | 0-5% | 0-5% |
| Pt | 0-5% | 0-5% | 0-5% | 0-5% |
| Si | 0-5% | 0-5% | 0-5% | 0-5% |
| Sn | 0-5% | 0-5% | 0-5% | 0-5% |

| Component/Wt. % | Ex. 107 | Ex. 108 | Ex. 109 | Ex. 110 |
|---|---|---|---|---|
| Re | 50-75% | 55-72% | 60-70% | 62-70% |
| Cr | 24-49% | 27-44% | 29-39% | 29-37% |
| Mo | 1-15% | 1-10% | 1-8% | 1-5% |
| Bi | 0-15% | 0-10% | 0-8% | 0-5% |
| Ir | 0-15% | 0-10% | 0-8% | 0-5% |
| Nb | 0-15% | 0-10% | 0-8% | 0-5% |
| Ta | 0-15% | 0-10% | 0-8% | 0-5% |
| V | 0-15% | 0-10% | 0-8% | 0-5% |
| W | 0-15% | 0-10% | 0-8% | 0-5% |
| Mn | 0-15% | 0-10% | 0-8% | 0-5% |
| Tc | 0-15% | 0-10% | 0-8% | 0-5% |
| Ru | 0-15% | 0-10% | 0-8% | 0-5% |
| Rh | 0-15% | 0-10% | 0-8% | 0-5% |
| Hf | 0-15% | 0-10% | 0-8% | 0-5% |
| Os | 0-15% | 0-10% | 0-8% | 0-5% |
| Cu | 0-15% | 0-10% | 0-8% | 0-5% |
| Ir | 0-15% | 0-10% | 0-8% | 0-5% |
| Ti | 0-15% | 0-10% | 0-8% | 0-5% |
| Y | 0-15% | 0-10% | 0-8% | 0-5% |
| Zr | 0-15% | 0-10% | 0-8% | 0-5% |
| Ag | 0-15% | 0-10% | 0-8% | 0-5% |
| Al | 0-15% | 0-10% | 0-8% | 0-5% |
| Co | 0-15% | 0-10% | 0-8% | 0-5% |
| Fe | 0-15% | 0-10% | 0-8% | 0-5% |
| Mg | 0-15% | 0-10% | 0-8% | 0-5% |
| Ni | 0-15% | 0-10% | 0-8% | 0-5% |
| Pt | 0-15% | 0-10% | 0-8% | 0-5% |
| Si | 0-15% | 0-10% | 0-8% | 0-5% |
| Sn | 0-15% | 0-10% | 0-8% | 0-5% |

| Component/Wt. % | Ex. 111 | Ex. 112 | Ex. 113 | Ex. 114 |
|---|---|---|---|---|
| Mo | 40-95% | 40-95% | 40-95% | 40-95% |
| Co | ≤0.002% | ≤0.002% | ≤0.002% | ≤0.002% |
| Fe | ≤0.02% | ≤0.02% | ≤0.02% | ≤0.02% |
| Hf | 0.1-2.5% | 0-2.5% | 0-2.5% | 0-2.5% |
| Os | ≤1% | ≤1% | ≤1% | ≤1% |
| Nb | ≤0.01% | ≤0.01% | ≤0.01% | ≤0.01% |
| Pt | ≤1% | ≤1% | ≤1% | ≤1% |
| Re | 5-40% | 5-40% | 5-40% | 5-40% |
| Sn | ≤0.002% | ≤0.002% | ≤0.002% | ≤0.002% |
| Ta | 0-50% | 0-50% | 0-50% | 0-50% |
| Tc | ≤1% | ≤1% | ≤1% | ≤1% |
| Ti | ≤1% | ≤1% | ≤1% | ≤1% |
| V | ≤1% | ≤1% | ≤1% | ≤1% |
| W | 0-50% | 0-50% | 0-50% | 0.5-50% |
| Zr | ≤1% | ≤1% | ≤1% | ≤1% |
| Ag | 0-5% | 0-5% | 0-5% | 0-5% |
| Al | 0-5% | 0-5% | 0-5% | 0-5% |
| Co | 0-5% | 0-5% | 0-5% | 0-5% |
| Mg | 0-5% | 0-5% | 0-5% | 0-5% |
| Ni | 0-5% | 0-5% | 0-5% | 0-5% |
| Si | 0-5% | 0-5% | 0-5% | 0-5% |
| Sn | 0-5% | 0-5% | 0-5% | 0-5% |

| Component/Wt. % | Ex. 115 | Ex. 116 | Ex. 117 |
|---|---|---|---|
| Mo | 40-95% | 40-95% | 40-95% |
| Co | ≤0.002% | ≤0.002% | ≤0.002% |
| Hf | 0-2.5% | 0-2.5% | 0-2.5% |
| Os | ≤1% | ≤1% | ≤1% |
| Nb | ≤0.01% | ≤0.01% | ≤0.01% |
| Pt | ≤1% | ≤1% | ≤1% |
| Re | 5-40% | 5-40% | 5-40% |
| Sn | ≤0.002% | ≤0.002% | ≤0.002% |
| Ta | 0-50% | 0.5-50% | 0-50% |
| Tc | ≤1% | ≤1% | ≤1% |
| Ti | ≤1% | ≤1% | ≤1% |
| V | ≤1% | ≤1% | ≤1% |

-continued

| | | | |
|---|---|---|---|
| W | 0-50% | 0-50% | 0-50% |
| Ag | 0-5% | 0-5% | 0-5% |
| Al | 0-5% | 0-5% | 0-5% |
| Fe | 0-5% | 0-5% | 0-5% |
| Mg | 0-5% | 0-5% | 0-5% |
| Ni | 0-5% | 0-5% | 0-5% |
| Si | 0-5% | 0-5% | 0-5% |

| Component/Wt. % | Ex. 118 | Ex. 119 | Ex. 120 |
|---|---|---|---|
| Mo | 60-95% | 60-95% | 60-90% |
| Co | ≤0.002% | ≤0.002% | ≤0.002% |
| Hf | 0-2.5% | 0-2.5% | 0-2.5% |
| Os | ≤1% | ≤1% | ≤1% |
| Nb | ≤0.01% | ≤0.01% | <0.01% |
| Pt | ≤1% | ≤1% | ≤1% |
| Re | 5-40% | 5-40% | 10-40% |
| Sn | ≤0.002% | ≤0.002% | ≤0.002% |
| Ta | 0-50% | 0.5-50% | 0-50% |
| Tc | ≤1% | ≤1% | ≤1% |
| Ti | ≤1% | ≤1% | ≤1% |
| V | ≤1% | ≤1% | ≤1% |
| W | 0-50% | 0-50% | 0-50% |
| Ag | 0-5% | 0-5% | 0-5% |
| Al | 0-5% | 0-5% | 0-5% |
| Fe | 0-5% | 0-5% | 0-5% |
| Mg | 0-5% | 0-5% | 0-5% |
| Ni | 0-5% | 0-5% | 0-5% |
| Si | 0-5% | 0-5% | 0-5% |

| Component/Wt. % | Ex. 121 | Ex. 122 | Ex. 123 | Ex. 124 |
|---|---|---|---|---|
| Mo | 60-95% | 60-95% | 50-95% | 40-80% |
| Hf | 0.8-1.4% | 0-2% | 0-2.5% | 0-2.5% |
| Re | 5-40% | 5-40% | 5-40% | 5-40% |
| Ta | 0-2% | 0-2% | 0-50% | 0-50% |
| W | 0-2% | 0-2% | 0-50% | 20-50% |

| Component/Wt. % | Ex. 125 | Ex. 126 | Ex. 127 |
|---|---|---|---|
| Mo | 97-95% | 50-90% | 60-95% |
| Hf | 0-2.5% | 0-2.5% | 0-2.5% |
| Re | 5-30 | 5-40% | 5-40% |
| Ta | 0-3% | 10-50% | 0-40% |
| W | 0-3% | 0-50% | 0-40% |

| Component/Wt. % | Ex. 128 | Ex. 129 | Ex. 130 |
|---|---|---|---|
| W | 20-95% | 60-95% | 20-80% |
| Re | 5-47.5% | 5-40% | 5-47.5% |
| Mo | 0-47.5% | <0.5% | 1-47.5% |
| Cu | <0.5% | <0.5% | <0.5% |
| Co | ≤0.002% | ≤0.002% | ≤0.002% |
| Fe | ≤0.02% | ≤0.02% | ≤0.02% |
| Hf | <0.5% | <0.5% | <0.5% |
| Os | <0.5% | <0.5% | <0.5% |
| Nb | ≤0.01% | ≤0.01% | ≤0.01% |
| Pt | <0.5% | <0.5% | <0.5% |
| Sn | ≤0.002% | ≤0.002% | ≤0.002% |
| Ta | <0.5% | <0.5% | <0.5% |
| Tc | <0.5% | <0.5% | <0.5% |
| Ti | <0.5% | <0.5% | <0.5% |
| V | <0.5% | <0.5% | <0.5% |
| Zr | <0.5% | <0.5% | <0.5% |
| Ag | 0-5% | 0-5% | 0-5% |
| Al | 0-5% | 0-5% | 0-5% |
| Fe | 0-5% | 0-5% | 0-5% |
| Mg | 0-5% | 0-5% | 0-5% |
| Ni | 0-5% | 0-5% | 0-5% |
| Si | 0-5% | 0-5% | 0-5% |

| Component/Wt. % | Ex. 131 | Ex. 132 | Ex. 133 | Ex. 134 |
|---|---|---|---|---|
| W | 1-94.9% | 1-94.9% | 1-94.9% | 10-95% |
| Cu | 0.1-94% | 0.1-94% | 0.1-94% | 1-84% |
| Co | ≤0.002% | ≤0.002% | ≤0.002% | ≤0.002% |
| Fe | ≤0.02% | ≤0.02% | ≤0.02% | ≤0.02% |
| Hf | 0.1-2.5% | 0-2.5% | 0-2.5% | 0-2.5% |
| Os | ≤1% | ≤1% | ≤1% | ≤1% |

-continued

| | | | | |
|---|---|---|---|---|
| Mo | 0-5% | 0.1-3% | 0-2% | 0-3% |
| Nb | ≤0.01% | <0.01% | ≤0.01% | ≤0.01% |
| Pt | ≤1% | ≤1% | ≤1% | ≤1% |
| Re | 5-40% | 5-40% | 5-40% | 6-40% |
| Sn | ≤0.002% | ≤0.002% | ≤0.002% | ≤0.002% |
| Ta | 0-50% | 0-50% | 0-50% | 0-50% |
| Tc | ≤1% | ≤1% | ≤1% | ≤1% |
| Ti | ≤1% | ≤1% | ≤1% | ≤1% |
| V | ≤1% | ≤1% | ≤1% | ≤1% |
| Zr | ≤1% | ≤1% | ≤1% | ≤1% |
| Ag | 0-5% | 0-5% | 0-5% | 0-5% |
| Al | 0-5% | 0-5% | 0-5% | 0-5% |
| Fe | 0-5% | 0-5% | 0-5% | 0-5% |
| Mg | 0-5% | 0-5% | 0-5% | 0-5% |
| Ni | 0-5% | 0-5% | 0-5% | 0-5% |
| Si | 0-5% | 0-5% | 0-5% | 0-5% |

| Component/Wt. % | Ex. 135 | Ex. 136 | Ex. 137 |
|---|---|---|---|
| W | 20-96% | 25-92% | 30-88% |
| Cu | 2-74% | 2-68% | 5-62% |
| Co | ≤0.002% | ≤0.002% | ≤0.002% |
| Hf | 0-2.5% | 0-2.5% | 0-2.5% |
| Os | ≤1% | ≤1% | ≤1% |
| Mo | 0-3% | 0-2% | 0-1% |
| Nb | ≤0.01% | ≤0.01% | ≤0.01% |
| Pt | ≤1% | ≤1% | ≤1% |
| Re | 6-40% | 7-40% | 8-40% |
| Sn | ≤0.002% | ≤0.002% | ≤0.002% |
| Ta | 0-50% | 0.5-50% | 0-50% |
| Tc | ≤1% | ≤1% | ≤1% |
| Ti | ≤1% | ≤1% | ≤1% |
| V | ≤1% | ≤1% | ≤1% |
| Ag | 0-5% | 0-5% | 0-5% |
| Al | 0-5% | 0-5% | 0-5% |
| Fe | 0-5% | 0-5% | 0-5% |
| Mg | 0-5% | 0-5% | 0-5% |
| Ni | 0-5% | 0-5% | 0-5% |
| Si | 0-5% | 0-5% | 0-5% |

| Component/Wt. % | Ex. 138 | Ex. 139 | Ex. 140 | Ex. 141 |
|---|---|---|---|---|
| W | 25-88% | 35-87% | 40-86% | 50-80% |
| Cu | 5-68% | 5-57% | 5-51% | 5-40% |
| Hf | 0.8-1.4% | 0-2.5% | 0-2.5% | 0-2.5% |
| Re | 0-40% | 0-40% | 0-40% | 0-40% |
| Ta | 0-50% | 0-50% | 0-50% | 0-50% |

| Component/Wt. % | Ex. 142 | Ex. 143 | Ex. 144 |
|---|---|---|---|
| W | 55-88% | 60-87% | 70-86% |
| Cu | 1-34% | 1-28% | 1-17% |
| C | 0-0.15% | 0-0.15% | 0-0.15% |
| Hf | 0-2.5% | 0-2.5% | 0-2.5% |
| Re | 11-40% | 12-40% | 13-40% |
| Ta | 0-50% | 10-50% | 0-50% |
| W | 0-50% | 0-50% | 0-50% |

| Component/Wt. % | Ex. 145 | Ex. 146 | Ex. 147 |
|---|---|---|---|
| Ti | 55-66% | 65-76% | 70-76% |
| Mo | 20-41% | 20-31% | 20-26% |
| Re | 4-20% | 4-20% | 4-20% |
| Yt | <0.5% | <0.5% | <0.5% |
| Nb | <0.5% | <0.5% | <0.5% |
| Co | <0.5% | <0.5% | <0.5% |
| Cr | <0.5% | <0.5% | <0.5% |
| Zr | <0.5% | <0.5% | <0.5% |

| Component/Wt. % | Ex. 148 | Ex. 149 | Ex. 150 |
|---|---|---|---|
| W | 20-95% | 60-85% | 20-84% |
| Re | 5-47.5% | 15-40% | 5-47.5% |
| Mo | 0-47.5% | <0.5% | 1-47.5% |

-continued

| Component/Wt. % | Ex. 151 | Ex. 152 | Ex. 153 |
|---|---|---|---|
| W | 50.1-93% | 65-92% | 70-90% |
| Re | 7-40% | 8-35% | 9-30% |
| Mo | 0-40% | <0.5% | 1-30% |

| Component/Wt. % | Ex. 154 | Ex. 155 | Ex. 156 |
|---|---|---|---|
| W | 20-49% | 20-49% | 20-49% |
| Re | 5-40% | 5-40% | 5-39% |
| Mo | 20-60% | 30-60% | 40-60% |

| Component/Wt. % | Ex. 157 | Ex. 158 | Ex. 159 |
|---|---|---|---|
| W | 20-40% | 20-35% | 20-30% |
| Re | 7-40% | 10-40% | 25-40% |
| Mo | 0-40% | 10-40% | 25-40% |

| Component/Wt. % | Ex. 160 | Ex. 161 | Ex. 162 |
|---|---|---|---|
| W | 20-95% | 60-93% | 20-80% |
| Re | 5-47.5% | 7-40% | 5-47.5% |
| Mo | 0-47.5% | <0.5% | 1-47.5% |
| Cu | <0.5% | <0.5% | <0.5% |
| Co | ≤0.002% | ≤0.002% | ≤0.002% |
| Fe | ≤0.02% | ≤0.02% | ≤0.02% |
| Hf | <0.5% | <0.5% | <0.5% |
| Os | <0.5% | <0.5% | <0.5% |
| Nb | ≤0.01% | ≤0.01% | ≤0.01% |
| Pt | <0.5% | <0.5% | <0.5% |
| Sn | ≤0.002% | ≤0.002% | ≤0.002% |
| Ta | <0.5% | <0.5% | <0.5% |
| Tc | <0.5% | <0.5% | <0.5% |
| Ti | <0.5% | <0.5% | <0.5% |
| V | <0.5% | <0.5% | <0.5% |
| Zr | <0.5% | <0.5% | <0.5% |
| Ag | 0-5% | 0-5% | 0-5% |
| Al | 0-5% | 0-5% | 0-5% |
| Fe | 0-5% | 0-5% | 0-5% |
| Mg | 0-5% | 0-5% | 0-5% |
| Ni | 0-5% | 0-5% | 0-5% |
| Si | 0-5% | 0-5% | 0-5% |

| Component/Wt. % | Ex. 163 | Ex. 164 | Ex. 165 | Ex. 166 |
|---|---|---|---|---|
| Ag | 0-10% | 0-10% | 0-10% | 0-10% |
| Al | 0-10% | 0-10% | 0-10% | 2-10% |
| B | 0-10% | 0-10% | 0-10% | 0-10% |
| Bi | 0-10% | 0-10% | 0-10% | 0-10% |
| Cr | 2-30% | 10-30% | 0-20% | 0-20% |
| Cu | 0-10% | 0-10% | 0-10% | 0-10% |
| Co | 0-10% | 32-70% | 0-10% | 0-10% |
| Fe | 50-80% | 0-20% | 0-10% | 0-10% |
| Hf | 0-10% | 0-10% | 0-10% | 0-10% |
| Ir | 0-10% | 0-10% | 0-10% | 0-10% |
| La | 0-10% | 0-10% | 0-10% | 0-10% |
| Mg | 0-10% | 0-10% | 0-10% | 0-10% |
| Mn | 0-20% | 0-10% | 0-10% | 0-10% |
| Mo | 0-10% | 0-30% | 0-16% | 0-16% |
| Nb | 0-10% | 0-10% | 0-10% | 0-10% |
| Ni | 0.1-30% | 0.1-40% | 0-10% | 0-10% |
| Os | 0-10% | 0-10% | 0-10% | 0-10% |
| Pt | 0-10% | 0-10% | 0-10% | 0-10% |
| Re | 5-40% | 4.8-40% | 4.5-80% | 4.5-80% |
| Rh | 0-10% | 0-10% | 0-10% | 0-10% |
| Se | 0-10% | 0-10% | 0-10% | 0-10% |
| Si | 0-10% | 0-10% | 0-10% | 0-10% |
| Sn | 0-10% | 0-10% | 0-12% | 0-12% |
| Ta | 0-10% | 0-10% | 0-10% | 0-10% |
| Tc | 0-10% | 0-10% | 0-10% | 0-10% |
| Ti | 0-10% | 0-10% | 70-91.5% | 70-91.5% |
| V | 0-10% | 0-10% | 0-10% | 0.01-10% |
| W | 0-10% | 0-20% | 0-10% | 0-10% |
| Y | 0-10% | 0-10% | 0-10% | 0-10% |
| Zr | 0-10% | 0-10% | 0-10% | 0-10% |

-continued

| Component/Wt. % | Ex. 167 | Ex. 168 | Ex. 169 | Ex. 170 |
|---|---|---|---|---|
| Ag | 0-10% | 0-10% | 0-10% | 0-10% |
| Al | 0-10% | 0-10% | 0-10% | 0-10% |
| B | 0-10% | 0-10% | 0-10% | 0-10% |
| Bi | 0-10% | 0-10% | 0-10% | 0-10% |
| Cr | 0-10% | 0-20% | 0-20% | 0-10% |
| Cu | 0-10% | 0-10% | 0-50% | 0-10% |
| Co | 0-10% | 0-10% | 0-10% | 0-10% |
| Fe | 0-10% | 0-10% | 0-10% | 0-10% |
| Hf | 0-10% | 0-10% | 0-10% | 0-10% |
| Ir | 0-10% | 0-10% | 0-10% | 0-12% |
| La | 0-10% | 0-10% | 0-10% | 0-10% |
| Mg | 0-10% | 0-10% | 0-10% | 0-10% |
| Mn | 0-10% | 0-10% | 0-10% | 0-10% |
| Mo | 0-55% | 40-93% | 0-50% | 0-20% |
| Nb | 0-10% | 0-10% | 0-10% | 40-85% |
| Ni | 0-45% | 0-10% | 0-10% | 0-10% |
| Os | 0-10% | 0-10% | 0-10% | 0-10% |
| Pt | 0-10% | 0-10% | 0-10% | 0-10% |
| Re | 14-40% | 7-40% | 7-40% | 7-40% |
| Rh | 0-10% | 0-10% | 0-10% | 0-10% |
| Se | 0-10% | 0-10% | 0-10% | 0-10% |
| Si | 0-10% | 0-10% | 0-10% | 0-10% |
| Sn | 0-10% | 0-10% | 0-10% | 0-10% |
| Ta | 35-84% | 0-50% | 0-50% | 0-35% |
| Tc | 0-10% | 0-10% | 0-10% | 0-10% |
| Ti | 0-10% | 0-10% | 0-10% | 0-10% |
| V | 0-10% | 0-10% | 0-10% | 0-10% |
| W | 0.1-25% | 0-50% | 14-10% | 0-15% |
| Y | 0-10% | 0-10% | 0-10% | 0-10% |
| Zr | 0-10% | 0-10% | 0-50% | 0-10% |

| Component/Wt. % | Ex. 171 | Ex. 172 | Ex. 173 | Ex. 174 |
|---|---|---|---|---|
| Ag | 0-10% | 0-10% | 0-5% | 0-5% |
| Al | 0-10% | 0-10% | 0-5% | 5-7% |
| B | 0-10% | 0-10% | 0-5% | 0-5% |
| Bi | 0-10% | 0-10% | 0-5% | 0-5% |
| Cr | 0-10% | 1-95% | 12-28% | 0-5% |
| Cu | 0-10% | 0-10% | 0-5% | 0-5% |
| Co | 0-10% | 0-10% | 36-68% | 0-5% |
| Fe | 0-10% | 0-10% | 0-18% | 0-5% |
| Hf | 0-10% | 0-10% | 0-5% | 0-5% |
| Ir | 0-10% | 0-10% | 0-5% | 0-5% |
| La | 0-10% | 0-10% | 0-5% | 0-5% |
| Mg | 0-10% | 0-10% | 0-5% | 0-5% |
| Mn | 0-10% | 0-10% | 0-5% | 0-5% |
| Mo | 0-10% | 0-20% | 0-12% | 0-5% |
| Nb | 0-10% | 0-10% | 0-5% | 0-5% |
| Ni | 30-58% | 0-10% | 9-36% | 0-5% |
| Os | 0-10% | 0-10% | 0-5% | 0-5% |
| Pt | 0-10% | 0-10% | 0-5% | 0-5% |
| Re | 5-40% | 5-40% | 4.8-40% | 4.5-40% |
| Rh | 0-10% | 0-10% | 0-5% | 0-5% |
| Se | 0-10% | 0-10% | 0-5% | 0-5% |
| Si | 0-10% | 0-10% | 0-5% | 0-5% |
| Sn | 0-10% | 0-10% | 0-5% | 0-5% |
| Ta | 0-10% | 0-10% | 0-5% | 0-5% |
| Tc | 0-10% | 0-10% | 0-5% | 0-5% |
| Ti | 30-58% | 0-40% | 0-5% | 70-91.5% |
| V | 0-10% | 0-10% | 0-5% | 3-6% |
| W | 0-10% | 0-10% | 0-16% | 0-5% |
| Y | 0-10% | 0-10% | 0-5% | 0-5% |
| Zr | 0-10% | 0-20% | 0-5% | 0-5% |

| Component/Wt. % | Ex. 175 | Ex. 176 | Ex. 177 | Ex. 178 |
|---|---|---|---|---|
| Ag | 0-8% | 0-8% | 0-8% | 0-8% |
| Al | 0-8% | 0-8% | 0-8% | 2-10% |
| B | 0-8% | 0-8% | 0-8% | 0-8% |
| Bi | 0-8% | 0-8% | 0-8% | 0-8% |
| Cr | 2-30% | 10-30% | 0-20% | 0-20% |
| Cu | 0-8% | 0-8% | 0-8% | 0-8% |
| Co | 0-8% | 32-70% | 0-8% | 0-8% |
| Fe | 50-80% | 0-20% | 0-8% | 0-8% |
| Hf | 0-8% | 0-8% | 0-8% | 0-8% |
| Ir | 0-8% | 0-8% | 0-8% | 0-8% |
| La | 0-8% | 0-8% | 0-8% | 0-8% |

-continued

| | | | | |
|---|---|---|---|---|
| Mg | 0-8% | 0-8% | 0-8% | 0-8% |
| Mn | 0-20% | 0-8% | 0-8% | 0-8% |
| Mo | 0-8% | 0-30% | 0-16% | 0-16% |
| Nb | 0-8% | 0-8% | 0-8% | 0-8% |
| Ni | 0.1-30% | 0.1-40% | 0-8% | 0-8% |
| Os | 0-8% | 0-8% | 0-8% | 0-8% |
| Pt | 0-8% | 0-8% | 0-8% | 0-8% |
| Re | 5-40% | 4.8-40% | 4.5-80% | 4.5-80% |
| Rh | 0-8% | 0-8% | 0-8% | 0-8% |
| Se | 0-8% | 0-8% | 0-8% | 0-8% |
| Si | 0-8% | 0-8% | 0-8% | 0-8% |
| Sn | 0-8% | 0-8% | 0-12% | 0-12% |
| Ta | 0-8% | 0-8% | 0-8% | 0-8% |
| Tc | 0-8% | 0-8% | 0-8% | 0-8% |
| Ti | 0-8% | 0-8% | 70-91.5% | 70-91.5% |
| V | 0-8% | 0-8% | 0-8% | 0.01-10% |
| W | 0-8% | 0-20% | 0-8% | 0-8% |
| Y | 0-8% | 0-8% | 0-8% | 0-8% |
| Zr | 0-8% | 0-8% | 0-8% | 0-8% |

| Component/Wt. % | Ex. 179 | Ex. 180 | Ex. 181 | Ex. 182 |
|---|---|---|---|---|
| Ag | 0-8% | 0-8% | 0-8% | 0-8% |
| Al | 0-8% | 0-8% | 0-8% | 0-8% |
| B | 0-8% | 0-8% | 0-8% | 0-8% |
| Bi | 0-8% | 0-8% | 0-8% | 0-8% |
| Cr | 0-8% | 0-20% | 0-20% | 0-8% |
| Cu | 0-8% | 0-8% | 0-50% | 0-8% |
| Co | 0-8% | 0-8% | 0-8% | 0-8% |
| Fe | 0-8% | 0-8% | 0-8% | 0-8% |
| Hf | 0-8% | 0-8% | 0-8% | 0-8% |
| Ir | 0-8% | 0-8% | 0-8% | 0-12% |
| La | 0-8% | 0-8% | 0-8% | 0-8% |
| Mg | 0-8% | 0-8% | 0-8% | 0-8% |
| Mn | 0-8% | 0-8% | 0-8% | 0-8% |
| Mo | 0-55% | 40-93% | 0-50% | 0-20% |
| Nb | 0-8% | 0-8% | 0-8% | 40-85% |
| Ni | 0-45% | 0-8% | 0-8% | 0-8% |
| Os | 0-8% | 0-8% | 0-8% | 0-8% |
| Pt | 0-8% | 0-8% | 0-8% | 0-8% |
| Re | 14-40% | 7-40% | 7-40% | 7-40% |
| Rh | 0-8% | 0-8% | 0-8% | 0-8% |
| Se | 0-8% | 0-8% | 0-8% | 0-8% |
| Si | 0-8% | 0-8% | 0-8% | 0-8% |
| Sn | 0-8% | 0-8% | 0-8% | 0-8% |
| Ta | 35-84% | 0-50% | 0-50% | 0-35% |
| Tc | 0-8% | 0-8% | 0-8% | 0-8% |
| Ti | 0-8% | 0-8% | 0-8% | 0-8% |
| V | 0-8% | 0-8% | 0-8% | 0-8% |
| W | 0.1-25% | 0-50% | 14-10% | 0-15% |
| Y | 0-8% | 0-8% | 0-8% | 0-8% |
| Zr | 0-8% | 0-8% | 0-50% | 0-8% |

| Component/Wt. % | Ex. 183 | Ex. 184 | Ex. 185 | Ex. 186 |
|---|---|---|---|---|
| Ag | 0-5% | 0-5% | 0-5% | 0-5% |
| Al | 0-5% | 0-5% | 0-5% | 5-7% |
| B | 0-5% | 0-5% | 0-5% | 0-5% |
| Bi | 0-5% | 0-5% | 0-5% | 0-5% |
| Cr | 0-5% | 1-95% | 12-28% | 0-5% |
| Cu | 0-5% | 0-5% | 0-5% | 0-5% |
| Co | 0-5% | 0-5% | 36-68% | 0-5% |
| Fe | 0-5% | 0-5% | 0-18% | 0-5% |
| Hf | 0-5% | 0-5% | 0-5% | 0-5% |
| Ir | 0-5% | 0-5% | 0-5% | 0-5% |
| La | 0-5% | 0-5% | 0-5% | 0-5% |
| Mg | 0-5% | 0-5% | 0-5% | 0-5% |
| Mn | 0-5% | 0-5% | 0-5% | 0-5% |
| Mo | 0-5% | 0-20% | 0-12% | 0-5% |
| Nb | 0-5% | 0-5% | 0-5% | 0-5% |
| Ni | 30-58% | 0-5% | 9-36% | 0-5% |
| Os | 0-5% | 0-5% | 0-5% | 0-5% |
| Pt | 0-5% | 0-5% | 0-5% | 0-5% |
| Re | 5-40% | 5-40% | 4.8-40% | 4.5-40% |
| Rh | 0-5% | 0-5% | 0-5% | 0-5% |
| Se | 0-5% | 0-5% | 0-5% | 0-5% |
| Si | 0-5% | 0-5% | 0-5% | 0-5% |
| Sn | 0-5% | 0-5% | 0-5% | 0-5% |
| Ta | 0-5% | 0-5% | 0-5% | 0-5% |

| | | | | |
|---|---|---|---|---|
| Tc | 0-5% | 0-5% | 0-5% | 0-5% |
| Ti | 30-58% | 0-40% | 0-5% | 70-91.5% |
| V | 0-5% | 0-5% | 0-5% | 3-6% |
| W | 0-5% | 0-5% | 0-16% | 0-5% |
| Y | 0-5% | 0-5% | 0-5% | 0-5% |
| Zr | 0-5% | 0-20% | 0-5% | 0-5% |

| Component/Wt. % | Ex. 187 | Ex. 188 | Ex. 189 | Ex. 190 |
|---|---|---|---|---|
| Ag | 0-5% | 0-5% | 0-5% | 0-5% |
| Al | 0-5% | 0-5% | 0-5% | 0-5% |
| B | 0-5% | 0-5% | 0-5% | 0-5% |
| Bi | 0-5% | 0-5% | 0-5% | 0-5% |
| Cr | 0-5% | 0-5% | 0-5% | 0-5% |
| Cu | 0-5% | 0-5% | 0-5% | 0-5% |
| Co | 0-5% | 0-5% | 0-5% | 0-5% |
| Fe | 0-5% | 0-5% | 0-5% | 0-5% |
| Hf | 0-5% | 0-5% | 0-5% | 0-5% |
| Ir | 0-5% | 0-5% | 0-5% | 0-5% |
| La | 0-5% | 0-5% | 0-5% | 0-5% |
| Mg | 0-5% | 0-5% | 0-5% | 0-5% |
| Mn | 0-5% | 0-5% | 0-5% | 0-5% |
| Mo | 1-15% | 2-10% | 3-8% | 0-5% |
| Nb | 0-5% | 0-5% | 0-5% | 20-45% |
| Ni | 0-5% | 0-5% | 0-5% | 0-5% |
| Os | 0-5% | 0-5% | 0-5% | 0-5% |
| Pt | 0-5% | 0-5% | 0-5% | 0-5% |
| Re | 0-5% | 0-5% | 0-5% | 0-5% |
| Rh | 0-5% | 0-5% | 0-5% | 0-5% |
| Se | 0-5% | 0-5% | 0-5% | 0-5% |
| Si | 0-5% | 0-5% | 0-5% | 0-5% |
| Sn | 0-5% | 0-5% | 0-5% | 0-5% |
| Ta | 0-5% | 0-5% | 0-5% | 1-15% |
| Tc | 0-5% | 0-5% | 0-5% | 0-5% |
| Ti | 51-70% | 51-70% | 55-70% | 51-70% |
| V | 0-5% | 0-5% | 0-5% | 0-5% |
| W | 0-5% | 0-5% | 0-5% | 0-5% |
| Y | 0-5% | 0-5% | 0-5% | 0-5% |
| Zr | 20-40% | 22-38% | 27-33% | 1-15% |

| Component/Wt. % | Ex. 191 | Ex. 192 | Ex. 193 | Ex. 194 |
|---|---|---|---|---|
| Ag | 0-5% | 0-5% | 0-5% | 0-5% |
| Al | 0-5% | 0-5% | 0-5% | 0-5% |
| B | 0-5% | 0-5% | 0-5% | 0-5% |
| Bi | 0-5% | 0-5% | 0-5% | 0-5% |
| Cr | 0-5% | 0-5% | 0-5% | 0-5% |
| Cu | 0-5% | 0-5% | 0-5% | 0-5% |
| Co | 0-5% | 0-5% | 0-5% | 0-5% |
| Fe | 0-5% | 0-5% | 0-5% | 0-5% |
| Hf | 0-5% | 0-5% | 0-5% | 0-5% |
| Ir | 0-5% | 0-5% | 0-5% | 0-5% |
| La | 0-5% | 0-5% | 0-5% | 0-5% |
| Mg | 0-5% | 0-5% | 0-5% | 0-5% |
| Mn | 0-5% | 0-5% | 0-5% | 0-5% |
| Mo | 0-5% | 0-5% | 0-5% | 0-5% |
| Nb | 25-40% | 30-40% | 25-40% | 26-32% |
| Ni | 0-5% | 0-5% | 0-5% | 0-5% |
| Os | 0-5% | 0-5% | 0-5% | 0-5% |
| Pt | 0-5% | 0-5% | 0-5% | 0-5% |
| Re | 0-5% | 0-5% | 0-5% | 0-5% |
| Rh | 0-5% | 0-5% | 0-5% | 0-5% |
| Se | 0-5% | 0-5% | 0-5% | 0-5% |
| Si | 0-5% | 0-5% | 0-5% | 0-5% |
| Sn | 0-5% | 0-5% | 0-5% | 0-5% |
| Ta | 2-8% | 3-6% | 5-15% | 10-14% |
| Tc | 0-5% | 0-5% | 0-5% | 0-5% |
| Ti | 51-70% | 52-63% | 51-68% | 51-62% |
| V | 0-5% | 0-5% | 0-5% | 0-5% |
| W | 0-5% | 0-5% | 0-5% | 0-5% |
| Y | 0-5% | 0-5% | 0-5% | 0-5% |
| Zr | 2-12% | 4-8% | 2-8% | 2-6% |

| Component/Wt. % | Ex. 195 | Ex. 196 | Ex. 197 | Ex. 198 |
|---|---|---|---|---|
| Ag | 0-5% | 0-5% | 0-5% | 0-5% |
| Al | 0-5% | 0-5% | 0-5% | 0-5% |
| B | 0-5% | 0-5% | 0-5% | 0-5% |
| Bi | 0-5% | 0-5% | 0-5% | 0-5% |

-continued

| | | | | |
|---|---|---|---|---|
| Cr | 0-5% | 5-35% | 10-30% | 15-25% |
| Cu | 0-5% | 0-5% | 0-5% | 0-5% |
| Co | 0-5% | 20-55% | 25-50% | 35-45% |
| Fe | 0-5% | 3-25% | 0-5% | 0-5% |
| Hf | 0-5% | 0-5% | 0-5% | 0-5% |
| Ir | 0-5% | 0-5% | 0-5% | 0-5% |
| La | 0-5% | 0-5% | 0-5% | 0-5% |
| Mg | 0-5% | 0-5% | 0-5% | 0-5% |
| Mn | 0-5% | 0-5% | 0-5% | 0-5% |
| Mo | 0-5% | 2-15% | 3-12% | 4-9% |
| Nb | 30-40% | 0-5% | 0-5% | 0-5% |
| Ni | 0-5% | 4-23% | 5-20% | 10-18% |
| Os | 0-5% | 0-5% | 0-5% | 0-5% |
| Pt | 0-5% | 0-5% | 0-5% | 0-5% |
| Re | 0-5% | 0-5% | 0-5% | 0-5% |
| Rh | 0-5% | 0-5% | 0-5% | 0-5% |
| Se | 0-5% | 0-5% | 0-5% | 0-5% |
| Si | 0-5% | 0-5% | 0-5% | 0-5% |
| Sn | 0-5% | 0-5% | 0-5% | 0-5% |
| Ta | 1-3% | 0-5% | 0-5% | 0-5% |
| Tc | 0-5% | 0-5% | 0-5% | 0-5% |
| Ti | 51-67% | 0-5% | 0-5% | 0-5% |
| V | 0-5% | 0-5% | 0-5% | 0-5% |
| W | 0-5% | 0-5% | 0-5% | 0-5% |
| Y | 0-5% | 0-5% | 0-5% | 0-5% |
| Zr | 2-5% | 0-5% | 0-5% | 0-5% |

| Component/Wt. % | Ex. 199 | Ex. 200 | Ex. 201 | Ex. 202 |
|---|---|---|---|---|
| Ag | 0-5% | 0-5% | 0-5% | 0-5% |
| Al | 0-5% | 0-5% | 0-5% | 0-5% |
| B | 0-5% | 0-5% | 0-5% | 0-5% |
| Bi | 0-5% | 0-5% | 0-5% | 0-5% |
| Cr | 0-5% | 0-5% | 0-5% | 0-5% |
| Cu | 0-5% | 0-5% | 0-5% | 0-5% |
| Co | 0-5% | 0-5% | 0-5% | 0-5% |
| Fe | 0-5% | 0-5% | 0-5% | 0-5% |
| Hf | 0-5% | 0-5% | 0-5% | 0-5% |
| Ir | 0-5% | 0-5% | 0-5% | 0-5% |
| La | 0-5% | 0-5% | 0-5% | 0-5% |
| Mg | 0-5% | 0-5% | 0-5% | 0-5% |
| Mn | 0-5% | 0-5% | 0-5% | 0-5% |
| Mo | 30-65% | 40-60% | 45-55% | 0-5% |
| Nb | 0-5% | 0-5% | 0-5% | 55-99.75% |
| Ni | 0-5% | 0-5% | 0-5% | 0-5% |
| Os | 0-5% | 0-5% | 0-5% | 0-5% |
| Pt | 0-5% | 0-5% | 0-5% | 0-5% |
| Re | 0-5% | 0-5% | 0-5% | 0-5% |
| Rh | 0-5% | 0-5% | 0-5% | 0-5% |
| Se | 0-5% | 0-5% | 0-5% | 0-5% |
| Si | 0-5% | 0-5% | 0-5% | 0-5% |
| Sn | 0-5% | 0-5% | 0-5% | 0-5% |
| Ta | 0-5% | 0-5% | 0-5% | 0-5% |
| Tc | 0-5% | 0-5% | 0-5% | 0-5% |
| Ti | 0-5% | 0-5% | 0-5% | 0-5% |
| V | 0-5% | 0-5% | 0-5% | 0-5% |
| W | 0-5% | 0-5% | 0-5% | 0-5% |
| Y | 0-5% | 0-5% | 0-5% | 0-5% |
| Zr | 30-56% | 40-60% | 45-55% | 0.25-45% |

| Component/Wt. % | Ex. 203 | Ex. 204 | Ex. 205 | Ex. 206 |
|---|---|---|---|---|
| Ag | 0-5% | 0-5% | 0-5% | 0-5% |
| Al | 0-5% | 0-5% | 0-5% | 0-5% |
| B | 0-5% | 0-5% | 0-5% | 0-5% |
| Bi | 0-5% | 0-5% | 0-5% | 0-5% |
| Cr | 0-5% | 0-5% | 0-5% | 0-5% |
| Cu | 0-5% | 0-5% | 0-5% | 0-5% |
| Co | 0-5% | 0-5% | 0-5% | 0-5% |
| Fe | 0-5% | 0-5% | 0-5% | 0-5% |
| Hf | 0-5% | 0-5% | 0-5% | 0-5% |
| Ir | 0-5% | 0-5% | 0-5% | 0-5% |
| La | 0-5% | 0-5% | 0-5% | 0-5% |
| Mg | 0-5% | 0-5% | 0-5% | 0-5% |
| Mn | 0-5% | 0-5% | 0-5% | 0-5% |
| Mo | 0-5% | 0-5% | 0-5% | 0-5% |
| Nb | 75-99.5% | 95-99.25% | 55-78.5% | 68-74.25% |
| Ni | 0-5% | 0-5% | 0-5% | 0-5% |
| Os | 0-5% | 0-5% | 0-5% | 0-5% |

-continued

| | | | | |
|---|---|---|---|---|
| Pt | 0-5% | 0-5% | 0-5% | 0-5% |
| Re | 0-5% | 0-5% | 0-5% | 0-5% |
| Rh | 0-5% | 0-5% | 0-5% | 0-5% |
| Se | 0-5% | 0-5% | 0-5% | 0-5% |
| Si | 0-5% | 0-5% | 0-5% | 0-5% |
| Sn | 0-5% | 0-5% | 0-5% | 0-5% |
| Ta | 0-5% | 0-5% | 20-35% | 25-30% |
| Tc | 0-5% | 0-5% | 0-5% | 0-5% |
| Ti | 0-5% | 0-5% | 0-5% | 0-5% |
| V | 0-5% | 0-5% | 0-5% | 0-5% |
| W | 0-5% | 0-5% | 1-8% | 0-5% |
| Y | 0-5% | 0-5% | 0-5% | 0-5% |
| Zr | 0.5-25% | 0.75-5% | 0.5-5% | 0.75-3% |

| Element/Wt. % | Ex. 207 | Ex. 208 | Ex. 209 | Ex. 210 |
|---|---|---|---|---|
| Re | 30-75% | 40-75% | 45-75% | 45-70% |
| Cr | 25-70% | 25-65% | 25-55% | 30-55% |
| Mo | 0-25% | 0-25% | 1-25% | 2-25% |
| Bi | 0-25% | 0-25% | 0-25% | 0-25% |
| Cr | 0-25% | 0-25% | 0-25% | 0-25% |
| Ir | 0-25% | 0-25% | 0-25% | 0-25% |
| Nb | 0-25% | 0-25% | 0-25% | 0-25% |
| Ta | 0-25% | 0-25% | 0-25% | 0-25% |
| V | 0-25% | 0-25% | 0-25% | 0-25% |
| W | 0-25% | 0-25% | 0-25% | 0-25% |
| Mn | 0-25% | 0-25% | 0-25% | 0-25% |
| Tc | 0-25% | 0-25% | 0-25% | 0-25% |
| Ru | 0-25% | 0-25% | 0-25% | 0-25% |
| Rh | 0-25% | 0-25% | 0-25% | 0-25% |
| Hf | 0-25% | 0-25% | 0-25% | 0-25% |
| Os | 0-25% | 0-25% | 0-25% | 0-25% |
| Cu | 0-25% | 0-25% | 0-25% | 0-25% |
| Ir | 0-25% | 0-25% | 0-25% | 0-25% |
| Ti | 0-25% | 0-25% | 0-25% | 0-25% |
| Y | 0-25% | 0-25% | 0-25% | 0-25% |
| Zr | 0-25% | 0-25% | 0-25% | 0-25% |

In Examples 1-210, it will be appreciated that all of the above ranges include any value between the range and any other range that is between the ranges set forth above. Any of the above values that include the ≤symbol includes the range from 0 to the stated value and all values and ranges therebetween.

In accordance with another and/or alternative non-limiting aspect of the present disclosure, the medical device is generally designed to include at least about 5 wt. % of the metal alloy (e.g., 5-100 wt. % and all values and ranges therebetween). In one non-limiting embodiment of the disclosure, the medical device includes at least about 50 wt. % of the metal alloy. In another non-limiting embodiment of the disclosure, the medical device includes at least about 95 wt. % of the metal alloy. In one specific configuration, when the medical device includes an expandable frame, the expandable frame is formed of 50-100 wt. % (and all values and ranges therebetween) of the metal alloy, and typically 75-100 wt. % of the metal alloy.

In accordance with another and/or alternative non-limiting aspect of the present disclosure, there is provided a medical device partially or fully formed of metal alloy that includes rhenium in a sufficient quantity as to create a "rhenium effect" in the metal alloy. As defined herein, a "rhenium effect" is a) an increase of at least 10% in ductility of the metal alloy caused by the addition of rhenium to the metal alloy, and/or b) an increase of at least 10% in tensile strength of the metal alloy caused by the addition of rhenium to the metal alloy. It has been found for many metal alloys results in improved ductility and/or tensile strength. It has been found that the addition of rhenium to a metal alloy can result in the formation of a twining alloy in the metal alloy that results in the overall ductility of the metal alloy to increase as the yield and tensile strength increases as a result of reduction and/or work hardening of the metal alloy that includes the rhenium addition. The "rhenium effect" occurs when the atomic weight of rhenium in the metal alloy is at least 15% (e.g., 15 awt. % to 99 atw. % rhenium in the metal alloy and all values and ranges therebetween). For example, for stainless steel alloys, the "rhenium effect" can begin to be present when the stainless steel alloy is modified to include a rhenium amount of at least 5-10 wt. % (and all values and ranges therebetween) of the stainless steel alloy. For CoCr alloys, the "rhenium effect" can begin to be present when the CoCr alloy is modified to include a rhenium amount of at least 4.8-9.5 wt. % (and all values and ranges therebetween) of the CoCr alloy. For TiAlV alloys, the "rhenium effect" can begin to be present when the TiAlV alloy is modified to include a rhenium amount of at least 4.5-9 wt. % (and all values and ranges therebetween) of the TiAlV alloy. At can be appreciated, the rhenium content in the above examples can be greater than the minimum amount to create the "rhenium effect" in the metal alloy.

In accordance with another and/or alternative non-limiting aspect of the present disclosure, there is provided a medical device that is formed of 50-100% (and all values and ranges therebetween) of a metal alloy that includes rhenium in a sufficient amount to create a "rhenium effect" in the metal alloy. In one non-limiting embodiment, the metal alloy includes at least 15 awt. % rhenium (e.g., 15-99.9 atw. % and all values and ranges therebetween), and at least 0.1 wt. % (e.g., 0.1 wt. % to 96 wt. % an all values and ranges therebetween) of one or more additives selected from the group of aluminum, bismuth, calcium, carbon, chromium, cobalt, copper, gold, hafnium, iridium, iron, lanthanum, magnesium, manganese, molybdenum, nickel, niobium, osmium, platinum, rare earth metals, rhodium, ruthenium, silver, tantalum, technetium, titanium, tungsten, vanadium, yttrium, zinc, and/or zirconium. In another non-limiting embodiment, the metal alloy includes at least 15 awt. % rhenium (e.g., 15-99.9 atw. % and all values and ranges therebetween), and at least 0.1 wt. % (e.g., 0.1 wt. % to 96 wt. % an all values and ranges therebetween) of two or more additives selected from the group of aluminum, bismuth, calcium, carbon, chromium, cobalt, copper, gold, hafnium, iridium, iron, lanthanum, magnesium, manganese, molybdenum, nickel, niobium, osmium, platinum, rare earth metals, rhodium, ruthenium, silver, tantalum, technetium, titanium, tungsten, vanadium, yttrium, zinc, and/or zirconium. In another non-limiting embodiment, the metal alloy includes at least 15 awt. % rhenium (e.g., 15-99.9 atw. % and all values and ranges therebetween), and at least 0.1 wt. % (e.g., 0.1 wt. % to 96 wt. % an all values and ranges therebetween) of three or more additives selected from the group of aluminum, bismuth, calcium, carbon, chromium, cobalt, copper, gold, hafnium, iridium, iron, lanthanum, magnesium, manganese, molybdenum, nickel, niobium, osmium, platinum, rare earth metals, rhodium, ruthenium, silver, tantalum, technetium, titanium, tungsten, vanadium, yttrium, zinc, and/or zirconium.

In another and/or alternative non-limiting aspect of the present disclosure, the metal alloy optionally includes less than about 5 wt. % (e.g., 0-4.999999 wt. % and all values and ranges therebetween) other metals and/or impurities, typically 0-1 wt. %, more typically 0-0.1 wt. %, even more typically 0-0.01 wt. %, and still even more typically 0-0.001 wt. %. A high purity level of the metal alloy results in the formation of a more homogeneous alloy, which in turn results in a more uniform density throughout the metal alloy, and also results in the desired yield and ultimate tensile strengths of the metal alloy.

In accordance with another and/or alternative non-limiting aspect of the present disclosure, at least 30 wt. % (e.g., 30-100 wt. % and all values and ranges therebetween) of the metal alloy includes one or more of molybdenum, niobium, rhenium, tantalum, or tungsten. In another non-limiting embodiment, at least 40 wt. % of the metal alloy includes one or more of molybdenum, niobium, rhenium, tantalum, or tungsten. In another non-limiting embodiment, at least 50 wt. % of the metal alloy includes one or more of molybdenum, niobium, rhenium, tantalum, or tungsten.

In another non-limiting embodiment, at least 50 wt. % (e.g., 50-100 wt. % and all values and ranges therebetween) of the metal alloy includes one or more of molybdenum, niobium, rhenium, tantalum, titanium, zirconium or tungsten, and 1-40 wt. % (and all values and ranges therebetween) of the metal alloy includes one or more additives selected from the group of aluminum, bismuth, calcium, carbon, chromium, cobalt, copper, gold, hafnium, iridium, iron, lanthanum, magnesium, manganese, nickel, osmium, platinum, rare earth metals, rhodium, ruthenium, silver, technetium, vanadium, yttrium, zinc, and/or zirconium.

In accordance with another and/or alternative non-limiting aspect of the present disclosure, there is provided a metal alloy wherein at least 20 wt. % (e.g., 20-99 wt. % and all values and ranges therebetween) of the metal alloy includes rhenium. In one non-limiting embodiment, the metal alloy includes at least 20 wt. % (e.g., 20-99.9 wt. % and all values and ranges therebetween) rhenium, and 0.1-80 wt. % (and all values and ranges therebetween) of one or more additives selected from the group of aluminum, bismuth, calcium, carbon, chromium, cobalt, copper, gold, hafnium, iridium, iron, lanthanum, magnesium, manganese, molybdenum, nickel, niobium, osmium, platinum, rare earth metals, rhodium, ruthenium, silver, tantalum, technetium, titanium, tungsten, vanadium, yttrium, zinc, and/or zirconium.

In another non-limiting aspect of the present disclosure, the metals used to form the metal alloy includes rhenium and tungsten and optionally one or more alloying agents such as, but not limited to, aluminum, bismuth, calcium, carbon, chromium, cobalt, copper, gold, hafnium, iridium, iron, lanthanum, magnesium, manganese, molybdenum, nickel, niobium, osmium, platinum, rare earth metals, rhodium, ruthenium, silver, tantalum, technetium, titanium, vanadium, yttrium, zinc, and/or zirconium, and/or alloys of one or more of such components (e.g., WRe, WReMo, etc.). In one non-limiting formulation, the metal alloy includes up to 40 wt. % rhenium and at least 60 wt. % tungsten. In one non-limiting embodiment, the total weight percent of the tungsten and rhenium in the tungsten-rhenium alloy is at least about 95 wt. %, typically at least about 99 wt. %, more typically at least about 99.5 wt. %, yet more typically at least about 99.9 wt. %, and still more typically at least about 99.99 wt. %. In another non-limiting formulation, the metal alloy includes up to 47.5 wt. % rhenium and at least 20-80 wt. % tungsten (and all values and ranges therebetween) and 1-47.5 wt. % molybdenum (and all values and ranges therebetween).

In accordance with another and/or alternative non-limiting aspect of the present disclosure, at least 35 wt. % (e.g., 35-75 wt. % and all values and ranges therebetween) of the metal alloy includes rhenium, and the metal alloy also includes chromium. In one non-limiting embodiment, at least 25 wt. % (e.g., 25-49.9 wt. % and all values and ranges therebetween) of the metal alloy includes chromium. In another non-limiting embodiment, at least 30 wt. % of the metal alloy includes chromium. In another non-limiting embodiment, at least 33 wt. % of the metal alloy includes chromium. In another non-limiting embodiment, at least 50 wt. % (e.g., 50-74.9 wt. % and all values and ranges therebetween) of the metal alloy includes rhenium, at least 25 wt. % (e.g., 25-49.9 wt. % and all values and ranges therebetween) of the metal alloy includes chromium, and 0.1-25 wt. % (and all values and ranges therebetween) of the metal alloy includes one or more of molybdenum, bismuth, niobium, tantalum, titanium, vanadium, tungsten, manganese, zirconium, technetium, ruthenium, rhodium, hafnium, osmium, copper, yttrium, zirconium, and/or iridium. In another non-limiting embodiment, at least 55 wt. % (e.g., 55-69.9 wt. % and all values and ranges therebetween) of the metal alloy includes rhenium, at least 30 wt. % (e.g., 30-44.9 wt. % and all values and ranges therebetween) of the metal alloy includes chromium, and 0.1-15 wt. % (and all values and ranges therebetween) of the metal alloy includes one or more of molybdenum, bismuth, niobium, tantalum, titanium, vanadium, tungsten, manganese, zirconium, technetium, ruthenium, rhodium, hafnium, osmium, copper, yttrium, zirconium, and/or iridium.

In accordance with another and/or alternative non-limiting aspect of the present disclosure, metal alloy includes 10-60 atomic weight percent (atw. %) Re (and all values and ranges therebetween) and one or more metals selected from the group consisting of Mo, Cr, Ta, Nb, Ti, and Zr. In one non-limiting embodiment, the metal alloy includes 15-60 atw % Re and one or more metals selected from the group consisting of Cr, Ta, Nb, Ti, and Zr. In another non-limiting embodiment, the metal alloy includes 15-60 atw % Re and one or more metals selected from the group consisting of 0.5-70 atw. % Cr (and all values and ranges therebetween), 0.5-70 atw. % Ta (and all values and ranges therebetween), 0.5-70 at. % Nb (and all values and ranges therebetween), 0.5-70 atw. % Ti (and all values and ranges therebetween), and 0.5-70 atw. % Zr (and all values and ranges therebetween).

In accordance with another and/or alternative non-limiting aspect of the present disclosure, the metal alloy includes 0.5-50 atw. % Re (and all values and ranges therebetween) and 0.5-70 atw. % Cr (and all values and ranges therebetween).

In accordance with another and/or alternative non-limiting aspect of the present disclosure, the metal alloy includes 0.5-50 atw. % Re (and all values and ranges therebetween) and 0.5-70 atw. % Ta (and all values and ranges therebetween).

In accordance with another and/or alternative non-limiting aspect of the present disclosure, the metal alloy includes 0.5-50 atw. % Re (and all values and ranges therebetween) and 0.5-70 atw. % Nb (and all values and ranges therebetween).

In accordance with another and/or alternative non-limiting aspect of the present disclosure, the metal alloy includes 0.5-50 atw. % Re (and all values and ranges therebetween) and 0.5-70 atw. % Ti (and all values and ranges therebetween).

In accordance with another and/or alternative non-limiting aspect of the present disclosure, the metal alloy includes greater than 50 wt. % titanium (e.g., 51-80 wt. % and all values and ranges therebetween), 15-45 wt. % (and all values and ranges therebetween) niobium, 1-10 wt. % (and all values and ranges therebetween) zirconium, and 1-15 wt. % (and all values and ranges therebetween) tantalum. In one non-limiting formulation, the metal alloy includes 58-70 wt. % titanium, 27-37 wt. % niobium, and 2-9 wt. % zirconium, and 1-15 wt. % tantalum.

In accordance with another and/or alternative non-limiting aspect of the present disclosure, the metal alloy includes greater than 50 wt. % titanium (e.g., 51-80 wt. % and all values and ranges therebetween), 15-45 wt. % (and all values and ranges therebetween) niobium, and 1-10 wt. % (and all values and ranges therebetween) molybdenum. In one non-limiting formulation, the metal alloy includes 58-69 wt. % titanium, 27-33 wt. % niobium, and 4-8 wt. % molybdenum.

In accordance with another and/or alternative non-limiting aspect of the present disclosure, the metal alloy includes 30-60 wt. % cobalt (and all values and ranges therebetween), 10-30 wt. % chromium (and all values and ranges therebetween), 5-20 wt. % iron (and all values and ranges therebetween), 5-22 wt. % nickel (and all values and ranges therebetween), and 2-12 wt. % molybdenum (and all values and ranges therebetween). In one non-limiting formulation, the metal alloy includes 35-45 wt. % cobalt, 15-25 wt. % chromium, 12-20 wt. % iron, 10-20 wt. % nickel, and 5-9 wt. % molybdenum.

In accordance with another and/or alternative non-limiting aspect of the present disclosure, the metal alloy includes 40-60 wt. % zirconium (and all values and ranges therebetween), and 40-60 wt. % molybdenum (and all values and ranges therebetween). In one non-limiting formulation, the metal alloy includes 45-55 wt. % cobalt, and 45-55 wt. % molybdenum.

In accordance with another and/or alternative non-limiting aspect of the present disclosure, the metal alloy includes 90-99.5 wt. % niobium (and all values and ranges therebetween), and 0.5-10 wt. % zirconium (and all values and ranges therebetween). In one non-limiting formulation, the metal alloy includes 95-99.25 wt. % niobium, and 0.75-4 wt. % niobium.

In accordance with another and/or alternative non-limiting aspect of the present disclosure, the metal alloy includes 55-75 wt. % niobium (and all values and ranges therebetween), 18-40 wt. % tantalum (and all values and ranges therebetween), 1-7 wt. % tungsten (and all values and ranges therebetween), and 0.5-4 wt. % zirconium (and all values and ranges therebetween). In one non-limiting formulation, the metal alloy includes 60-70 wt. % niobium, 24-32 wt. % tantalum, 2-5 wt. % tungsten, and 0.75-3 wt. % zirconium.

In accordance with another and/or alternative non-limiting aspect of the present disclosure, the metal alloy includes less than about 5 wt. % (e.g., 0-4.999999 wt. % and all values and ranges therebetween) other metals and/or impurities. A high purity level of the metal alloy results in the formation of a more homogeneous alloy, which in turn results in a more uniform density throughout the metal alloy, and also results in the desired yield and ultimate tensile strengths of the metal alloy. In one non-limiting embodiment, the metal alloy includes less than about 0.5 wt. % other metals and/or impurities. In another non-limiting embodiment, the metal alloy includes less than about 0.2 wt. % other metals and/or impurities. In another non-limiting embodiment, the metal alloy includes less than about 0.1 wt. % other metals and/or impurities. In another non-limiting embodiment, the metal alloy includes less than about 0.05 wt. % other metals and/or impurities. In another non-limiting embodiment, the metal alloy includes less than about 0.01 wt. % other metals and/or impurities.

In accordance with another and/or alternative non-limiting aspect of the present disclosure, the metal alloy is optionally at least partially formed by a swaging process; however, this is not required. In one non-limiting embodiment, swaging is performed on the metal alloy to at least partially or fully achieve final dimensions of one or more portions of the medical device. The swaging operation can be performed on the medical device in the areas to be hardened. For a round or curved portion of a medical device, the swaging can be rotary. For non-round portion of the medical device, the swaging of the non-round portion of the medical device can be performed by non-rotating swaging dies. The swaging temperature for a particular metal alloy can vary. For a metal alloy, the swaging temperature can be from room temperature (RT) (e.g., 10-27° C. and all values and ranges therebetween) to about 400° C. (e.g., 10-400° C. and all values and ranges therebetween) if the swaging is conducted in air or an oxidizing environment. The swaging temperature can be increased to up to about 1500° C. (e.g., 10-1500° C. and all values and ranges therebetween) if the swaging process is performed in a controlled neutral or non-reducing environment (e.g., inert environment). The swaging process can be conducted by repeatedly hammering the medical device at the location to be hardened at the desired swaging temperature. In one non-limiting embodiment, during the swaging process ions of boron and/or nitrogen are allowed to impinge upon rhenium atoms in the refractory metal alloys that include rhenium to form $ReB_2$, $ReN_2$ and/or $ReN_3$; however, this is not required. It has been found that $ReB_2$, $ReN_2$ and/or $ReN_3$ are ultra-hard compounds. As can be appreciated, other refractory metal alloys that include Re and that are subjected to a swaging process can also form $ReB_2$, $ReN_2$ and/or $ReN_3$.

In accordance with another and/or alternative non-limiting aspect of the present disclosure, the metal alloy can optionally be nitrided; however, this is not required. The nitride layer on the metal alloy can function as a lubricating surface during the optional drawing of the metal alloy when partially or fully forming the medical device. After the metal alloy is nitrided, the metal alloy is typically cleaned; however, this is not required. The thickness of the nitrided surface layer is less than about 1 mm. In one non-limiting embodiment, the thickness of the nitrided surface layer is at least about 50 nanometer and less than about 1 mm (and all values and ranges therebetween). In another non-limiting embodiment, the thickness of the nitrided surface layer is at least about 50 nanometer and less than about 0.1 mm. Generally, the weight percent of nitrogen in the nitrided surface layer is 0.0001-5 wt. % nitrogen (and all values and ranges therebetween). In one non-limiting embodiment, the weight percent of nitrogen in the nitrided surface layer is generally less than one of the primary components of the metal alloy, and typically less than each of the two primary components of the metal alloy. For example, when a refractory metal alloy in the form of a MoRe alloy is nitrided, the weight percent of the nitrogen in the nitrided surface layer is less than a weight percent of the molybdenum in the nitrided surface layer. Also, the weight percent of nitrogen in the nitrided surface layer is less than a weight percent of the rhenium in the nitrided surface layer. In one non-limiting composition of the nitrided surface layer on a MoRe alloy (e.g., 40-99 wt. % Mo, 1-40 wt. % Re), the nitrided surface layer comprises 40-99 wt. % molybdenum (and all values and ranges therebetween), 1-40 wt. % rhenium (and all values and ranges therebetween), and 0.0001-5 wt. % nitrogen (and all values and ranges therebetween). In another non-limiting composition of the nitrided surface layer, the nitride surface layer comprises 40-99 wt. % molybdenum, 1-40 wt. % rhenium, and 0.001-1 wt. % nitrogen. As can be appreciated, other refractory metal alloys can be nitrided. For such other metal alloys, the nitride surface layer typically includes 0.001-5 wt. % nitrogen (and all values and ranges therebetween), and the primary constituents of the metal alloy (e.g., metals that constitute at least 5 wt. % of the metal alloy) are present in the nitride surface layer in a greater weight percent than the nitrogen content in the metal alloy. The nitriding process for the metal alloy can be used to increase surface hardness and/or wear resistance of the medical device, and/or to inhibit or prevent discoloration of the metal alloy (e.g., discoloration by oxidation, etc.).

In accordance with another and/or alternative non-limiting aspect of the present disclosure, the metal alloy, just prior to or after being partially or fully formed into the desired medical device, can optionally be cleaned, polished, sterilized, nitrided, etc., for final processing of the metal alloy.

In accordance with another and/or alternative non-limiting aspect of the present disclosure, the use of the metal alloy to partially or fully form the medical device can be used to increase the strength, hardness, and/or durability of the medical device compared with stainless steel, chromium-cobalt alloys, or titanium alloys; thus, a lesser quantity of metal alloy can be used in the medical device to achieve similar strengths compared to medical devices formed of different metals. As such, the resulting medical device can be made smaller and less bulky by use of the metal alloy without sacrificing the strength and durability of the medical device. Such a medical device can have a smaller profile, thus can be inserted in smaller areas, openings, and/or passageways. The metal alloy also can increase the radial strength of the medical device. For example, the thickness of the walls of the medical device and/or the wires used to at least partially form the medical device can be made thinner and achieve a similar or improved radial strength as compared with thicker walled medical devices formed of stainless steel, titanium alloys, or cobalt and chromium alloys. The metal alloy also can improve stress-strain properties, bendability, and flexibility of the medical device, thus increasing the life of the medical device. For example, the medical device can be used in regions that subject the medical device to bending. Due to the improved physical properties of the medical device from the metal alloy, the medical device has improved resistance to fracturing in such frequent bending environments. In addition or alternatively, the improved bendability and flexibility of the medical device due to the use of the metal alloy enables the medical device to be more easily inserted into various regions of a body. The metal alloy can also reduce the degree of recoil during the crimping and/or expansion of the medical device. For example, the medical device better maintains its crimped form and/or better maintains its expanded form after expansion due to the use of the metal alloy. As such, when the medical device is to be mounted onto a delivery device when the medical device is crimped, the medical device better maintains its smaller profile during the insertion of the medical device into various regions of a body. Also, the medical device better maintains its expanded profile after expansion to facilitate in the success of the medical device in the treatment area. In addition to the improved physical properties of the medical device by use of the metal alloy, the metal alloy has improved radiopaque properties as compared to standard materials such as stainless steel or cobalt-chromium alloy, thus reducing or eliminating the need for using marker materials on the medical device. For instance, the metal alloy is believed to at least about 10-20% more radiopaque than stainless steel or cobalt-chromium alloy.

In accordance with another and/or alternative non-limiting aspect of the present disclosure, the medical device can include, contain and/or be coated with one or more agents that facilitate in the success of the medical device and/or treated area. The term "agent" includes, but is not limited to a substance, pharmaceutical, biologic, veterinary product, drug, and analogs or derivatives otherwise formulated and/or designed to prevent, inhibit and/or treat one or more clinical and/or biological events, and/or to promote healing. Non-limiting examples of clinical events that can be addressed by one or more agents include, but are not limited to, viral, fungus and/or bacterial infection; vascular diseases and/or disorders; digestive diseases and/or disorders; reproductive diseases and/or disorders; lymphatic diseases and/or disorders; cancer; implant rejection; pain; nausea; swelling; arthritis; bone diseases and/or disorders; organ failure; immunity diseases and/or disorders; cholesterol problems; blood diseases and/or disorders; lung diseases and/or disorders; heart diseases and/or disorders; brain diseases and/or disorders; neuralgia diseases and/or disorders; kidney diseases and/or disorders; ulcers; liver diseases and/or disorders; intestinal diseases and/or disorders; gallbladder diseases and/or disorders; pancreatic diseases and/or disorders; psychological disorders; respiratory diseases and/or disorders; gland diseases and/or disorders; skin diseases and/or disorders; hearing diseases and/or disorders; oral diseases and/or disorders; nasal diseases and/or disorders; eye diseases and/or disorders; fatigue; genetic diseases and/or disorders; burns; scarring and/or scars; trauma; weight diseases and/or disorders; addiction diseases and/or disorders; hair loss; cramps; muscle spasms; tissue repair; nerve repair; neural regeneration and/or the like. The type and/or amount of agent included in medical device and/or coated on medical device can vary. When two or more agents are included in and/or coated on medical device, the amount of two or more agents can be the same or different. The type and/or amount of agent included on, in and/or in conjunction with medical device are generally selected to address one or more clinical events.

In accordance with another and/or alternative non-limiting aspect of the present disclosure, the amount of agent included on, in and/or used in conjunction with medical device, when the agent is used, is about 0.01-100 ug per $mm^2$ (and all values and ranges wherein between) and/or at least about 0.00001 wt. % of device; however, other amounts can be used. The amount of two of more agents on, in and/or used in conjunction with medical device can be the same or different. The one or more agents can be coated on and/or impregnated in medical device by a variety of mechanisms such as, but not limited to, spraying (e.g., atomizing spray techniques, etc.), flame spray coating, powder deposition, dip coating, flow coating, dip-spin coating, roll coating (direct and reverse), sonication, brushing, plasma deposition, depositing by vapor deposition, MEMS technology, and rotating mold deposition. The amount of two of more agents on, in and/or used in conjunction with medical device, when two one more agents are used, can be the same or different.

In accordance with another and/or alternative non-limiting aspect of the present disclosure, the one or more agents on and/or in the medical device, when used on the medical device, can be released in a controlled manner so the area in question to be treated is provided with the desired dosage of agent over a sustained period of time.

In accordance with another and/or alternative non-limiting aspect of the present disclosure, the one or more polymers used to at least partially control the release of one or more agents from the medical device can be porous or non-porous. The one or more agents can be inserted into and/or applied to one or more surface structures and/or micro-structures on the medical device, and/or be used to at least partially form one or more surface structures and/or micro-structures on the medical device.

In accordance with another and/or alternative non-limiting aspect of the present disclosure, the thickness of each polymer layer and/or layer of agent is generally at least about 0.01 μm and is generally less than about 150 μm (e.g., 0.01-149.9999 μm and all values and ranges therebetween). In one non-limiting embodiment, the thickness of a polymer layer and/or layer of agent is about 0.02-75 μm, more particularly about 0.05-50 μm, and even more particularly about 1-30 μm. As can be appreciated, other thicknesses can be used.

In accordance with another and/or alternative non-limiting aspect of the present disclosure, a variety of polymers can be coated on the medical device and/or be used to form at least a portion of the medical device. When one or more layers of polymer are coated onto at least a portion of the medical device, the one or more coatings can be applied by a variety of techniques such as, but not limited to, vapor deposition and/or plasma deposition, spraying, dip-coating, roll coating, sonication, atomization, brushing and/or the like; however, other or additional coating techniques can be used. The one or more polymers that can be coated on the medical device and/or used to at least partially form the medical device can be polymers that are considered to be biodegradable, bioresorbable, or bioerodable; polymers that are considered to be biostable; and/or polymers that can be made to be biodegradable and/or bioresorbable with modification.

In accordance with another and/or alternative non-limiting aspect of the present disclosure, the medical device can optionally include a marker material that facilitates enabling the medical device to be properly positioned in a body passageway (e.g., blood vessel, heart valve, etc.). The marker material is typically designed to be visible to electromagnetic waves (e.g., x-rays, microwaves, visible light, infrared waves, ultraviolet waves, etc.); sound waves (e.g., ultrasound waves, etc.); magnetic waves (e.g., MRI, etc.); and/or other types of electromagnetic waves (e.g., microwaves, visible light, infrared waves, ultraviolet waves, etc.). In one non-limiting embodiment, the marker material is visible to x-rays (i.e., radiopaque).

In accordance with another and/or alternative non-limiting aspect of the present disclosure, the medical device or one or more regions of the medical device can optionally be constructed by use of one or more microelectromechanical manufacturing (MEMS) techniques (e.g., micro-machining, laser micro-machining, laser micro-machining, micro-molding, 3D printing, etc.); however, other or additional manufacturing techniques can be used.

In accordance with another and/or alternative non-limiting aspect of the present disclosure, the medical device can optionally include one or more surface structures (e.g., pore, channel, pit, rib, slot, notch, bump, teeth, needle, well, hole, groove, etc.). These structures can be at least partially formed by MEMS (e.g., micro-machining, etc.) technology and/or other types of technology (e.g., 3D printing, etc.).

In accordance with another and/or alternative non-limiting aspect of the present disclosure, the medical device can optionally include one or more micro-structures (e.g., micro-needle, micro-pore, micro-cylinder, micro-cone, micro-pyramid, micro-tube, micro-parallelopiped, micro-prism, micro-hemisphere, teeth, rib, ridge, ratchet, hinge, zipper, zip-tie-like structure, etc.) on the surface of the medical device. As defined herein, a "micro-structure" is a structure having at least one dimension (e.g., average width, average diameter, average height, average length, average depth, etc.) that is no more than about 2 mm, and typically no more than about 1 mm. Non-limiting examples of structures that can be formed on the medical device are illustrated in United States Patent Publication Nos. 2004/0093076 and 2004/0093077, which are incorporated herein by reference. Typically, the micro-structures (when formed) extend from or into the outer surface no more than about 400 microns (0.01-400 microns and all values and ranges therebetween), and more typically less than about 300 microns, and more typically about 15-250 microns; however, other sizes can be used.

In accordance with another and/or alternative non-limiting aspect of the present disclosure, the medical device can optionally be an expandable device that can be expanded by use of some other device (e.g., balloon, etc.).

In accordance with another and/or alternative non-limiting aspect of the present disclosure, the medical device can optionally be fabricated from a material having no or substantially no shape-memory characteristics.

In accordance with another and/or alternative non-limiting aspect of the present disclosure, there is optionally provided a near net process for a frame and/or other metal component of the medical device. In one non-limiting embodiment of the disclosure, there is provided a method of powder pressing materials and optionally increasing the strength post-sintering by imparting additional cold work. In one non-limiting embodiment, the green part is pressed and then sintered. Thereafter, the sintered part is again pressed to increase its mechanical strength by imparting cold work into the pressed and sintered part. Generally, the temperature during the pressing process after the sintering process is 20-100° C. (and all values and ranges therebetween), typically 20-80° C., and more typically 20-40° C. As defined herein, cold working occurs at a temperature of no more than 150° C. (e.g., 10-150° C. and all values and ranges therebetween). The change in the shape of the repressed post-sintered part needs to be determined so the final part (pressed, sintered, and re-pressed) meets the dimensional requirements of the final formed part. There is also provided an optional process of increasing the mechanical strength of a pressed metal part by repressing the post-sintered part to add additional cold work into the material, thereby increasing its mechanical strength. There is also provided an optional process of powder pressing to a near net or final part using metal powder.

In accordance with another and/or alternative non-limiting aspect of the present disclosure, there is optionally provided a press of near net or finished part composite. The process of pressing metals into near net of finished parts is well established; however, pressing a composite structure formed of metal powder and polymer for purposes of making complex part geometries and foam like structures is new. Similarly, using a pressing process to impart particular biologic substances into the metal matrix is also new. In one non-limiting embodiment, there is provided a process of creating a metal part with pre-defined voids to create a trabecular or foam structure composed of mixing a metal and polymer powder, and then pressing the powder into a finished part or semi-finished green part, and then sintering the part under which conditions the polymer leaves the metal behind through a process of thermal degradation of the polymer. The resulting part has a porosity associated with the size of the polymer particles as well as the homogeneity of the mixture upon pressing prior to sintering. In another non-limiting embodiment, there is provided a process by which a residual of the polymer is left behind after thermal degradation (on the metal substrate) and the polymer residual has some desired biological affect (e.g., masking the metal from the body by encapsulation, promotion of cellular attachment and growth). The polymer and metal powders can be of varying sizes to create a multiplied of voids—some large, creating a pathway for cellular growth, and some small, creating a ruff surface to promote cellular attachment. As such, the use of a polymer in combination with metal powder and subsequent pressing and sintering can be used to form novel and customized shapes for medical device or the near net form of the medical device. Generally, the polymer constitutes about 0.1-70 vol. % (and all values and ranges therebetween) of the consolidated and pressed material prior to the sintering step, typically the polymer constitutes about 1-60 vol. % of the consolidated and pressed material prior to the sintering step, more typically the polymer constitutes about 2-50 vol. % of the consolidated and pressed material prior to the sintering step, and even more typically the polymer constitutes about 2-45 vol. % of the consolidated and pressed material prior to the sintering step. As such, if the polymer constitutes about 5 vol. % of the consolidated and pressed material prior to the sintering step, if after the sintering step at least 95% (e.g., 95-100% and all values and ranges therebetween) of the polymer is degraded and removed from the part or medical device, then the part could include up to about 5 vol. % cavities and/or passageways in the medical device. After the sintering process, at least 95 vol. % (95%-100% and all values and ranges therebetween) of the polymer is thermally degraded and/or removed from the sintered material.

In accordance with another and/or alternative non-limiting aspect of the present disclosure, the metal alloy used to at least partially form the medical device is initially formed into a near net part, blank, a rod, a tube, etc., and then finished into final form by one or more finishing processes (e.g., centerless grinding, turning, electropolishing, drawing process, grinding, laser cutting, shaving, polishing, EDM cutting, micro-machining, laser micro-machining, micro-molding, machining, drilling (e.g., gun drilling, etc.), 3D printing, cold wording, swaging, cleaning, buffing, smoothing, nitriding, annealing, plug drawing, etching (chemical etching, plasma etching, etc.), chemical modifications, chemical reactions, photo-etching, chemical coatings, etc.).

In accordance with another and/or alternative non-limiting aspect of the present disclosure, the metal alloy near net part, blank, rod, tube, etc., can be formed by various techniques such as, but not limited to, 1) melting the metal alloy and/or metals that form the metal alloy (e.g., vacuum arc melting, etc.) and then extruding and/or casting the metal alloy into a near net part, blank, rod, tube, etc., 2) melting the metal alloy and/or metals that form the metal alloy, forming a metal strip and then rolling and welding the strip into a near net part, blank, rod, tube, etc., 3) consolidating (pressing, pressing and sintering, etc.) the metal powder of the metal alloy and/or metal powder of metals that form the metal alloy into a near net part, blank, rod, tube, etc., and/or 4) 3D print the metal alloy into a near net part, blank, rod, tube, etc. When the metal alloy is formed into a blank, the shape and size of the blank is non-limiting. When the metal alloy is formed into a rod or tube, the rod or tube generally has a length of about 48 inches or less (e.g., 0.1-48 inches and all values and ranges therebetween); however, longer lengths can be formed.

In accordance with another and/or alternative non-limiting aspect of the present disclosure, when a solid rod of the metal alloy is formed, the rod is then formed into a tube prior to reducing the outer cross-sectional area or diameter of the rod. The rod can be formed into a tube by a variety of processes such as, but not limited to, cutting or drilling (e.g., gun drilling, etc.) or by cutting (e.g., EDM, EDM sinker, wire EDM, etc.) or by 3D printing. The cavity or passageway formed in the rod typically is formed fully through the rod; however, this is not required.

In yet a further and/or alternative non-limiting aspect of the present disclosure, the near net medical device, blank, rod, tube, etc., can optionally be cleaned and/or polished after the near net medical device, blank, rod, tube, etc., has been form; however, this is not required. Typically, the near net medical device, blank, rod, tube, etc., is cleaned and/or polished prior to being further processed; however, this is not required.

In still yet a further and/or alternative non-limiting aspect of the present disclosure, the near net medical device, blank, rod, tube, etc., can be resized to the desired dimension of the medical device. In one non-limiting embodiment, the cross-sectional area or diameter of the near net medical device, blank, rod, tube, etc., is reduced to a final near net medical device, blank, rod, tube, etc., dimension in a single step or by a series of steps. The reduction of the outer cross-sectional area or diameter of the near net medical device, blank, rod, tube, etc. may be obtained by centerless grinding, turning, electropolishing, drawing process, grinding, laser cutting, shaving, polishing, EDM cutting, etc. The outer cross-sectional area or diameter size of the near net medical device, blank, rod, tube, etc., can be reduced by the use of one or more drawing processes; however, this is not required. During the drawing process, care should be taken to not form micro-cracks in the near net medical device, blank, rod, tube, etc., during the reduction of the near net medical device, blank, rod, tube, etc., outer cross-sectional area or diameter.

In another and/or alternative non-limiting aspect of the present disclosure, the near net medical device, blank, rod, tube, etc. general if not reduced in cross-sectional area by more about 25% (e.g., 0.1-25% and all values and ranges therebetween) each time the near net medical device, blank, rod, tube, etc. is drawn down in size. When the near net medical device, blank, rod, tube, etc. optionally includes a nitride layer, the nitrided layer can optionally function as a lubricating surface during the drawing process to facilitate in the drawing of the near net medical device, blank, rod, tube, etc.

In another and/or alternative non-limiting aspect of the present disclosure, the near net medical device, blank, rod, tube, etc. is cooled after being annealed; however, this is not required. Generally, the near net medical device, blank, rod, tube, etc. is cooled at a fairly quick rate after being annealed so as to inhibit or prevent the formation of a sigma phase in the metal alloy; however, this is not required. Generally, the near net medical device, blank, rod, tube, etc. is cooled at a rate of at least about 50° C. per minute (e.g., 50-500° C. per minute and all values and ranges therebetween) after being annealed, typically at least about 75° C. per minute after being annealed, more typically at least about 100° C. per minute after being annealed, even more typically about 100-400° C. per minute after being annealed, still even more typically about 150-350° C. per minute after being annealed, and yet still more typically about 200-300° C. per minute after being annealed, and still yet even more typically about 250-280° C. per minute after being annealed; however, this is not required.

In another and/or alternative non-limiting aspect of the present disclosure, the near net medical device, blank, rod, tube, etc. is annealed after one or more drawing processes. The metal alloy blank, rod, tube, etc. can be annealed after each drawing process or after a plurality of drawing processes. The metal alloy blank, rod, tube, etc. is typically annealed prior to about a 60% cross-sectional area size reduction of the metal alloy blank, rod, tube, etc. In other words, the near net medical device, blank, rod, tube, etc. should not be reduced in cross-sectional area by more than 60% before being annealed (e.g., 0.1-60% reduction and all values and ranges therebetween).

In accordance with another and/or alternative non-limiting aspect of the present disclosure, when the near net medical device, blank, rod, tube, etc. is annealed, the near net medical device, blank, rod, tube, etc. is typically heated to a temperature of about 500-1700° C. (and all values and ranges therebetween) for a period of about 1-200 minutes (and all values and ranges therebetween); however, other temperatures and/or times can be used. The annealing process typically occurs in an inert environment or an oxygen-reducing environment so as to limit the amount of impurities that may embed themselves in the metal alloy during the annealing process. One non-limiting oxygen-reducing environment that can be used during the annealing process is a hydrogen environment; however, it can be appreciated that a vacuum environment can be used or one or more other or additional gasses can be used to create the oxygen-reducing environment.

In accordance with another and/or alternative non-limiting aspect of the present disclosure, the parameters for annealing can be changed as the near net medical device, blank, rod, tube, etc. as the cross-sectional area or diameter;

and/or wall thickness of the near net medical device, blank, rod, tube, etc. are changed. It has been found that good grain size characteristics of the near net medical device, blank, rod, tube, etc. can be achieved when the annealing parameters are varied as the parameters of the near net medical device, blank, rod, tube, etc. change. After each annealing process, the grain size of the metal in the near net medical device, blank, rod, tube, etc. should be no greater than 4 ASTM. Generally, the grain size range is about 4-20 ASTM (and all values and ranges therebetween).

In accordance with another and/or alternative non-limiting aspect of the present disclosure, the near net medical device, blank, rod, tube, etc. can be cleaned prior to and/or after being annealed.

In accordance with another and/or alternative non-limiting aspect of the present disclosure, the near net medical device, blank, rod, tube, etc., after a) being formed to the desired green shape, b) after being formed to have the desired outer cross-sectional area or diameter, and/or c) after being formed to have the desired inner cross-sectional area or diameter and/or wall thickness, can then be cut and/or etched to at least partially form the desired configuration of the medical device (e.g., stent, TAV valve, etc.). The near net medical device, blank, rod, tube, etc. can be cut or otherwise formed by one or more processes (e.g., centerless grinding, turning, electropolishing, drawing process, grinding, laser cutting, shaving, polishing, EDM cutting, etching, micro-machining, laser micro-machining, micro-molding, machining, etc.). As can be appreciated, a portion or all of the medical device can be formed by 3D printing.

In accordance with another and/or alternative non-limiting aspect of the present disclosure, the metal alloy can be coated with an enhancement coating to improve one or more properties of the metal alloy (e.g., change exterior color of metal alloy, increase hardness of coated surface, increase toughness of coated surface, reduced friction to coated surface, improve impact wear of coated surface, improve resistance to corrosion and oxidation, form a non-stick coated surface, improve biocompatibility of metal alloy having the coated surface, reduce toxicity of metal alloy having the coated surface, etc.). Non-limiting enhancement coatings that can be applied to a portion of all of the outer surface of the metal alloy includes chromium nitride (CrN), diamond-like carbon (DLC), titanium nitride (TiN), zirconium nitride (ZrN), zirconium oxide ($ZrO_2$), zirconium-nitrogen-carbon (ZrNC), zirconium OxyCarbide (ZrOC), and combinations of such coatings. In one non-limiting embodiment, the one or more enhancement coatings are applied to a portion of all of the outer surface of the metal alloy can be a vacuum process using an energy source to vaporize material and deposit a thin layer of enhancement coating material. Such vacuum coating process includes a physical vapor deposition (PVD) process (e.g., sputter deposition, cathodic arc deposition or electron beam heating, etc.), chemical vapor deposition (CVD) process, atomic layer deposition (ALD) process, or a plasma-enhanced chemical vapor deposition (PE-CVD) process. In one non-limiting embodiment, the coating process is one or more of a PVD, CVD, ALD and PE-CVD, and wherein the coating process occurs at a temperature of 200-400° C. (and all values and ranges therebetween) for at least 10 minutes (e.g., 10-400 minutes and all values and ranges therebetween). In another non-limiting embodiment, the coating process is one or more of a PVD, CVD, ALD and PE-CVD, and wherein the coating process occurs at a temperature of 220-300° C. for 60-120 minutes. The materials of the one or more enhancement coatings can be combine with one or more metals in the metal alloy, and/or combined with nitrogen, oxygen, carbon, or other elements that are in the metal alloy and/or present in the atmosphere about the metal alloy to a form an enhancement coating on the outer surface of the metal alloy that can have enhanced properties (e.g., enhancement coating is harder than case-hardened steel, enhancement coating is more scratch-resistant than hardened chrome, enhancement coating having high corrosion resistance, etc.). In another non-limiting embodiment, the one or more enhancement coatings can be form various coating colors on the outer surface of the metal alloy (e.g., gold, copper, brass, black, rose gold, chrome, blue, silver, yellow, green, etc.). In another non-limiting embodiment, the thickness of the enhancement coating is greater than 1 nanometer (e.g., 2 nanometers to 100 microns and all values and ranges therebetween), and typically 0.1-25 microns, and more typically 1-10 microns. In another non-limiting embodiment, the hardness of the enhancement coating is at 5 GPa (ASTM C1327-15 or ASTM C1624-05), typically 5-50 GPa (and all values and ranges therebetween), more typically 10-25 GPa, and still more typically 14-24 GPa. In another non-limiting embodiment, the coefficient of friction (COF) of the enhancement coating is 0.04-0.2 (and all values and ranges therebetween), and typically 0.6-0.15. In another non-limiting embodiment, the wear rate of the enhancement coating is $0.5 \times 10^{-7}$ mm$^3$/N-m to $3 \times 10^{-7}$ mm$^3$/N-m (an all values and ranges therebetween), and typically $1.2 \times 10^{-7}$ mm$^3$/N-m to $2 \times 10^{-7}$ mm$^3$/N-m. In another non-limiting embodiment, silicon-based precursors (e.g., trimethysilane, tetramethylsilane, hexachlorodisilane, silane, dichlorosilane, trichlorosilane, silicon tetrachloride, tris(dimethylamino) silane, bis (tert-butylamino)silane, trisilylamine, allyltrimethoxysilane, (3-aminopropyl)triethoxysilane, butyltrichlorosilane, n-sec-butyl(trimethylsilyl)amine, chloropentamethyldisilane, 1,2-dichlorotetramethyldisilane, [3-(diethylamino)propyl] trimethoxysilane, 1,3-diethyl-1,1,3,3-tetramethyldisilazane, dimethoxydimethylsilane, dodecamethylcyclohexasilane, hexamethyldisilane, isobutyl(trimethoxy)silane, methyltrichlorosilane, 2,4,6,8,10-pentamethylcyclopentasiloxane, pentamethyldisilane, n-propyltriethoxysilane, silicon tetrabromide, silicon tetrabromide, etc.) can be used to facilitate in the application of the enhancement coating to one or more portions or all of the outer surface of the metal alloy. In one non-limiting embodiment, the enhancement coating optionally includes no more than 0.1 wt. % nickel, no more than 0.1 wt. % chromium, and/or no more than 0.1 wt. % cobalt. In another non-limiting embodiment, the outer surface of the medical device optionally includes no more than 0.1 wt. % nickel, no more than 0.1 wt. % chromium, and/or no more than 0.1 wt. % cobalt. The adhesion layer optionally includes no more than 0.1 wt. % nickel, no more than 0.1 wt. % chromium, and/or no more than 0.1 wt. % cobalt. The metal alloy that forms a portion or all of the medical device optionally includes no more than 0.1 wt. % nickel, no more than 0.1 wt. % chromium, and/or no more than 0.1 wt. % cobalt.

Another and/or alternative non-limiting object of the present disclosure is the provision of a medical device wherein the enhancement coating includes is partially or fully applied to a metallic adhesion layer. In one non-limiting embodiment, the metallic adhesion layer optionally includes titanium metal or zirconium metal. In another on-limiting embodiment, the metallic adhesion layer optionally has a thickness of 1 to 500 nanometers (and all values and ranges therebewtween). The enhancement coating and/ or the metallic adhesion layer can be applied by use of a vacuum coating process (e.g., physical vapor deposition (PVD) process (e.g., sputter deposition, cathodic arc deposition or electron beam heating, etc.), chemical vapor deposition (CVD) process, atomic layer deposition (ALD) process, or a plasma-enhanced chemical vapor deposition (PE-CVD) process), plating process, etc.

In accordance with another and/or alternative non-limiting aspect of the present disclosure, the metal alloy is coated with an enhancement coating to improve one or more properties of the metal alloy wherein the enhancement coating composition includes a chromium nitride (CrN) coating. A portion or all of the outer surface of the metal alloy can include the chromium nitride (CrN) coating. The enhancement coating can be used to improve hardness, improve toughness, reduced friction, resistant impact wear, improve resistance to corrosion and oxidation, and/or form a reduced stick surface when in contact with many different materials. In accordance with one non-limiting embodiment, the metal alloy is coated with an enhancement coating that generally includes 40-85 wt. % Cr (and all values and ranges therebetween), 15-60 wt. % N (and all values and ranges therebetween), 0-10 wt. % Re (and all values and ranges therebetween), 0-10 wt. % Si (and all values and ranges therebetween), 0-2 wt. % O (and all values and ranges therebetween), and 0-2 wt. % C (and all values and ranges therebetween). In one non-limiting coating process, all or a portion of the outer surface of the metal alloy is initially coated with Cr metal. The Cr metal coating can be applied by PVD, CVD, ALD and PE-CVD in an inert environment. The coating thickness of Cr metal is 0.5-15 microns. Thereafter, the Cr metal coating is exposed to nitrogen gas and/or a nitrogen containing gas compound to cause the nitrogen to react with the Cr metal coating to form a layer of CrN on the outer surface of the Cr metal coating and/or the outer surface of the metal alloy. In another non-limiting embodiment, the enhancement coating composition generally includes 65-80 wt. % Cr, 15-30 wt. % N, 0-8 wt. % Re, 0-1 wt. % Si, 0-1 wt. % O, and 0-1 wt. % C.

In accordance with another and/or alternative non-limiting aspect of the present disclosure, the metal alloy is coated with an enhancement coating to improve one or more properties of the metal alloy wherein the enhancement coating composition generally includes a diamond-Like Carbon (DLC) coating. A portion or all of the outer surface of the metal alloy can include the diamond-Like Carbon (DLC) coating. The enhancement coating can be used to improve hardness, improve toughness, reduced friction, resistant impact wear, improve resistance to corrosion and oxidation, improve biocompatibility, and/or form a reduced stick surface when in contact with many different materials. In one non-limiting embodiment, all or a portion of the outer surface of the metal alloy is coated with the enhancement coating composition that generally includes 60-99.99 wt. % C (and all values and ranges therebetween), 0-2 wt. % N (and all values and ranges therebetween), 0-10 wt. % Re (and all values and ranges therebetween), 0-20 wt. % Si (and all values and ranges therebetween), and 0-2 wt. % O (and all values and ranges therebetween). The carbon coating can be applied by PVD, CVD, ALD and PE-CVD in an inert environment. The carbon layer can be applied by use of methane and/or acetylene gas; however, other or additional carbon sources can be used. The coating thickness of the carbon is 0.5-15 microns. In another non-limiting embodiment, all or a portion of the outer surface of the metal alloy is coated with the enhancement coating composition that generally includes 90-99.99 wt. % C, 0-1 wt. % N, 0-8 wt. % Re, 0-1 wt. % Si, and 0-1 wt. % 0.

In accordance with another and/or alternative non-limiting aspect of the present disclosure, the metal alloy is coated with an enhancement coating to improve one or more properties of the metal alloy wherein the enhancement coating composition generally includes a titanium nitride (TiN) coating. A portion or all of the outer surface of the metal alloy can include the titanium nitride (TiN) coating. The enhancement coating can be used to improve hardness, improve toughness, improve resistance to corrosion and oxidation, reduced friction, and/or form a reduced stick surface when in contact with many different materials. In one non-limiting embodiment, all or a portion of the outer surface of the metal alloy is initially coated with Ti metal. The Ti metal coating can be applied by PVD, CVD, ALD and PE-CVD in an inert environment. The coating thickness of Ti metal is 0.5-15 microns. Thereafter, the Ti metal coating is exposed to nitrogen gas and/or a nitrogen containing gas compound to cause the nitrogen to react with the Ti metal coating to form a layer of TiN on the outer surface of the Ti metal coating and/or the outer surface of the metal alloy. In another non-limiting embodiment, the enhancement coating composition generally includes 20-85 wt. % Ti (and all values and ranges therebetween), 5-30 wt. % N (and all values and ranges therebetween), 0-10 wt. % Re (and all values and ranges therebetween), 0-20 wt. % Si (and all values and ranges therebetween), 0-2 wt. % O (and all values and ranges therebetween), and 0-2 wt. % C (and all values and ranges therebetween). In another non-limiting embodiment, the enhancement coating composition generally includes 70-80 wt. % Ti, 20-25 wt. % N, 0-8 wt. % Re, 0-1 wt. % Si, 0-1 wt. % O, and 0-1 wt. % C.

In accordance with another and/or alternative non-limiting aspect of the present disclosure, the metal alloy is coated with an enhancement coating to improve one or more properties of the metal alloy wherein the enhancement coating composition generally includes a zirconium nitride (ZrN) coating. A portion or all of the outer surface of the metal alloy can include the zirconium nitride (ZrN) coating. The enhancement coating can be used to improve hardness, improve toughness, improve resistance to corrosion and oxidation, reduced friction, and/or form a reduced stick surface when in contact with many different materials. In one non-limiting embodiment all or a portion of the outer surface of the metal alloy is initially coated with Zr metal. The Zr metal coating can be applied by PVD, CVD, ALD and PE-CVD in an inert environment. The coating thickness of Zr metal is 0.5-15 microns. Thereafter, the Zr metal coating is exposed to nitrogen gas and/or a nitrogen containing gas compound to cause the nitrogen to react with the Zn metal coating to form a layer of ZrN on the outer surface of the Zr metal coating and/or the outer surface of the metal alloy. The ZrN coating has been found to produce a gold colored enhancement coating color. In another non-limiting embodiment, the enhancement coating composition generally includes 35-90 wt. % Zr (and all values and ranges therebetween), 5-25 wt. % N (and all values and ranges therebetween), 0-10 wt. % Re (and all values and ranges therebetween), 0-20 wt. % Si (and all values and ranges therebetween), 0-2 wt. % O (and all values and ranges therebetween), and 0-2 wt. % C (and all values and ranges therebetween). In another non-limiting embodiment, the enhancement coating composition generally includes 80-90 wt. % Zr, 10-20 wt. % N, 0-8 wt. % Re, 0-1 wt. % Si, 0-1 wt. % O, and 0-1 wt. % C.

In accordance with another and/or alternative non-limiting aspect of the present disclosure, the metal alloy is coated with an enhancement coating to improve one or more properties of the metal alloy wherein the enhancement coating composition generally includes a zirconium oxide (ZrO$_2$) coating. A portion or all of the outer surface of the metal alloy can include the zirconium oxide (ZrO$_2$) coating. The enhancement coating can be used to improve hardness, improve toughness, improve resistance to corrosion and oxidation, reduced friction, and/or form a reduced stick surface when in contact with many different materials. In one non-limiting embodiment all or a portion of the outer surface of the metal alloy is initially coated with Zr metal. The Zr metal coating can be applied by PVD, CVD, ALD and PE-CVD in an inert environment. The coating thickness of Zr metal is 0.5-15 microns. Thereafter, the Zr metal coating is exposed to oxygen gas and/or oxygen containing gas compound to cause the oxygen to react with the Zn metal coating to form a layer of zirconium oxide (ZrO$_2$) on the outer surface of the Zr metal coating and/or the outer surface of the metal alloy. The zirconium oxide (ZrO$_2$) coating has been found to produce a blue colored enhancement coating color. In another non-limiting embodiment, the enhancement coating composition generally includes 35-90 wt. % Zr (and all values and ranges therebetween), 10-35 wt. % O (and all values and ranges therebetween), 0-2 wt. % N (and all values and ranges therebetween), 0-10 wt. % Re (and all values and ranges therebetween), 0-20 wt. % Si (and all values and ranges therebetween), and 0-2 wt. % C (and all values and ranges therebetween). In another non-limiting embodiment, the enhancement coating composition generally includes 70-80 wt. % Zr, 20-30 wt. %, 0-1 wt. % N, 0-8 wt. % Re, 0-1 wt. % Si, and 0-1 wt. % C.

In accordance with another and/or alternative non-limiting aspect of the present disclosure, the metal alloy is coated with an enhancement coating to improve one or more properties of the metal alloy wherein the enhancement coating composition generally includes both a zirconium oxide (ZrO$_2$) coating and a zirconium nitride coating (ZrN). A portion or all of the outer surface of the metal alloy can include the zirconium oxide (ZrO$_2$) coating and the zirconium nitride coating (ZrN). The enhancement coating can be used to improve hardness, improve toughness, improve resistance to corrosion and oxidation, reduced friction, and/or form a reduced stick surface when in contact with many different materials. In one non-limiting embodiment all or a portion of the outer surface of the metal alloy is initially coated with Zr metal. The Zr metal coating can be applied by PVD, CVD, ALD and PE-CVD in an inert environment. The coating thickness of Zr metal is 0.5-15 microns. Thereafter, the Zr metal coating is exposed to a) both oxygen gas and/or oxygen containing gas compound and also to nitrogen gas and/or nitrogen containing gas compound, b) nitrogen gas and/or nitrogen containing gas compound and then to oxygen gas and/or oxygen containing gas compound, or c) oxygen gas and/or oxygen gas containing compound and then to nitrogen gas and/or nitrogen gas containing compound. The coating composition of the zirconium oxide (ZrO$_2$) coating and the zirconium nitride coating (ZrN) are similar or the same as discussed above.

In accordance with another and/or alternative non-limiting aspect of the present disclosure, the metal alloy is coated with an enhancement coating to improve one or more properties of the metal alloy wherein the enhancement coating composition generally includes a zirconium oxycarbide (ZrOC) coating. A portion or all of the outer surface of the metal alloy can include the zirconium oxycarbide (ZrOC) coating. The enhancement coating can be used to improve hardness, improve toughness, improve resistance to corrosion and oxidation, reduced friction, and/or form a reduced stick surface when in contact with many different materials. In one non-limiting embodiment all or a portion of the outer surface of the metal alloy is initially coated with Zr metal. The Zr metal coating can be applied by PVD, CVD, ALD and PE-CVD in an inert environment. The coating thickness of Zr metal is 0.5-15 microns. Thereafter, the Zr metal coating is exposed to a) both to oxygen gas and/or an oxygen containing gas compound and to carbon and/or a carbon containing gas compound (e.g., methane and/or acetylene gas), b) carbon and/or a carbon containing gas compound and then to oxygen gas and/or an oxygen containing gas compound, or c) oxygen gas and/or oxygen containing gas compound and then to carbon and/or carbon containing gas compound. In another non-limiting embodiment, the enhancement coating composition generally includes 40-95 wt. % Zr (and all values and ranges therebetween), 5-25 wt. % O (and all values and ranges therebetween), and 10-40 wt. % C (and all values and ranges therebetween), 0-2 wt. % N (and all values and ranges therebetween), 0-10 wt. % Re (and all values and ranges therebetween), and 0-20 wt. % Si (and all values and ranges therebetween). In another non-limiting embodiment, the enhancement coating composition generally includes 40-65 wt. % Zr, 5-25 wt. % O, and 25-40 wt. % C, 0-1 wt. % N, 0-8 wt. % Re, and 0-1 wt. % Si.

In accordance with another and/or alternative non-limiting aspect of the present disclosure, the metal alloy is coated with an enhancement coating to improve one or more properties of the metal alloy wherein the enhancement coating composition generally includes a zirconium-nitrogen-carbon (ZrNC) coating. A portion or all of the outer surface of the metal alloy can include the zirconium-nitrogen-carbon (ZrNC) coating. The enhancement coating can be used to improve hardness, improve toughness, improve resistance to corrosion and oxidation, reduced friction, and/or form a reduced stick surface when in contact with many different materials. In one non-limiting embodiment all or a portion of the outer surface of the metal alloy is initially coated with Zr metal. The Zr metal coating can be applied by PVD, CVD, ALD and PE-CVD in an inert environment. The coating thickness of Zr metal is 0.5-15 microns. Thereafter, the Zr metal coating is exposed to nitrogen gas and/or a nitrogen containing gas compound and then to carbon and/or a carbon containing gas compound (e.g., methane and/or acetylene gas). The color of the ZrNC will vary depending on the amount of C and N in the coating. In one non-limiting embodiment, the enhancement coating composition generally includes 40-95 wt. % Zr (and all values and ranges therebetween), 5-40 wt. % N (and all values and ranges therebetween), and 5-40 wt. % C (and all values and ranges therebetween), 0-2 wt. % O (and all values and ranges therebetween), 0-10 wt. % Re (and all values and ranges therebetween), and 0-20 wt. % Si (and all values and ranges therebetween). In another non-limiting embodiment, the enhancement coating composition generally includes 40-80 wt. % Zr, 5-25 wt. % N, and 5-25 wt. % C, 0-1 wt. % O, 0-8 wt. % Re, and 0-1 wt. % Si.

In one non-limiting embodiment, a portion or all of the medical device is formed of a metal alloy that includes a) stainless steel, b) CoCr alloy, c) TiAlV alloy, d) aluminum alloy, e) nickel alloy, f) titanium alloy, g) tungsten alloy, h) molybdenum alloy, i) copper alloy, j) beryllium-copper alloy, k) titanium-nickel alloy, 1) refractory metal alloy, or m) metal alloy (e.g., stainless steel, CoCr alloy, TiAlV alloy, aluminum alloy, nickel alloy, titanium alloy, tungsten alloy, molybdenum alloy, copper alloy, beryllium-copper alloy, titanium-nickel alloy, refractory metal alloy, etc.) that includes at least 5 awt. %, and wherein a portion or all of the outer surface of the metal alloy is coated with an enhancement coating (e.g., chromium nitride (CrN), diamond-like carbon (DLC), titanium nitride (TiN), zirconium nitride (ZrN), zirconium oxide (ZrO2), zirconium-nitrogen-carbon (ZrNC), zirconium OxyCarbide (ZrOC), and wherein the outer surface of the metal alloy optionally includes an adhesion layer, which adhesion layer is optionally a metallic layer that includes titanium or zirconium.

In non-limiting configuration, a portion or all of the medical device is formed of a metal alloy that includes a) stainless steel, b) CoCr alloy, c) TiAlV alloy, d) aluminum alloy, e) nickel alloy, f) titanium alloy, g) tungsten alloy, h) molybdenum alloy, i) copper alloy, j) beryllium-copper alloy, k) titanium-nickel alloy, 1) refractory metal alloy, or m) metal alloy (e.g., stainless steel, CoCr alloy, TiAlV alloy, aluminum alloy, nickel alloy, titanium alloy, tungsten alloy, molybdenum alloy, copper alloy, beryllium-copper alloy, titanium-nickel alloy, refractory metal alloy, etc.) that includes at least 5 awt. %, and wherein the metal alloy is coated with an enhancement coating, and wherein the outer surface of the metal alloy optionally includes an adhesion layer, which adhesion layer is optionally a metallic layer that includes titanium or zirconium.

In another non-limiting configuration, the medical device is a stent or a prosthetic heart valve, and wherein all or a portion of the stent or frame of the prosthetic heart valve is formed of a titanium-nickel alloy or a titanium-nickel alloy that includes at least 5 awt. % rhenium, and wherein a portion or all of the outer surface of the metal alloy is coated with an enhancement coating, and wherein all or a portion of components other than the frame of the prosthetic heart valve (e.g., leaflet, skirts, etc.) are optionally coated with an enhancement coating, and wherein the outer surface of the metal alloy optionally includes an adhesion layer, which adhesion layer is optionally a metallic layer that includes titanium or zirconium.

In another non-limiting configuration, the medical device is a stent or a prosthetic heart valve, and wherein all or a portion of the stent or frame of the prosthetic heart valve is formed of a stainless-steel alloy or a stainless-steel alloy that includes at least 5 awt. % rhenium, and wherein a portion or all of the outer surface of the metal alloy is coated with an enhancement coating, and wherein all or a portion of components other than the frame of the prosthetic heart valve (e.g., leaflet, skirts, etc.) are optionally coated with an enhancement coating, and wherein the outer surface of the metal alloy optionally includes an adhesion layer, which adhesion layer is optionally a metallic layer that includes titanium or zirconium.

In another non-limiting configuration, the medical device is a stent or a prosthetic heart valve, and wherein all or a portion of the stent or frame of the prosthetic heart valve is formed of a cobalt-chromium alloy or a cobalt-chromium alloy that includes at least 5 awt. % rhenium, and wherein a portion or all of the outer surface of the metal alloy is coated with an enhancement coating, and wherein all or a portion of components other than the frame of the prosthetic heart valve (e.g., leaflet, skirts, etc.) are optionally coated with an enhancement coating, and wherein the outer surface of the metal alloy optionally includes an adhesion layer, which adhesion layer is optionally a metallic layer that includes titanium or zirconium.

In another non-limiting configuration, the medical device is a stent or a prosthetic heart valve, and wherein all or a portion of the stent or frame of the prosthetic heart valve is formed of a TiAlV alloy or a TiAlV alloy that includes at least 5 awt. % rhenium, and wherein a portion or all of the outer surface of the metal alloy is coated with an enhancement coating, and wherein all or a portion of components other than the frame of the prosthetic heart valve (e.g., leaflet, skirts, etc.) are optionally coated with an enhancement coating, and wherein the outer surface of the metal alloy optionally includes an adhesion layer, which adhesion layer is optionally a metallic layer that includes titanium or zirconium.

In another non-limiting configuration, the medical device is a stent or a prosthetic heart valve, and wherein all or a portion of the stent or frame of the prosthetic heart valve is formed of a refractory metal alloy or a refractory metal alloy that includes at least 5 awt. % rhenium, and wherein a portion or all of the outer surface of the metal alloy is coated with an enhancement coating, and wherein all or a portion of components other than the frame of the prosthetic heart valve (e.g., leaflet, skirts, etc.) are optionally coated with an enhancement coating, and wherein the outer surface of the metal alloy optionally includes an adhesion layer, which adhesion layer is optionally a metallic layer that includes titanium or zirconium.

In another non-limiting configuration, the medical device is a stent or a prosthetic heart valve, and wherein all or a portion of the stent or frame of the prosthetic heart valve is formed of a metal alloy that includes at least 5 awt. % rhenium, and wherein a portion or all of the outer surface of the metal alloy is coated with an enhancement coating, and wherein all or a portion of components other than the frame of the prosthetic heart valve (e.g., leaflet, skirts, etc.) are optionally coated with an enhancement coating, and wherein the outer surface of the metal alloy optionally includes an adhesion layer, which adhesion layer is optionally a metallic layer that includes titanium or zirconium.

In accordance with another and/or alternative non-limiting aspect of the present disclosure, the use of the metal alloy to form all or a portion of the medical device can result in several advantages over medical devices formed from other materials. These advantages include, but are not limited to:

The refractory metal alloy has increased strength and/or hardness as compared with stainless steel, chromium-cobalt alloys, or titanium alloys, thus a less quantity of refractory metal alloy can be used in the medical device to achieve similar strengths as compared to medical devices formed of different metals. As such, the resulting medical device can be made smaller and less bulky by use of the refractory metal alloy without sacrificing the strength and durability of the medical device. The medical device can also have a smaller profile, thus can be inserted into smaller areas, openings, and/or passageways. The thinner struts of refractory metal alloy to form the frame or other portions of the medical device can be used to form a frame or other portion of the medical device having a strength that would require thicker struts or other structures of the medical device when formed by stainless steel, chromium-cobalt alloys, or titanium alloys.

The increased strength of the refractory metal alloy also results in the increased radial strength of the medical device. For instance, the thickness of the walls of the medical device can be made thinner and achieve a similar or improved radial strength as compared with thicker walled medical devices formed of stainless steel, cobalt and chromium alloy, or titanium alloy.

The refractory metal alloy has improved stress-strain properties, bendability properties, elongation properties, and/or flexibility properties of the medical device compared with stainless steel and chromium-cobalt alloys, thus resulting in an increase life for the medical device. For example, the medical device can be used in regions that subject the medical device to repeated bending. Due to the improved physical properties of the medical device from the refractory metal alloy, the medical device has improved resistance to fracturing in such frequent bending environments. These improved physical properties at least in part result from the composition of the refractory metal alloy, the grain size of the refractory metal alloy, the carbon, oxygen, and nitrogen content of the refractory metal alloy, and/or the carbon/oxygen ratio of the refractory metal alloy.

The refractory metal alloy has a reduced degree of recoil during the crimping and/or expansion of the medical device compared with stainless steel, chromium-cobalt alloys, or titanium alloys. The medical device formed of the refractory metal alloy better maintains its crimped form and/or better maintains its expanded form after expansion due to the use of the refractory metal alloy. As such, when the medical device is to be mounted onto a delivery device when the medical device is crimped, the medical device better maintains its smaller profile during the insertion of the medical device in a body passageway. Also, the medical device better maintains its expanded profile after expansion to facilitate in the success of the medical device in the treatment area.

The use of the refractory metal alloy in the medical device results in the medical device better conforming to an irregularly shaped body passageway when expanded in the body passageway compared to a medical device formed by stainless steel, chromium-cobalt alloys, or titanium alloys.

The refractory metal alloy has improved radiopaque properties compared to standard materials such as stainless steel or cobalt-chromium alloy, thus reducing or eliminating the need for using marker materials on the medical device. For example, the refractory metal alloy is at least about 10-20% more radiopaque than stainless steel or cobalt-chromium alloy.

The refractory metal alloy has improved fatigue ductility when subjected to cold-working compared to the cold-working of stainless steel, chromium-cobalt alloys, or titanium alloys.

The refractory metal alloy has improved durability compared to stainless steel, chromium-cobalt alloys, or titanium alloys.

The refractory metal alloy has improved hydrophilicity compared to stainless steel, chromium-cobalt alloys, or titanium alloys.

The refractory metal alloy has reduced ion release in the body passageway compared to stainless steel, chromium-cobalt alloys, or titanium alloys.

The refractory metal alloy is less of an irritant to the body than stainless steel, cobalt-chromium alloy, or titanium alloys, thus can result in reduced inflammation, faster healing, increased success rates of the medical device. When the medical device is expanded in a body passageway, some minor damage to the interior of the passageway can occur. When the body begins to heal such minor damage, the body has less adverse reaction to the presence of the refractory metal alloy compared to other metals such as stainless steel, cobalt-chromium alloy, or titanium alloy.

The refractory metal alloy has a magnetic susceptibility that is lower that CoCr alloy, TiAlV alloys, and/or stainless steel, thus resulting in less incidence of potential defects to the medical device or complications to the patent after implantation of the medical device when the patient is subjected to an MRI or other medical device that generates a strong magnetic field.

One non-limiting object of the present disclosure is the provision of the metal alloy in accordance with the present disclosure that can be used to partially or fully form a medical device.

Another and/or alternative non-limiting object of the present disclosure is the provision of a medical device that is partially or fully formed of the metal alloy of the present disclosure and which medical device has improved procedural success rates.

Another and/or alternative non-limiting object of the present disclosure is the provision of a method and process for forming the metal alloy in accordance with the present disclosure that inhibits or prevents the formation of microcracks during the processing of the metal alloy.

Another and/or alternative non-limiting object of the present disclosure is the provision of a medical device that is partially or fully formed of the metal alloy in accordance with the present disclosure and wherein the medical device has improved physical properties.

Another and/or alternative non-limiting object of the present disclosure is the provision of a medical device that is at least partially formed of the metal alloy in accordance with the present disclosure that has increased strength and/or hardness.

Another and/or alternative non-limiting object of the present disclosure is the provision of a medical device that at least partially includes the metal alloy in accordance with the present disclosure and which metal alloy enables the medical device to be formed with less material without sacrificing the strength of the medical device compared to prior medical devices.

Another and/or alternative non-limiting object of the present disclosure is the provision of a method and process for forming the metal alloy in accordance with the present disclosure to inhibit or prevent the formation of microcracks during the processing of the metal alloy into a medical device.

Another and/or alternative non-limiting object of the present disclosure is the provision of a method and process for forming the metal alloy in accordance with the present disclosure that inhibits or prevents crack propagation and/or fatigue failure of the metal alloy.

Another and/or alternative non-limiting object of the present disclosure is the provision of a medical device that includes a metal alloy having a nitriding process to form a nitrided layer on the outer surface of the metal alloy.

Another and/or alternative non-limiting object of the present disclosure is the provision of a medical device that includes a metal alloy wherein the metal alloy has been subjected to a swaging process.

Another and/or alternative non-limiting object of the present disclosure is the provision of a medical device that includes a metal alloy wherein the metal alloy has been subjected to a cold-working process.

Another and/or alternative non-limiting object of the present disclosure is the provision of a medical device that includes a refractory metal alloy that has increased strength and/or hardness as compared with stainless steel, chromium-cobalt alloys, or titanium alloys.

Another and/or alternative non-limiting object of the present disclosure is the provision of a medical device that includes a refractory metal alloy thereby requiring a less quantity of refractory metal alloy to achieve similar strengths compared to medical devices formed of different metals.

Another and/or alternative non-limiting object of the present disclosure is the provision of a medical device that includes a refractory metal alloy wherein the medical device has a smaller crimped profile as compared to medical devices formed of different metals.

Another and/or alternative non-limiting object of the present disclosure is the provision of a medical device that includes a refractory metal alloy wherein the medical device has thinner walls and/or struts than in frames of a same shape that are formed of stainless steel, cobalt and chromium alloy or titanium alloy, and such frame formed of refractory metal alloy has the same or increase radial strength when the frame is expanded form a crimped configuration to an expanded configuration as compared to such frames formed of stainless steel or cobalt and chromium alloy, or titanium alloy.

Another and/or alternative non-limiting object of the present disclosure is the provision of a medical device that includes a refractory metal alloy wherein the medical device has improved stress-strain properties, bendability properties, elongation properties, and/or flexibility properties as compared to medical devices formed of stainless steel, titanium alloy, or chromium-cobalt alloys.

Another and/or alternative non-limiting object of the present disclosure is the provision of a medical device that includes a refractory metal alloy wherein the medical device has an increase life as compared to medical devices formed of stainless steel, titanium alloy, or chromium-cobalt alloys.

Another and/or alternative non-limiting object of the present disclosure is the provision of a medical device that includes a refractory metal alloy wherein the medical device has a reduced degree of recoil during the crimping and/or expansion of the medical device compared with frames of a similar size, shape and configuration that are formed of stainless steel, chromium-cobalt alloys, or titanium alloys.

Another and/or alternative non-limiting object of the present disclosure is the provision of a medical device that includes a refractory metal alloy wherein the medical device better conforms to an irregularly shaped body passageway when expanded in the body passageway as compared with frames of a similar size, shape and configuration that are formed of stainless steel, chromium-cobalt alloys, or titanium alloys.

Another and/or alternative non-limiting object of the present disclosure is the provision of a medical device that includes a refractory metal alloy wherein the medical device has improved fatigue ductility when subjected to cold-working as compared to the cold-working of frames of a similar size, shape and configuration that are formed of stainless steel, chromium-cobalt alloys, or titanium alloys.

Another and/or alternative non-limiting object of the present disclosure is the provision of a medical device that includes a refractory metal alloy wherein the medical device has improved durability as compared to stainless steel, chromium-cobalt alloys, or titanium alloys.

Another and/or alternative non-limiting object of the present disclosure is the provision of a medical device that includes a refractory metal alloy wherein the medical device has improved hydrophilicity as compared to stainless steel, chromium-cobalt alloys, or titanium alloys.

Another and/or alternative non-limiting object of the present disclosure is the provision of a medical device that includes a refractory metal alloy wherein the medical device has reduced ion release in the body passageway as compared to stainless steel, chromium-cobalt alloys, or titanium alloys.

Another and/or alternative non-limiting object of the present disclosure is the provision of a medical device that includes a refractory metal alloy wherein the medical device is less of an irritant to the body than stainless steel, cobalt-chromium alloy, or titanium alloys, thus can result in reduced inflammation, faster healing, and increased success rates of the medical device.

Another and/or alternative non-limiting object of the present disclosure is the provision of a metal alloy that includes an enhancement coating of chromium nitride (CrN), diamond-like carbon (DLC), titanium nitride (TiN), zirconium nitride (ZrN), zirconium oxide ($ZrO_2$), or zirconium OxyCarbide (ZrOC), that can be used to improve one or more properties of the metal alloy (e.g., change exterior color of metal alloy, increase hardness of coated surface, increase toughness of coated surface, reduced friction to coated surface, improve impact wear of coated surface, improve resistance to corrosion and oxidation, form a non-stick coated surface, improve biocompatibility of metal alloy having the coated surface, reduce toxicity of metal alloy having the coated surface, etc.).

These and other advantages will become apparent to those skilled in the art upon the reading and following of this description.

Although specific terms are used in the following description for the sake of clarity, these terms are intended to refer only to the particular structure of the embodiments selected for illustration in the drawings and are not intended to define or limit the scope of the disclosure. In the drawings and following description below, it is to be understood that like numeric designations refer to components of like function.

The singular forms "a," "an," and "the" include plural referents unless the context clearly dictates otherwise.

As used in the specification and in the claims, the term "comprising" may include the embodiments "consisting of" and "consisting essentially of" The terms "comprise(s)," "include(s)," "having," "has," "can," "contain(s)," and variants thereof, as used herein, are intended to be open-ended transitional phrases, terms, or words that require the presence of the named ingredients/steps and permit the presence of other ingredients/steps. However, such description should be construed as also describing compositions or processes as "consisting of" and "consisting essentially of" the enumerated ingredients/steps, which allows the presence of only the named ingredients/steps, along with any unavoidable impurities that might result therefrom, and excludes other ingredients/steps.

Numerical values in the specification and claims of this application should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 grams to 10 grams" is inclusive of the endpoints, 2 grams and 10 grams, and all the intermediate values).

The terms "about" and "approximately" can be used to include any numerical value that can vary without changing the basic function of that value. When used with a range, "about" and "approximately" also disclose the range defined by the absolute values of the two endpoints, e.g., "about 2 to about 4" also discloses the range "from 2 to 4." Generally, the terms "about" and "approximately" may refer to plus or minus 10% of the indicated number.

Percentages of elements should be assumed to be percent by weight of the stated element, unless expressly stated otherwise.

Medical devices, such as expandable heart valves, that are at least partially formed of the refractory metal alloy in accordance with the present disclosure overcome several unmet needs that exist in expandable medical device formed of CoCr alloys, TiAlV alloys, and stainless steel. Such unmet needs addressed by the medical devices in accordance with the present disclosure include 1) not having to form a large hole in large arterial vessels or other blood vessels for initial insertion of the crimped medical device into the atrial vessel or other blood vessel, thereby reducing the incidence of lethal bleeding during a treatment; 2) enabling the medical device to be delivered and implanted in abnormally shaped heart valves or through an abnormally shaped arterial vessel due to calcination in the heart valve and/or calcination and/or plaque in the arterial vessel by creating a medical device (e.g., stent, prosthetic heart valve, etc.) having a reduced crimped profile that is smaller than medical devices formed of CoCr alloys, TiAlV alloys, and stainless steel; 3) reducing the incidence of a perivalvular leak and/or other types of leakage about the implanted medical device when the medical device is expanded in the treatment region by using a frame formed of the refractory metal alloy that better conforms to the shape of the abnormally shaped heart valve orifice upon expansion of the prosthetic heart valve comparted to prior art prosthetic heart valves formed of CoCr alloys, TiAlV alloys, and stainless steel, thereby reducing the incidence of stroke and/or by increasing the incidence of success of the implanted medical device; 4) improving the radial strength of the expanded struts, posts, and/or strut joints in the expandable frame and the strength of the expandable frame itself after expansion the medical device; 5) reducing the amount of recoil of the expandable frame during the crimping and/or expansion of the expandable frame of the medical device; 6) enabling the medical device to be used in a heart that has a permanent pacemaker; 7) reducing the incidence of minor stroke during the insertion and operation of the medical device at the treatment area; 8) reducing the incidence of coronary ostium compromise; 9) improving foreshortening; 10) reducing further aortic valve calcification and/or calcification in a blood vessel after implantation of the medical device; 11) reducing the need for multiple crimping cycles when inserting the medical device on a catheter or other type of delivery system; 12) reducing the incidence of frame/stent fracture during the crimping and/or expansion of the medical device; 13) reducing the incidence of biofilm-endocarditis after implantation of the medical device; 14) reducing allergic reactions to the medical device after implantation of the medical device; 15) improving the hydrophilicity of the medical device to improve tissue growth on and/or about the implanted medical device, 16) reduce the magnetic susceptibility of the medical device, 17) reduce the toxicity of the medical device, 18) reduce the amount of metal ion release from the medical device, and/or 19) increasing the longevity of leaflets and/or stent/frame and/or other components of the medical device after insertion of the medical device.

In another non-limiting object of the present disclosure, there is provided a metal alloy comprising rhenium and one or more alloying metals, and wherein the metal alloy is used to at least partially form a medical device.

In another non-limiting object of the present disclosure, there is provided a metal alloy comprising rhenium and one or more alloying metals, and wherein the metal alloy is used to at least partially form a medical device; and wherein at least one region of the medical device includes at least one biological agent.

In another non-limiting object of the present disclosure, there is provided a metal alloy comprising rhenium and one or more alloying metals, and wherein the metal alloy is used to at least partially form a medical device; and wherein at least one region of the medical device includes at least one polymer.

In another non-limiting object of the present disclosure, there is provided a metal alloy comprising rhenium and one or more alloying metals, and wherein the metal alloy is used to at least partially form a medical device; and wherein at least one region of the medical device includes at least one polymer, the at least one polymer at least partially coats, encapsulates, or combinations thereof at least one biological agent.

In another non-limiting object of the present disclosure, there is provided a metal alloy comprising rhenium and one or more alloying metals, and wherein the metal alloy is used to at least partially form a medical device; and wherein at least one micro-structure is located on an outer surface of the medical device; and wherein the at least one microstructure optionally is at least partially formed of, includes, or combinations thereof, a material consisting of a polymer, an agent, or combinations thereof.

In another non-limiting object of the present disclosure, there is provided a metal alloy comprising rhenium and one or more alloying metals, and wherein the metal alloy is used to at least partially form a medical device; and wherein the medical device includes an expandable frame formed of the metal alloy; the expandable frame including a plurality of struts; the expandable frame is optionally configured to be crimped to a crimped state such that a maximum outer diameter of the expandable frame when in the crimped state is less than a maximum outer diameter of the expandable frame when fully expanded to an expanded state; and wherein the expandable frame optionally has a recoil of less than 5% (e.g., 0.1-4.99 and all values and ranges therebetween) after being subjected to a first crimping process; and wherein the expandable frame optionally has a recoil of less than 5% (e.g., 0.1-4.99 and all values and ranges therebetween) after being expanded from the crimped state to the expanded state; and wherein the metal alloy optionally has a hydrophilicity wherein a contact angle of a water droplet on a surface of said metal alloy of 25-45° (e.g., 0.1-4.99 and all values and ranges therebetween); and wherein the metal alloy optionally has a maximum ion release of a primary component of said metal alloy when inserted or implanted on or in the body of the patient of no more than 0.5 µg/cm$^2$ per day (e.g., 0.001-0.5 µg/cm$^2$ per day and all values and ranges therebetween); and wherein the primary component constitutes at least 2 wt. % of the metal alloy; and wherein the metal alloy optionally has an absolute increase in ion release per dose of metal alloy in tissue about said medical device of no more than 50 days after inserted or implanted on or in the body of a patient.

In another non-limiting object of the present disclosure, there is provided a metal alloy comprising rhenium and one or more alloying metals, and wherein the metal alloy is used to at least partially form a medical device; and wherein the medical device is an expandable stent or an expandable prosthetic heart valve.

In another non-limiting object of the present disclosure, there is provided a metal alloy comprising rhenium and one or more alloying metals, and wherein the metal alloy is optionally used to at least partially form a medical device; and wherein the one or more alloying metals are selected from the group consisting of aluminum, bismuth, calcium, carbon, chromium, cobalt, copper, gold, hafnium, iridium, iron, lanthanum, magnesium, manganese, molybdenum, nickel, niobium, osmium, platinum, rare earth metals, rhodium, ruthenium, silver, tantalum, technetium, titanium, tungsten, vanadium, yttrium, zinc, zirconium, and/or alloys of one or more of such components; and wherein a combined weight percent of the rhenium, molybdenum, and the one or more alloying metals in the metal alloy is at least 99.9 wt. %; and wherein the metal alloy optionally has a maximum ion release of a primary component of the metal alloy when inserted or implanted on or in a body of a patient of no more than 0.5 µg/cm$^2$ per day (e.g., 0.001-0.5 µg/cm$^2$ per day and all values and ranges therebetween); and wherein the primary component constitutes at least 2 wt. % of the metal alloy.

It will thus be seen that the objects set forth above, among those made apparent from the preceding description, are efficiently attained, and since certain changes may be made in the constructions set forth without departing from the spirit and scope of the disclosure, it is intended that all matter contained in the above description and shown in the accompanying drawings shall be interpreted as illustrative and not in a limiting sense. The disclosure has been described with reference to preferred and alternate embodiments. Modifications and alterations will become apparent to those skilled in the art upon reading and understanding the detailed discussion of the disclosure provided herein. This disclosure is intended to include all such modifications and alterations insofar as they come within the scope of the present disclosure. It is also to be understood that the following claims are intended to cover all of the generic and specific features of the disclosure herein described and all statements of the scope of the disclosure, which, as a matter of language, might be said to fall therebetween.

What is claimed:

1. A metal alloy that includes an enhancement coating that is directly coated on an outer surface of said metal alloy; said metal alloy comprising rhenium and one or more additives selected from the group consisting of aluminum, bismuth, calcium, carbon, chromium, cobalt, copper, gold, hafnium, iridium, iron, lanthanum, magnesium, manganese, molybdenum, nickel, niobium, osmium, platinum, rhodium, ruthenium, silver, tantalum, technetium, titanium, tungsten, vanadium, yttrium, and/or zirconium; a combined weight percentage of rhenium and said one or more additives in said metal alloy is at least 98 wt. %; said enhancement coating has a coating thickness of 2 nanometers to 100 microns; said enhancement coating includes one or more layers of material coated on said outer surface of said metal alloy; said enhancement coating is at least partially applied to said outer surface of said metal alloy by a physical vapor deposition (PVD) process, a chemical vapor deposition (CVD) process, an atomic layer deposition (ALD) process, a plasma-enhanced chemical vapor deposition (PE-CVD) process, ion implantation, direct energy deposition (DED), and/or thermal spray technique; said enhancement coating has a composition that is different from said metal alloy; said enhancement coating includes no more than 0.1 wt. % nickel, and/or no more than 0.1 wt. % cobalt; said enhancement coating is formed of a) 35-95 wt. % zirconium and wherein said enhancement coating includes ZrN, ZrNC, ZrOC or a combination of ZrN and $ZrO_2$, b) 20-85 wt. % titanium and one or more of carbon, nitrogen, oxygen, rhenium, and silicon, c) 40-85 wt. % chromium and one or more of carbon, nitrogen, oxygen, rhenium, and silicon, or d) at least 60 wt. % carbon.

2. The metal alloy defined in claim 1, wherein said enhancement coating is formed of multi layers having a same or different coating layer composition.

3. The metal alloy as defined in claim 1, wherein said enhancement coating includes nitrides and/or oxides of one or more elements selected from the group consisting of Cr, Ti, Zr, and Al.

4. The metal alloy as defined in claim 1, wherein said enhancement coating includes a) 40-80 wt. % zirconium and one or more of 5-25 wt. % nitrogen, 25-40 wt. % carbon, 20-30 wt. % oxygen, 0-1 wt. % silicon and 0-1 wt. % rhenium, b) 20-80 wt. % titanium and 5-30 wt. % nitrogen, carbon, oxygen, 0-1 wt. % silicon and 0-1 wt. % rhenium, or c) 65-85 wt. % chromium, 15-30 wt. % nitrogen, carbon, oxygen, 0-1 wt. % silicon and 0-1 wt. % rhenium.

5. The metal alloy as defined in claim 1, wherein said enhancement coating is formed of a) 65-80 wt. % Cr, 15-30 wt. % N, 0-8 wt. % Re, 0-1 wt. % Si, 0-1 wt. % O, and 0-1 wt. % C, b) 70-80 wt. % Ti, 20-25 wt. % N, 0-8 wt. % Re, 0-1 wt. % Si, 0-1 wt. % O, and 0-1 wt. % C, c) 80-90 wt. % Zr, 10-20 wt. % N, 0-8 wt. % Re, 0-1 wt. % Si, 0-1 wt. % O, and 0-1 wt. % C, d) 70-80 wt. % Zr, 20-30 wt. % O, 0-1 wt. % N, 0-8 wt. % Re, 0-1 wt. % Si, and 0-1 wt. % C, e) 40-65 wt. % Zr, 5-25 wt. % O, and 25-40 wt. % C, 0-1 wt. % N, 0-8 wt. % Re, and 0-1 wt. % Si, or f) 40-80 wt. % Zr, 5-25 wt. % N, and 5-25 wt. % C, 0-1 wt. % O, 0-8 wt. % Re, and 0-1 wt. % Si.

6. The metal alloy as defined in claim 1, wherein said enhancement coating includes first and second coating layers, said first coating layer includes 80-90 wt. % Zr, 10-20 wt. % N, 0-8 wt. % Re, 0-1 wt. % Si, 0-1 wt. % O, and 0-1 wt. % C; said second coating layer is applied to a top surface of said first coating layer; said second coating layer includes 70-80 wt. % Zr, 20-30 wt. % O, 0-1 wt. % N, 0-8 wt. % Re, 0-1 wt. % Si, and 0-1 wt. % C.

7. The metal alloy as defined in claim 1, wherein said enhancement coating includes one or more of chromium nitride (CrN), diamond-like carbon (DLC), titanium nitride (TiN), zirconium nitride (ZrN), zirconium oxide ($ZrO_2$), zirconium-nitrogen-carbon (ZrNC), zirconium OxyCarbide (ZrOC), and combinations thereof.

8. The metal alloy as defined in claim 1, wherein said coating thickness of said enhancement coating is 0.1-25 microns.

9. The metal alloy as defined in claim 1, wherein said enhancement coating has a hardness of 5-50 GPa.

10. The metal alloy as defined in claim 1, wherein said enhancement coating has a coefficient of friction (COF) of 0.04-0.2.

11. The metal alloy as defined in claim 1, wherein said enhancement coating has a wear rate of $0.5 \times 10^{-7}$ mm³/N-m to $3 \times 10^{-7}$ mm³/N-m.

12. The metal alloy as defined in claim 1, wherein said metal alloy includes less than 0.1 wt. % nickel, less than 0.1 wt. % chromium, and/or less than 0.1 wt. % cobalt.

13. The metal alloy as defined in claim 1, wherein said metal alloy includes 50-75 wt. % rhenium, 25-50 wt. % Cr, and 0.5-25 wt. % of said one or more additives; said one or more additives includes one or more metals selected from the group consisting of bismuth, iridium, manganese, molybdenum, niobium, tantalum, vanadium, titanium, tungsten, yttrium, and zirconium.

14. The metal alloy as defined in claim 13, wherein said metal alloy includes 0-2 wt. % of said one or more metal additives; said one or more additives selected from the group consisting of metals other than rhenium, bismuth, iridium, molybdenum, niobium, tantalum, vanadium, yttrium, and zirconium.

15. The metal alloy as defined in claim 1, wherein said metal alloy includes 55-75 wt. % rhenium, 25-45 wt. % Cr, and 0.5-25 wt. % of said one or more additives; said one or more additives includes one or more metals selected from the group consisting of bismuth, iridium, molybdenum, niobium, tantalum, vanadium, yttrium, and zirconium; and said metal alloy includes 0-0.1 wt. % of secondary materials; said secondary materials are selected from the group consisting of a) metals other than rhenium, bismuth, iridium, molybdenum, niobium, tantalum, vanadium, yttrium, and zirconium, b) carbon, c) oxygen and d) nitrogen.

16. A medical device that is at least partially formed of said metal alloy as defined in claim 1.

17. The medical device as defined in claim 16, wherein said medical device includes an expandable frame formed of said metal alloy; said expandable frame includes a plurality of struts; said expandable frame is configured to be crimped to a crimped state such that a maximum outer diameter of said expandable frame when in said crimped state is less than a maximum outer diameter of said expandable frame when fully expanded to an expanded state; said expandable frame has a recoil of less than 5% after being subjected to a first crimping process; said expandable frame has a recoil of less than 5% after being expanded from said crimped state to said expanded state; said metal alloy has a hydrophilicity wherein a contact angle of a water droplet on a surface of said metal alloy of 25-45°; said metal alloy has a maximum ion release of a primary component of said metal alloy when inserted or implanted on or in a body of a patient of no more than 0.5 μg/cm² per day, wherein said primary component constitutes at least 2 wt. % of said metal alloy; said metal alloy has an absolute increase in ion release per dose of metal alloy in tissue about said medical device of no more than 50 days after inserted or implanted on or in the body of the patient.

18. The metal alloy as defined in claim 1, wherein said metal alloy is formed from metal powders that have been sintered together.

19. A method for forming said metal alloy as defined in claim 18 comprising:
providing said metal powders; said metal powders include rhenium metal powder and said one or more additives;
compressing together said metal powders;
sintering said compressed metal powders to form said metal alloy; and;
coating an outer surface of said metal alloy with said enhancement coating; said enhancement coating includes two or more elements selected form the group consisting of chromium, carbon, nitrogen, titanium, zirconium, oxygen, aluminum, chromium, and boron.

20. A metal alloy that includes an enhancement coating that is directly coated on an outer surface of said metal alloy; said metal alloy comprising rhenium and one or more additives selected from the group consisting of aluminum, bismuth, calcium, carbon, chromium, cobalt, copper, gold, hafnium, iridium, iron, lanthanum, magnesium, manganese, molybdenum, nickel, niobium, osmium, platinum, rhodium, ruthenium, silver, tantalum, technetium, titanium, tungsten, vanadium, yttrium, zinc, and/or zirconium; a combined weight percentage of rhenium and said one or more additives in said metal alloy is at least 98 wt. %; and wherein said enhancement coating is formed of a single layer or multi layers; said enhancement coating has a composition that is different from said metal alloy; said enhancement coating is at least partially applied to said outer surface of said metal alloy by a physical vapor deposition (PVD) process, a chemical vapor deposition (CVD) process, an atomic layer deposition (ALD) process, a plasma-enhanced chemical vapor deposition (PE-CVD) process, ion implantation, direct energy deposition (DED), and/or thermal spray technique; said enhancement coating has a coating thickness of 2 nanometers to 100 microns; said enhancement coating includes no more than 0.1 wt. % nickel, and/or no more than 0.1 wt. % cobalt; said enhancement coating is formed of a) 35-95 wt. % zirconium, and wherein said enhancement coating includes ZrN, ZrNC, ZrOC or a combination of ZrN and $ZrO_2$, b) 20-85 wt. % titanium and one or more of carbon, nitrogen, oxygen, rhenium, and silicon, c) 40-85 wt. % chromium and one or more of carbon, nitrogen, oxygen, rhenium, and silicon, or d) at least 60 wt. % carbon.

21. The metal alloy as defined in claim 20, wherein said enhancement coating includes nitrides and/or oxides of one or more elements selected from the group consisting of Cr, Ti, Zr, and Al.

22. The metal alloy as defined in claim 21, wherein said enhancement coating includes a) 40-80 wt. % zirconium and one or more of 5-25 wt. % nitrogen, 25-40 wt. % carbon, 20-30 wt. % oxygen, 0-1 wt. % silicon and 0-1 wt. % rhenium, b) 20-80 wt. % titanium and 5-30 wt. % nitrogen, carbon, oxygen, 0-1 wt. % silicon and 0-1 wt. % rhenium, or c) 65-85 wt. % chromium, 15-30 wt. % nitrogen, carbon, oxygen, 0-1 wt. % silicon and 0-1 wt. % rhenium.

23. The metal alloy as defined in claim 21, wherein said enhancement coating is formed of a) 65-80 wt. % Cr, 15-30 wt. % N, 0-8 wt. % Re, 0-1 wt. % Si, 0-1 wt. % O, and 0-1 wt. % C, b) 70-80 wt. % Ti, 20-25 wt. % N, 0-8 wt. % Re, 0-1 wt. % Si, 0-1 wt. % O, and 0-1 wt. % C, c) 80-90 wt. % Zr, 10-20 wt. % N, 0-8 wt. % Re, 0-1 wt. % Si, 0-1 wt. % O, and 0-1 wt. % C, d) 70-80 wt. % Zr, 20-30 wt. % O, 0-1 wt. % N, 0-8 wt. % Re, 0-1 wt. % Si, and 0-1 wt. % C, e) 40-65 wt. % Zr, 5-25 wt. % O, and 25-40 wt. % C, 0-1 wt. % N, 0-8 wt. % Re, and 0-1 wt. % Si, or f) 40-80 wt. % Zr, 5-25 wt. % N, and 5-25 wt. % C, 0-1 wt. % O, 0-8 wt. % Re, and 0-1 wt. % Si.

24. The metal alloy as defined in claim 23, wherein said enhancement coating includes first and second coating layers said first coating layer includes 80-90 wt. % Zr, 10-20 wt. % N, 0-8 wt. % Re, 0-1 wt. % Si, 0-1 wt. % O, and 0-1 wt. % C; said second coating layer is applied to a top surface of said first layer; said second coating layer includes 70-80 wt. % Zr, 20-30 wt. % O, 0-1 wt. % N, 0-8 wt. % Re, 0-1 wt. % Si, and 0-1 wt. % C.

25. The metal alloy as defined in claim 24, wherein said enhancement coating has a) said coating thickness of 0.1-25 microns, b) a hardness of 5-50 GP, c) a coefficient of friction (COF) of 0.04-0.2, and d) a wear rate of $0.5 \times 10^{-7}$ mm$^3$/N-m to $3 \times 10^{-7}$ mm$^3$/N-m.

26. The metal alloy as defined in claim 24, wherein said metal alloy includes 50-75 wt. % rhenium, 25-50 wt. % Cr, and 0.5-25 wt. % of said one or more additives; said one or more additives includes one or more metals selected from the group consisting of bismuth, iridium, manganese, molybdenum, niobium, tantalum, vanadium, titanium, tungsten, yttrium, and zirconium.

27. The medical device as defined in claim 16, wherein said medical device is a stent, a valve, or a valve frame.

* * * * *